United States Patent
Choi et al.

(10) Patent No.: US 9,865,826 B2
(45) Date of Patent: Jan. 9, 2018

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Jongwon Choi, Yongin-si (KR); Seungyeon Kwak, Yongin-si (KR); Yoonhyun Kwak, Seoul (KR); Ohyun Kwon, Yongin-si (KR); Jiwhan Kim, Seoul (KR); Kumhee Lee, Suwon-si (KR); Sunyoung Lee, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 407 days.

(21) Appl. No.: 14/579,499

(22) Filed: Dec. 22, 2014

(65) Prior Publication Data
US 2016/0013431 A1 Jan. 14, 2016

(30) Foreign Application Priority Data
Jul. 9, 2014 (KR) .................. 10-2014-0086154

(51) Int. Cl.
| | |
|---|---|
| B32B 9/00 | (2006.01) |
| B32B 19/00 | (2006.01) |
| C07F 15/00 | (2006.01) |
| H01L 51/00 | (2006.01) |
| C07D 401/14 | (2006.01) |
| C07D 403/14 | (2006.01) |
| H01L 51/50 | (2006.01) |

(52) U.S. Cl.
CPC ........ *H01L 51/0087* (2013.01); *C07D 401/14* (2013.01); *C07D 403/14* (2013.01); *C07F 15/0026* (2013.01); *C07F 15/0086* (2013.01); *C07F 15/0093* (2013.01); *H01L 51/0088* (2013.01); *H01L 51/0081* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 6,465,115 B2 | 10/2002 | Shi et al. | |
| 6,596,415 B2 | 7/2003 | Shi et al. | |
| 6,830,828 B2 | 12/2004 | Thompson et al. | |
| 7,002,013 B1 | 2/2006 | Chi et al. | |
| 7,329,898 B2 | 2/2008 | Igarashi | |
| 7,442,797 B2 | 10/2008 | Itoh et al. | |
| 7,732,606 B2 | 6/2010 | Ise et al. | |
| 8,211,553 B2 | 7/2012 | Nii et al. | |
| 2001/0019782 A1 | 9/2001 | Igarashi et al. | |
| 2012/0169220 A1 | 7/2012 | Nii et al. | |
| 2013/0313536 A1 | 11/2013 | Nishimura et al. | |

FOREIGN PATENT DOCUMENTS

JP 2000-003782 A 1/2000

OTHER PUBLICATIONS

Constable, et. al., Polyhedron (1982), 311-312.*
Baldo et al., "Highly efficient phosphorescent emission from organic electroluminescent devices", Nature, 1998, 395, pp. 151-154.
Baldo et al., "Very highly-efficiency green organic light-emitting devices based on electrophosphorescence", Applied Physics Letters, 1999, vol. 75, No. 1, pp. 4-6.
Lamansky et al., "Highly Phosphorescent Bis-Cyclometalated Iridium Complexes: Synthesis, Photophysical Characterization, and Use in Organic Light Emitting Diodes", J. Am. Chem. Soc., 2001, 123, pp. 4304-4312.
Lamansky et al., "Synthesis and Characterization of Phosphorescent Cyclometalated Iridium Complexes", Inorg. Chem., 2001, 40, pp. 1704-1711
"Palladium-catalyzed double cross-coupling reaction of 1,2-bis(pinacolatoboryl)alkenes and -arenes with 2,2'-dibromobiaryls: annulative approach to functionalized polycyclic aromatic hydrocarbons", Tetrahedron, 2011, 67(41), 8014-8026.

* cited by examiner

*Primary Examiner* — Jeffrey H Murray
(74) *Attorney, Agent, or Firm* — Cantor Colburn LLP

(57) ABSTRACT

An organometallic compound of Formula 1:

Formula 1

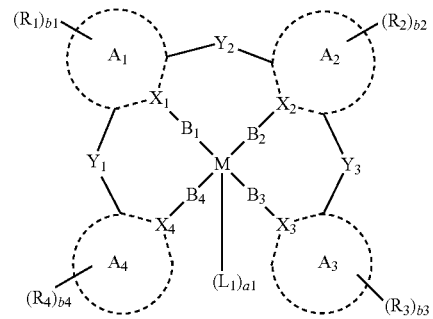

wherein in Formula 1, groups and variables are as described in the specification.

9 Claims, 1 Drawing Sheet

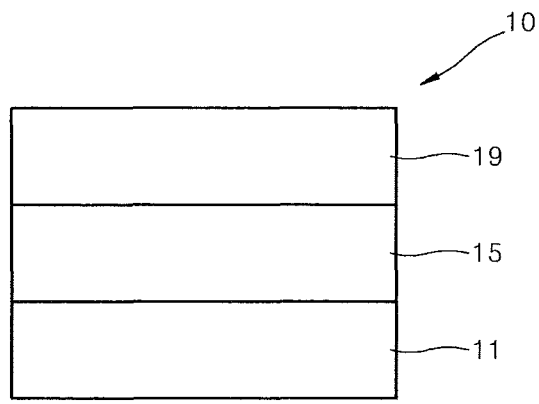

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0086154, filed on Jul. 9, 2014, in the Korean Intellectual Property Office, and all the benefits accruing therefrom under 35 U.S.C. §119, the content of which is incorporated herein in its entirety by reference.

BACKGROUND

1. Field

The present disclosure relates to an organometallic compound and an organic light-emitting device including the same.

2. Description of the Related Art

Organic light emitting devices (OLEDs) are self-emission devices that have wide viewing angles, high contrast ratios, short response times, and excellent brightness, driving voltage, and response speed characteristics, and produce full-color images.

A typical organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

One or more embodiments relate to an organometallic compound and an organic light-emitting device including the same.

Additional aspects will be set forth in part in the description which follows and, in part, will be apparent from the description, or may be learned by practice of the presented embodiments.

An embodiment provides an organometallic compound represented by Formula 1:

Formula 1

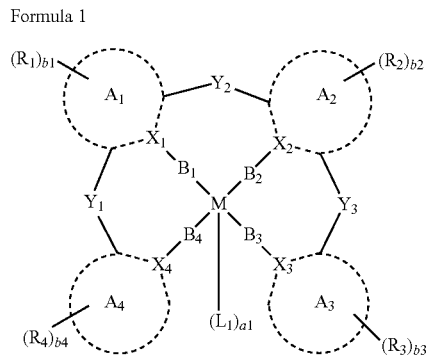

wherein in Formula 1,

M is selected from a Period 1 transition metal, a Period 2 transition metal, and a Period 3 transition metal;

$A_1$ ring to $A_4$ ring are each independently selected from a $C_6$-$C_{20}$ carbocyclic group and a $C_1$-$C_{20}$ heterocyclic group, provided that each of the $A_3$ ring and the $A_4$ ring is not simultaneously a benzene;

$X_1$ to $X_4$ are each independently selected from C and N;

$B_1$ to $B_4$ are each independently selected from a single bond, —O—, and —S—;

$Y_1$ and $Y_3$ are each independently selected from a single bond and a divalent linking group;

$Y_2$ is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic hetero-condensed polycyclic group;

$L_1$ is selected from a monodentate ligand and a bidentate ligand;

a1 is selected from 0, 1, and 2;

$R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic hetero-condensed polycyclic group, —C(=O)($Q_1$), —Si($Q_1$)($Q_2$)($Q_3$), and —N($Q_1$)($Q_2$); wherein $R_1$ and $R_4$ or $R_2$ and $R_3$ may be optionally linked to form a saturated or unsaturated ring;

$Q_1$ to $Q_3$ are each independently selected from a $C_1$-$C_{60}$ alkyl group and a $C_6$-$C_{60}$ aryl group;

b1 to b4 are each independently selected from 1, 2, 3, and 4;

at least one substituent of the substituted $C_6$-$C_{60}$ arylene group, substituted $C_1$-$C_{60}$ heteroarylene group, substituted divalent non-aromatic condensed polycyclic group, the substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic hetero-condensed polycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ hetero aryl group, a monovalent non-aromatic condensed polycyclic group, and a monovalent non-aromatic hetero-condensed polycyclic group.

In some embodiments, an organic light-emitting device includes:

a first electrode;

a second electrode; and an organic layer disposed between the first electrode and the second electrode, wherein the organic layer includes an emission layer and or more organometallic compounds represented by Formula 1.

The emission layer may include the organometallic compound and may further include a host; and the organometallic compound may be a dopant.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of" when preceding a list of elements, modify the entire list of elements and do not modify the individual elements of the list.

The present invention may be variously modified and have several embodiments. Accordingly, particular embodiments will be illustrated in the drawings and described in the detailed description in detail. Advantages, features, and how to achieve them will become apparent by reference to the embodiment that will be described later in detail, together with the accompanying drawings. This invention may, however, be embodied in many different forms and should not be limited to the exemplary embodiments.

Hereinafter, embodiments are described in detail by referring to the attached drawings, and in the drawings, like reference numerals denote like elements, and a redundant explanation thereof will not be provided herein.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a," "an" and "the" are intended to include the plural forms as well, unless the context clearly indicates otherwise.

It will be further understood that the terms "comprises" and/or "comprising," or "includes" and/or "including" used herein specify the presence of stated features, regions, integers, steps, operations, elements, and/or components, but do not preclude the presence or addition of one or more other features, regions, integers, steps, operations, elements, components, and/or groups thereof.

It will be understood that when a layer, region, or component is referred to as being "on" or "onto" another layer, region, or component, it may be directly or indirectly formed on the other layer, region, or component. That is, for example, intervening layers, regions, or components may be present. In contrast, when an element is referred to as being "directly on" another element, there are no intervening elements present.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Sizes of components in the drawings may be exaggerated for convenience of explanation. In other words, since sizes and thicknesses of components in the drawings are arbitrarily illustrated for convenience of explanation, the following embodiments are not limited thereto.

The term "organic layer" used herein refers to a single layer and/or a plurality of layers disposed between the first electrode and the second electrode of the organic light-emitting device. A material included in the "organic layer" is not limited to an organic material.

An organometallic compound according to an embodiment is represented by Formula 1 below:

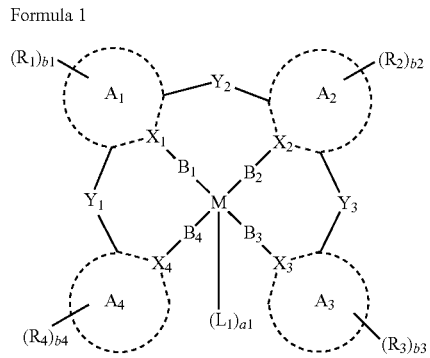

Formula 1 wherein in Formula 1,

M may be a transition metal.

For example, M in Formula 1 may be selected from a Period 1 transition metal, a Period 2 transition metal, and a Period 3 transition metal, but is not limited thereto.

In some embodiments, M in Formula 1 may be selected from a Period 3 transition metal, but is not limited thereto.

In some embodiments, M in Formula 1 may be selected from a Period 3 transition metal having an atomic weight of 180 or greater, but is not limited thereto.

In some embodiments, M in Formula 1 may be selected from osmium (Os), iridium (Ir), and platinum (Pt), but is not limited thereto.

In some embodiments, M in Formula 1 may be selected from Os and Pt, but is not limited thereto.

$A_1$ ring to $A_4$ in Formula 1 ring may be each independently selected from a $C_6$-$C_{20}$ cyclic group and a $C_1$-$C_{20}$ heterocyclic group, provided that each of the $A_3$ ring and the $A_4$ ring is not simultaneously a benzene.

For example, $A_1$ ring to $A_4$ ring in Formula 1 may be each independently selected from a benzene, a naphthalene, a pyrrole, an imidazole, a pyrazole, a thiazole, an isothiozole, an oxazole, an isoxazole, a triazole, an indazole, a tetrahydroindazole, a pyridine, a pyrimidine, a pyrazine, a pyridazine, a triazine, a quinoline, an isoquinoline, a dibenzofuran, and a dibenzothiophene, but are not limited thereto. Here, each of $A_3$ ring and $A_4$ ring are not simultaneously a benzene.

In some embodiments, $A_1$ ring to $A_4$ ring in Formula 1 may be each independently selected from a benzene, a pyrazole, an indazole, a tetrahydroindazole, a pyridine, a quinoline, an isoquinoline, and a dibenzofuran, but are not limited thereto. Here, each of the $A_3$ ring and the $A_4$ ring are not simultaneously a benzene.

In some embodiments, $A_1$ ring and $A_2$ ring in Formula 1 may be each independently selected from a benzene, a pyridine, a quinoline, and an isoquinoline; $A_3$ ring and $A_4$ ring may be each independently selected from a benzene, a pyrazole, indazole, tetrahydroindazole, a pyridine, a quinoline, an isoquinoline, and a dibenzofuran, but are not limited thereto. Here, each of the $A_3$ ring and the $A_4$ ring are not simultaneously a benzene.

$X_1$ to $X_4$ in Formula 1 may be each independently selected from a carbon atom (C) and a nitrogen atom (N).

For example, in Formula 1, $X_1$ and $X_2$ may be C, and $X_3$ and $X_4$ may be N, but they are not limited thereto.

In some embodiments, in Formula 1, $X_1$ and $X_3$ may be C, and $X_2$ and $X_4$ may be N, but they are not limited thereto.

In some embodiments, in Formula 1, $X_2$ and $X_4$ may be C, and $X_1$ and $X_3$ may be N, but they are not limited thereto.

In some embodiments, in Formula 1, $X_1$ may be C, and $X_2$, $X_3$ and $X_4$ may be N, but they are not limited thereto.

In some embodiments, in Formula 1, $X_2$ may be C, and $X_1$, $X_3$ and $X_4$ may be N, but they are not limited thereto.

In some embodiments, in Formula 1, $X_3$ may be C, and $X_1$, $X_2$ and $X_4$ may be N, but they are not limited thereto.

In some embodiments, in Formula 1, $X_4$ may be C, and $X_1$, $X_2$ and $X_3$ may be N, but they are not limited thereto.

In some embodiments, $X_1$ to $X_4$ in Formula 1 may be N, but are not limited thereto.

$B_1$ to $B_4$ in Formula 1 may be each independently selected from a single bond and a divalent linking group.

For example, $B_1$ to $B_4$ in Formula 1 may be each independently selected from a single bond, —O—, and —S—, but are not limited thereto.

In some embodiments, $B_1$ to $B_4$ in Formula 1 may be each independently selected from a single bond and —O—, but are not limited thereto.

In some embodiments, $B_1$ to $B_4$ in Formula 1 may be a single bond, but are not limited thereto.

$Y_1$ and $Y_3$ in Formula 1 may be each independently selected from a single bond and a divalent linking group.

For example, $Y_1$ and $Y_3$ in Formula 1 may be each independently selected from a single bond, —O—, —S—, —{B($Q_{11}$)}-, —{N($Q_{12}$)}-, —{C($Q_{11}$)($Q_{12}$)}$_{n1}$-, —{Si($Q_{11}$)($Q_{12}$)}$_{n1}$-, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic hetero-condensed polycyclic group;

$Q_{11}$ and $Q_{12}$ may be each independently selected from a hydrogen, a deuterium, a $C_1$-$C_{60}$ alkyl group, a $C_6$-$C_{60}$ aryl group, and a $C_1$-$C_{60}$ heteroaryl group;

n1 may be selected from 1, 2, and 3;

at least one substituent of the substituted $C_6$-$C_{60}$ arylene group, substituted $C_1$-$C_{60}$ heteroarylene group, substituted divalent non-aromatic condensed polycyclic group, and substituted divalent non-aromatic hetero-condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group, but is not limited thereto.

In some embodiments, $Y_1$ and $Y_3$ in Formula 1 may be each independently selected from a single bond, —O—, —S—, —{B($Q_{11}$)}-, —{N($Q_{11}$)}-, —{C($Q_{11}$)($Q_{12}$)}$_{n1}$-, —{Si($Q_{11}$)($Q_{12}$)}$_{n1}$-, a phenylene group, a naphthylene group, a fluorenylene group, a pyridinylene group, a pyrazinylene group, a pyrimidinylene group, a quinolinylene group, an isoquinolinylene group, a naphthyridinylene group, a quinoxalinylene group, a quinazolinylene group, a dibenzofuranylene group, and a dibenzothiophenylene group; and a phenylene group, a naphthylene group, a fluorenylene group, a pyridinylene group, a pyrazinylene group, a pyrimidinylene group, a quinolinylene group, an isoquinolinylene group, a naphthyridinylene group, a quinoxalinylene group, a quinazolinylene group, a dibenzofuranylene group and a dibenzothiophenylene group, each substituted with at least one selected from a deuterium, —F, —Cl, —Br, —I, a methyl group, an ethyl group, a n-propyl group, an iso-propyl group, a n-butyl group, an iso-butyl group, a sec-butyl group, a tert-butyl group, a phenyl group, and a pyridinyl group;

$Q_{11}$ and $Q_{12}$ may be each independently selected from a hydrogen, a deuterium, a methyl group, an ethyl group, a n-propyl group, an iso-propyl group, an n-butyl group, an iso-butyl group, a tert-butyl group, and a phenyl group;

n1 may be 1, but is not limited thereto.

In some embodiments, $Y_1$ and $Y_3$ in Formula 1 may be each independently selected from a single bond, —O—, —S—, —N(CH$_3$)—, —N(Ph)-, —CH$_2$—, —C(CH$_3$)$_2$—, —C(CH$_3$)(Ph)-, —C(Ph)$_2$-, and Formulae 3-1 to 3-17 below, but are not limited thereto:

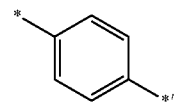

3-1

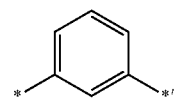

3-2

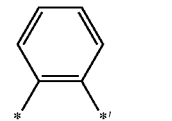

3-3

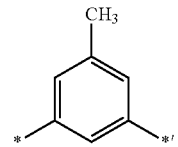

3-4

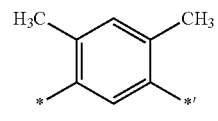

3-5

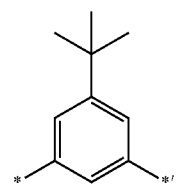

3-6

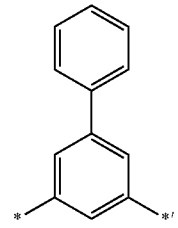

3-7

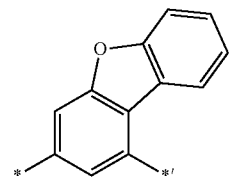

3-8

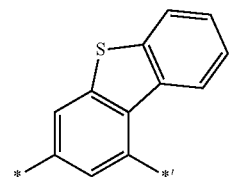

3-9

-continued

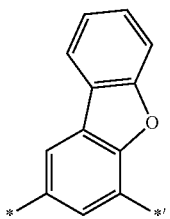
3-10

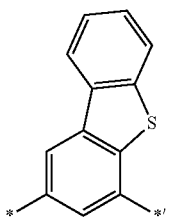
3-11

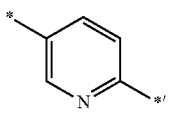
3-12

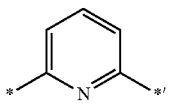
3-13

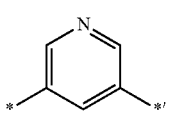
3-14

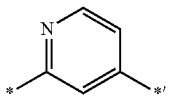
3-15

3-16

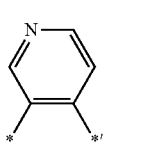
3-17 wherein in Formulae 3-1 to 3-17, each of * and *' indicates a binding site to a neighboring atom.

In some embodiments, $Y_1$ and $Y_3$ in Formula 1 may be a single bond, but are not limited thereto.

$Y_2$ in Formula 1 may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic hetero-condensed polycyclic group;

at least one substituent of the substituted $C_6$-$C_{60}$ arylene group, substituted $C_1$-$C_{60}$ heteroarylene group, substituted divalent non-aromatic condensed polycyclic group, and substituted divalent non-aromatic hetero-condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group.

For example, $Y_2$ in Formula 1 may be selected from a phenylene group, a naphthylene group, a fluorenylene group, a pyridinylene group, a pyrazinylene group, a pyrimidinylene group, a quinolinylene group, an isoquinolinylene group, a naphthyridinylene group, a quinoxalinylene group, a quinazolinylene group, a dibenzofuranylene group, and a dibenzothiophenylene group; and a phenylene group, a naphthylene group, a fluorenylene group, a pyridinylene group, a pyrazinylene group, a pyrimidinylene group, a quinolinylene group, an isoquinolinylene group, a naphthyridinylene group, a quinoxalinylene group, a quinazolinylene group, a dibenzofuranylene group, and a dibenzothiophenylene group, each substituted with at least one selected from a deuterium, —F, —Cl, —Br, —I, a methyl group, an ethyl group, an n-propyl group, an iso-propyl group, an n-butyl group, an iso-butyl group, a sec-butyl group, a tert-butyl group, a phenyl group, and a pyridinyl group, but is not limited thereto.

In some embodiments, $Y_2$ in Formula 1 may be selected from a phenylene group, a pyridinylene group, a quinolinylene group, an isoquinolinylene group, a dibenzofuranylene group, and a dibenzothiophenylene group; and a phenylene group, a pyridinylene group, a quinolinylene group, an isoquinolinylene group, a dibenzofuranylene group and a dibenzothiophenylene group, each substituted with at least one selected from a deuterium, a methyl group, a tert-butyl group, and a phenyl group, but is not limited thereto.

In some embodiments, $Y_2$ in Formula 1 may be selected from Formulae 3-1 to 3-17 below, but is not limited thereto:

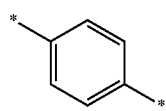
3-1

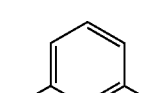
3-2

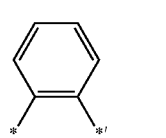
3-3

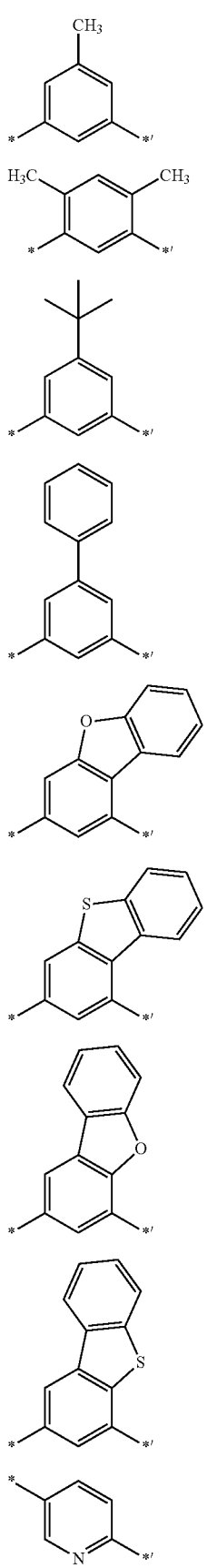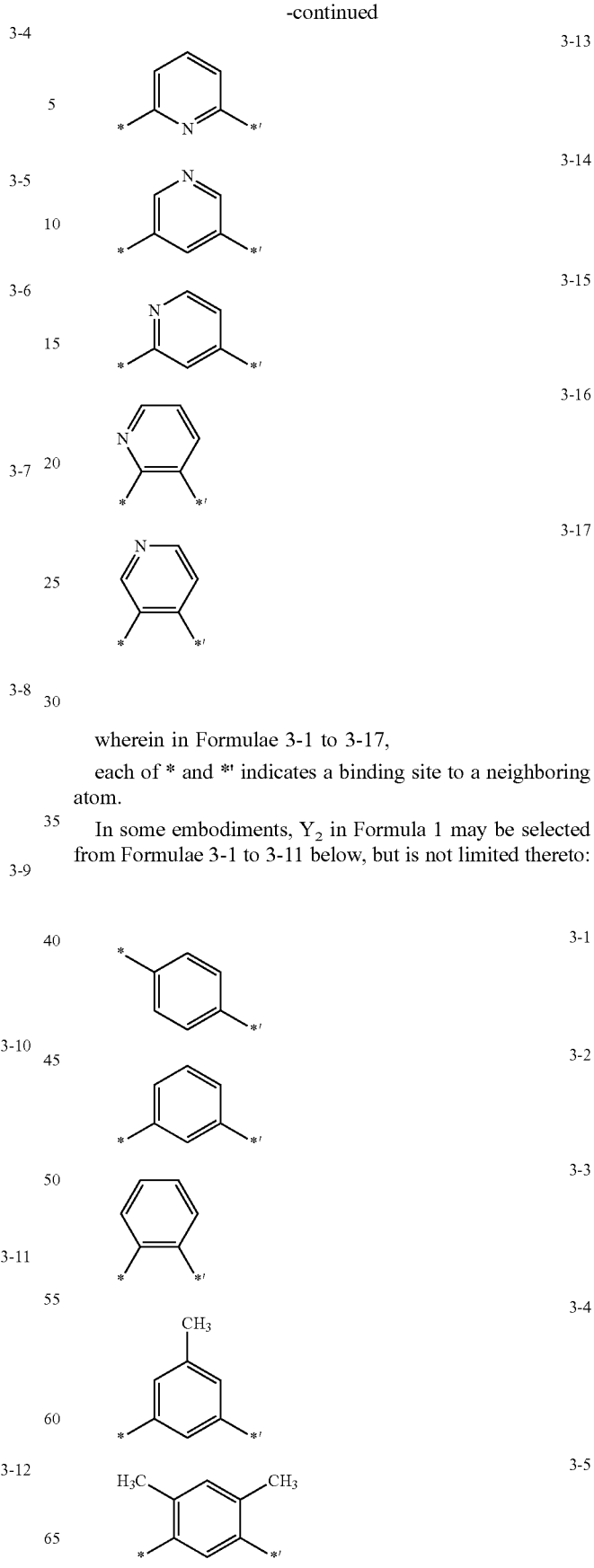
wherein in Formulae 3-1 to 3-17,
each of * and *' indicates a binding site to a neighboring atom.
In some embodiments, $Y_2$ in Formula 1 may be selected from Formulae 3-1 to 3-11 below, but is not limited thereto:

-continued 3-6
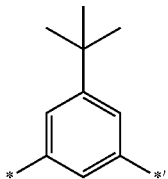

3-7
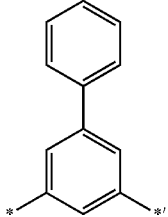

3-8
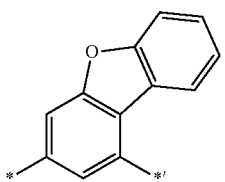

3-9
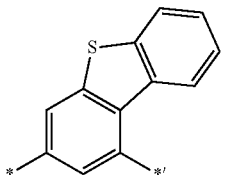

3-10
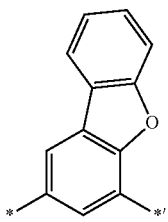

3-11
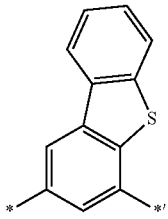

wherein in Formulae 3-1 to 3-11,
each of * and *' indicates a binding site to a neighboring atom.

$L_1$ in Formula 1 may be selected from a monodentate ligand and a bidentate ligand.

For example, $L_1$ in Formula 1 may be a monodentate ligand, but is not limited thereto.

Examples of the monodentate ligand may include an iodide ion, a bromide ion, a chloride ion, a sulfide, a thiocyanate ion, a nitrate ion, an azide ion, a hydroxyl ion, a cyanide ion, an isocyanide ion, water, an acetonitrile, a pyridine, an ammonia, a carbon monoxide, $PPh_3$, $PPh_2CH_3$, $PPh(CH_3)_2$, and $P(CH_3)_3$, but are not limited thereto.

Examples of the bidentate ligand may include a oxalate ion, an acetylacetonate, a picolinic acid, a 2-(2-hydroxyphenyl)-pyridine, a 2-phenylpyridine, a 1,2-bis(diphenylphosphino)ethane (dppe), a 1,1-bis(diphenylphosphino)methane (dppm), a glycinate, a ethylenediamine, a 2,2'-bipyridine, and a 1,10-phenanthroline, but are not limited thereto.

a1 in Formula 1 refers to the number of $L_1$ and may be selected from 0, 1, and 2. When a1 is 2, two of $L_1$ may be identical to or different from each other. When a1 is 0, $L_1$ is absent.

For example, a1 in Formula 1 may be 0, but is not limited thereto.

In some embodiments, a1 in Formula 1 may be 2, but is not limited thereto.

For example, in Formula 1, $L_1$ may be a monodentate ligand, and a1 may be 2. However the present inventive concept is not limited thereto.

For example, in Formula 1, $L_1$ may be a bidentate ligand, and a1 may be 1. However the present inventive concept is not limited thereto.

$R_1$ to $R_4$ In Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic hetero-condensed polycyclic group, —C(=O)($Q_1$), —Si($Q_1$)($Q_2$)($Q_3$), and —N($Q_1$)($Q_2$); wherein $R_1$ and $R_4$ or $R_2$ and $R_3$ may be optionally linked to form a saturated or unsaturated ring;

$Q_1$ to $Q_3$ may be each independently selected from a $C_1$-$C_{60}$ alkyl group and a $C_6$-$C_{60}$ aryl group;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted a monovalent non-aromatic condensed polycyclic group, and the substituted monovalent non-aromatic hetero-condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group;

For example, $R_1$ to $R_4$ in Formula 1 may be each independently selected from a hydrogen, a deuterium, —F, —Cl, —Br, —I, a methyl group, an ethyl group, an n-propyl group, an iso-propyl group, an n-butyl group, an iso-butyl group, a sec-butyl group, a tert-butyl group, —$CF_3$, a methoxy group, an ethoxy group, a tert-butoxy group, a phenyl group, —C(=O)($Q_1$), —Si($Q_1$)($Q_2$)($Q_3$), and —N($Q_1$)($Q_2$); and a phenyl group substituted with a methyl group; wherein $R_1$ and $R_4$ or $R_2$ and $R_3$ may be optionally linked to form a saturated or unsaturated ring;

$Q_1$ to $Q_3$ may be each independently selected from a methyl group, an ethyl group, an n-propyl group, an iso-propyl group, an n-butyl group, an iso-butyl group, a sec-butyl group, a tert-butyl group, and a phenyl group, but are not limited thereto.

In some embodiments, $R_1$ to $R_4$ in Formula 1 may be each independently selected from a hydrogen, a deuterium, —F, a methyl group, an ethyl group, an n-propyl group, an iso-propyl group, an iso-butyl group, a sec-butyl group, a tert-butyl group, —$CF_3$, a methoxy group, a tert-butoxy group, a phenyl group, —C(=O)($CH_3$), —Si($CH_3$)$_3$, —N($CH_3$)$_2$, —N(Ph)$_2$, and a group represented by Formula 4-1 below; wherein $R_1$ and $R_4$ or $R_2$ and $R_3$ may be optionally linked to form a saturated or unsaturated ring, but are not limited thereto:

Formula 4-1

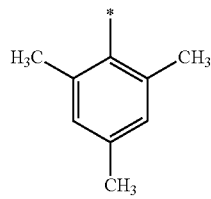

4-1 wherein in Formula 4-1,
* indicates a binding site to a neighboring atom.

In some embodiments, in Formula 1, $R_1$ to $R_4$ may be each independently selected from a hydrogen, a methyl group, an ethyl group, an iso-propyl group, an iso-butyl group, a sec-butyl group, a tert-butyl group, —$CF_3$, a phenyl group, —Si($CH_3$)$_3$, and a group represented by Formula 4-1 below, but are not limited thereto:

Formula 4-1

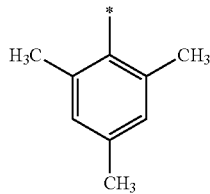

4-1 wherein in Formula 4-1,
* indicates a binding site to a neighboring atom.

b1 in Formula 1 indicates the number of groups $R_1$ and may be selected from 1, 2, 3, and 4. When b1 is 2 or greater, groups $R_1$ may be identical or different.

b2 in Formula 1 indicates the number of groups $R_2$ and may be selected from 1, 2, 3, and 4. When b2 is 2 or greater, groups $R_2$ may be identical or different.

b3 in Formula 1 indicates the number of groups $R_3$ and may be selected from 1, 2, 3, and 4. When b3 is 2 or greater, groups $R_3$ may be identical or different.

b4 in Formula 1 indicates the number of groups $R_4$ and may be selected from 1, 2, 3, and 4. When b4 is 2 or greater, groups $R_4$ may be identical or different.

For example, the organometallic compound may be any one selected from Formulae 1-1 to 1-9 below, but is not limited thereto:

Formula 1-1

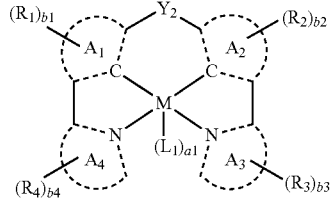

Formula 1-2

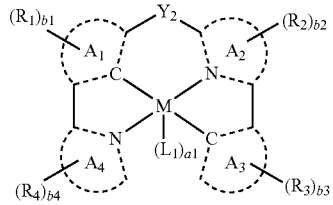

Formula 1-3

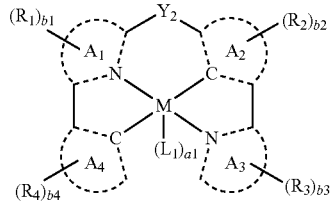

Formula 1-4

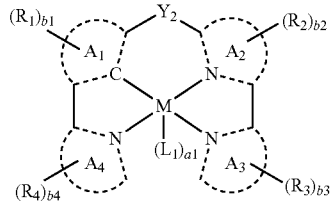

Formula 1-5
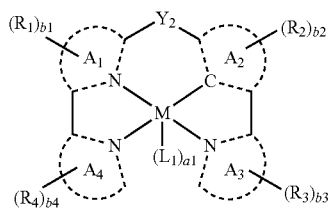
Formula 1-6
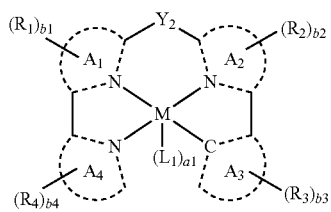
Formula 1-7
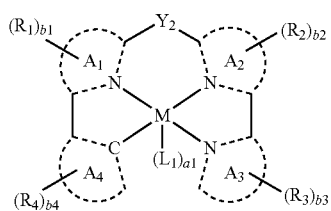
Formula 1-8
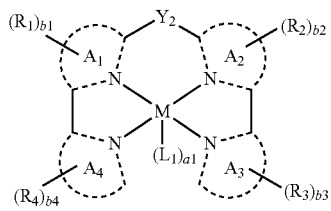
Formula 1-9
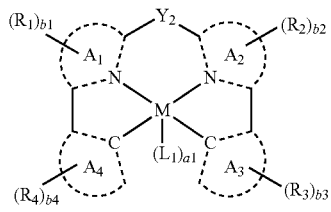
wherein in Formulae 1-1 to 1-9,
M, $A_1$ to $A_4$, $Y_2$, $L_1$, a1, $R_1$ to $R_4$ and b1 to b4 in Formulae 1-1 to 1-9 may be the same as in Formula 1.
In some embodiments, the organometallic compound may be one selected from Formulae 1-1 to 1-9 below, but is not limited thereto:
Formula 1-1
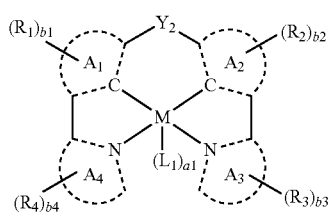
Formula 1-2
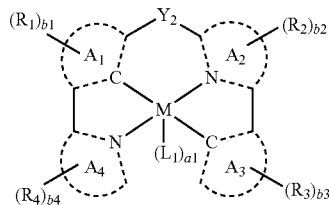
Formula 1-3
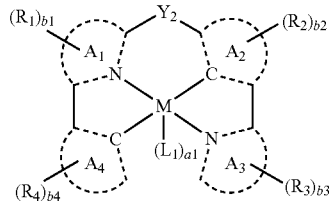
Formula 1-4
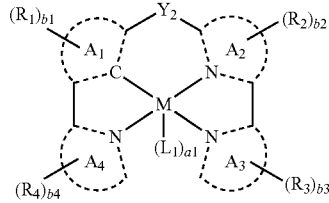
Formula 1-5
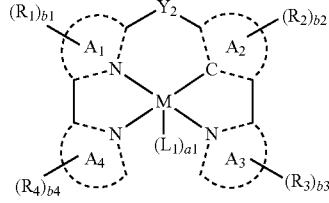
Formula 1-6
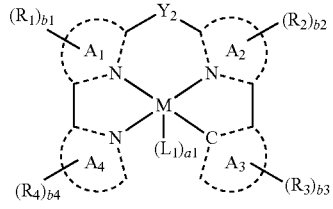
Formula 1-7
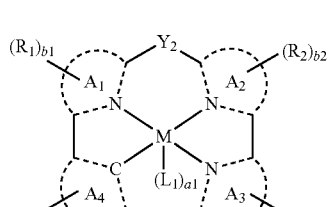
Formula 1-8
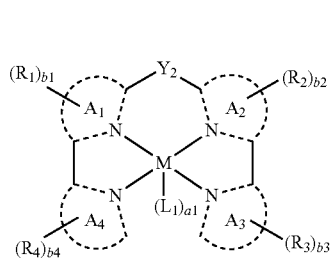

-continued

Formula 1-9 wherein in Formulae 1-1 to 1-8,

M may be selected from osmium(Os), iridium(Ir), and platinum(Pt);

$A_1$ ring to $A_4$ ring may be each independently selected from a benzene, a pyrazole, an indazole, a tetrahydroindazole, a pyridine, a quinoline, an isoquinoline, and a dibenzofuran;

$Y_2$ may be selected from Formulae 3-1 to 3-17 below:

3-1

3-2

3-3

3-4

3-5

3-6

3-7

3-8

3-9

3-10

3-11

3-12

3-13

3-14

3-15

3-16

3-17 wherein in Formulae 3-1 to 3-17, each of * and *' indicates a binding site to a neighboring atom;

$R_1$ to $R_4$ may be each independently selected from a hydrogen, a methyl group, an ethyl group, an iso-propyl group, an iso-butyl group, a sec-butyl group, a tert-butyl group, —$CF_3$, a phenyl group, —$Si(CH_3)_3$, and a group represented by Formula 4-1 below;

Formula 4-1

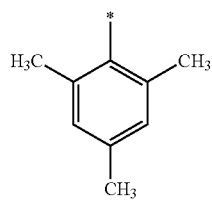

wherein in Formula 4-1,

* indicates a binding site to a neighboring atom.

b1 to b4 may be each independently selected from 1, 2, 3, and 4.

In some embodiments, the organometallic compound may be any one selected from Formulae 1-1a to 1-6a below, but is not limited thereto:

Formula 1-1a

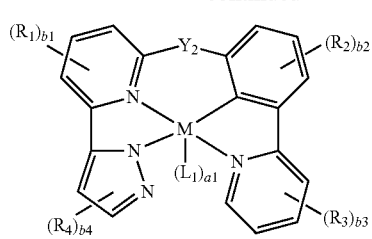

Formula 1-2a

Formula 1-3a

Formula 1-4a

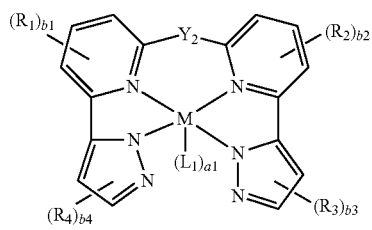

Formula 1-5a

Formula 1-6a wherein in Formulae 1-1a to 1-6a,

M, $Y_2$, $L_1$, a1, $R_1$ to $R_4$, and b1 to b4 herein may be the same as in Formula 1.

In some embodiments, the organometallic compound may be any one selected from Compounds 1 to 29 below, but is not limited thereto:

1

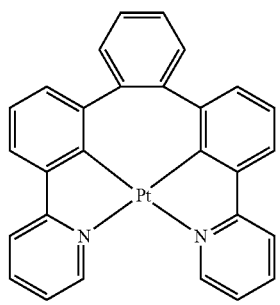

2

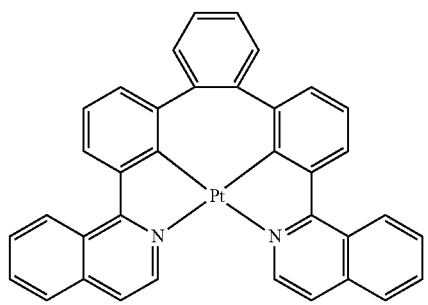

3

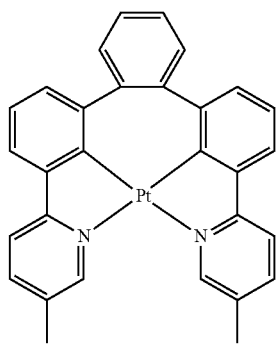

4
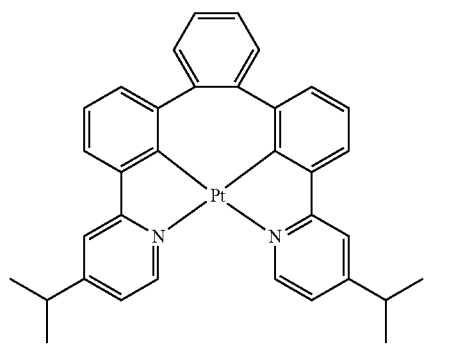
5
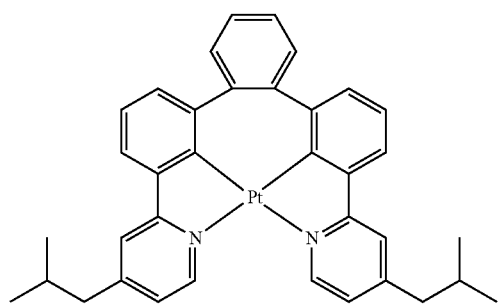
6
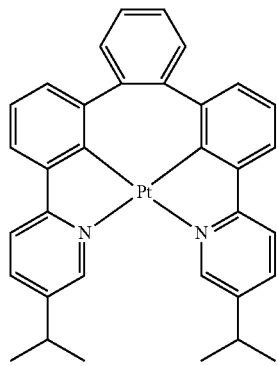
7
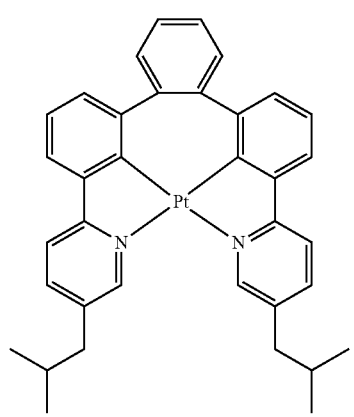
8
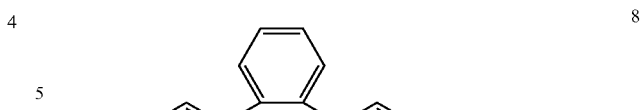
9
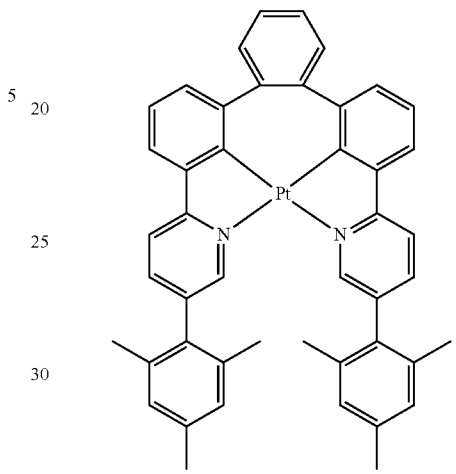
10
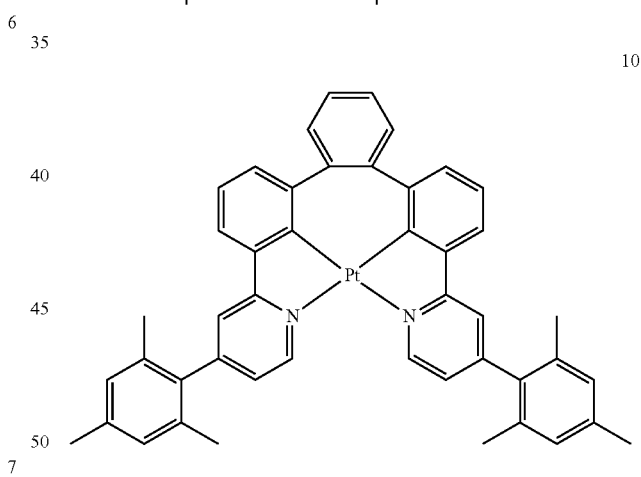
11
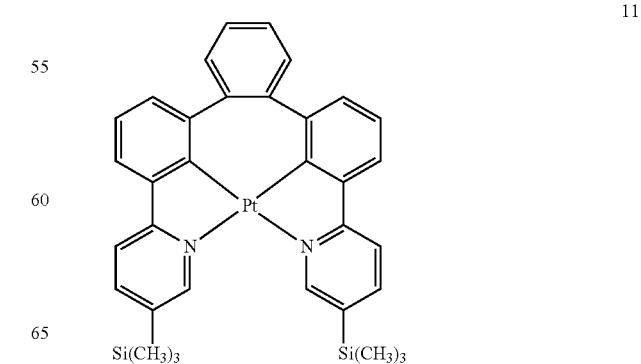

12
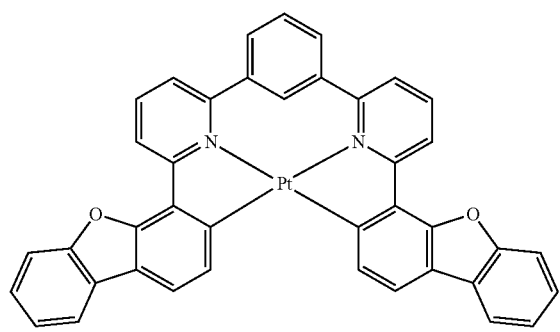
13
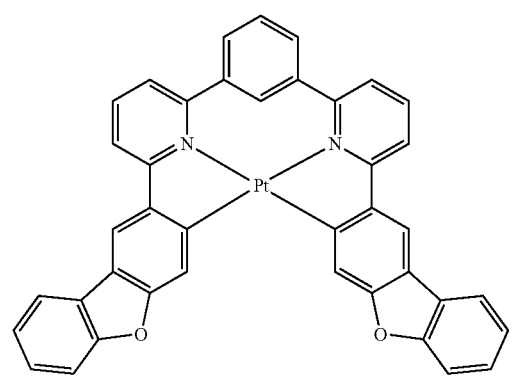
14
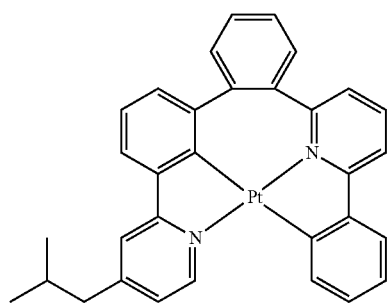
15
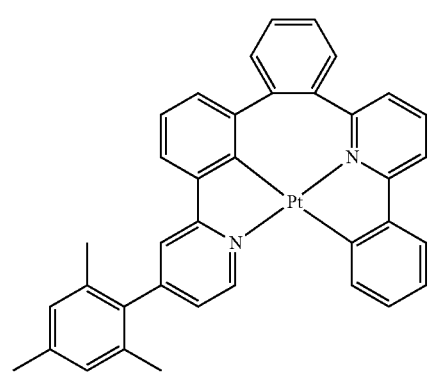
16
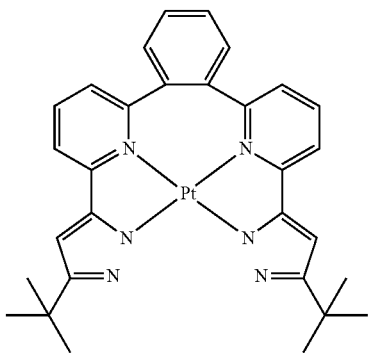
17
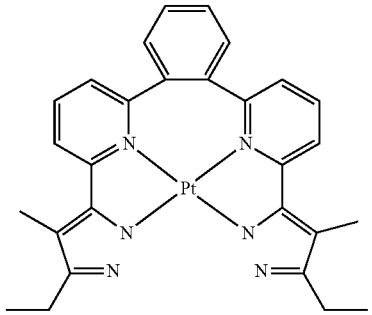
18
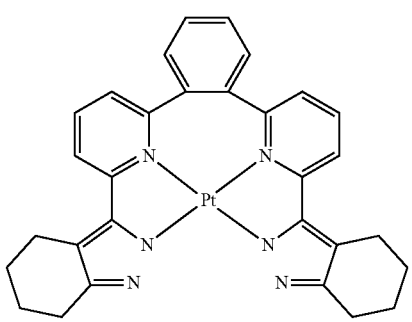
19
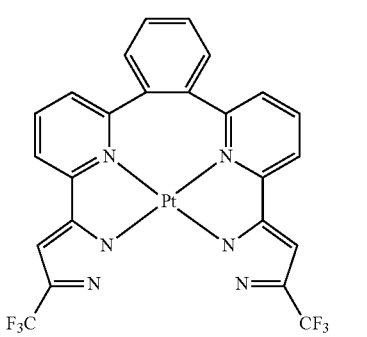
20
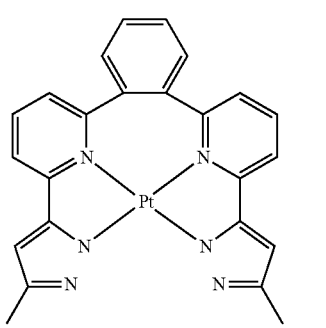

21
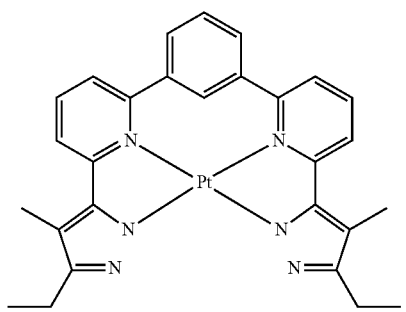
22
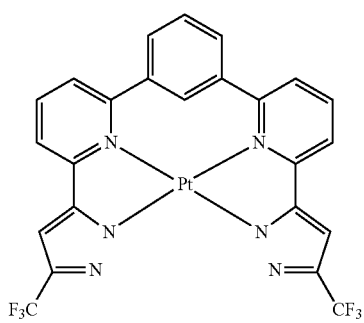
23
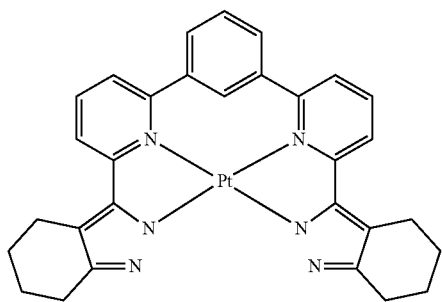
24
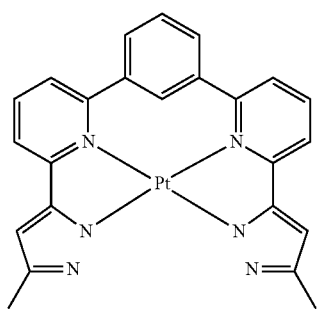
25
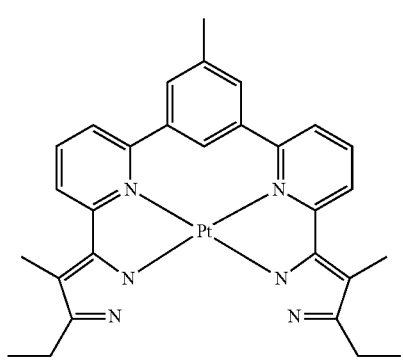
26
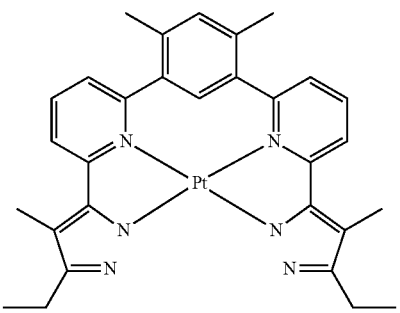
27
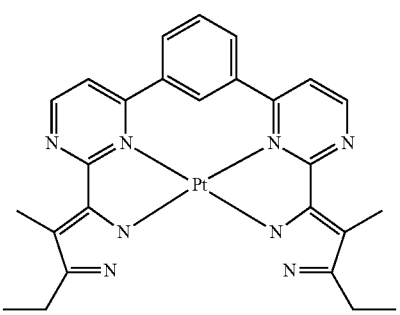
28
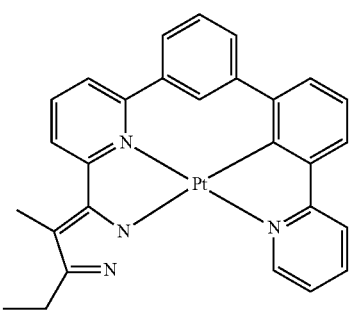
29
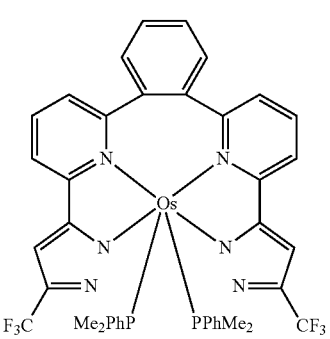
The organometallic compound represented by Formula 1 has a tetradentate structure as illustrated in Formula 1'-1 below.

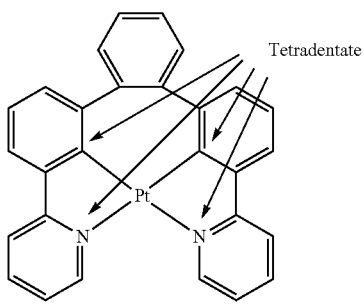

Formula 1'-1

Tetradentate

The organometallic compound represented by Formula 1 has a tetradentate structure, and thus has excellent thermal and electric stability. Accordingly, an organic light-emitting device including the organometallic compound represented by Formula 1 has long lifespan characteristics.

The organometallic compound represented by Formula 1, as illustrated in Formula 1'-2 below, has a divalent linking group selected from an arylene group or the like. In other words, the divalent linking group (shown inside the dotted square) in Formula 1'-2 below is not a single bond or an alkylene group.

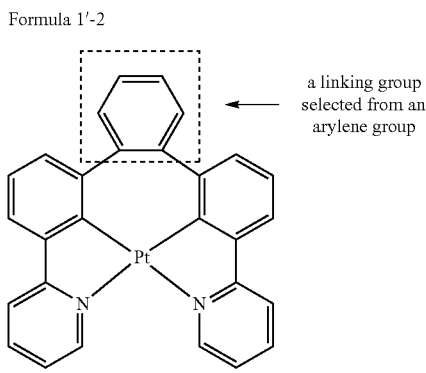

Formula 1'-2 a linking group selected from an arylene group

The organometallic compound represented by Formula 1 includes a divalent linking group selected from an arylene group or the like, and thus has a relatively low vibrational energy. Without wishing to be bound by a theory, it is understood that nonradiative transition may relatively rarely occur in the organometallic compound represented by Formula 1, and the organometallic compound may have a high quantum efficiency as a result. Therefore, the organic light-emitting device including the organometallic compound represented by Formula 1 may have high efficiency.

The organometallic compound represented by Formula 1 includes a divalent linking group selected from an electron donating group such as an arylene group, and thus the HOMO energy level of the organometallic compound represented by Formula 1 may be increased. In this regard, the organic light-emitting device including the organometallic compound represented by Formula 1 may have low driving voltage characteristics, and since holes are not accumulated in a transport layer, the device may also have high efficiency and a long lifespan.

Therefore, the organic light-emitting device including the organometallic compound represented by Formula 1 may have a low driving voltage, high efficiency, and a long lifespan.

Synthesis methods to prepare the organometallic compound represented by Formula 1 are known in the art and may be apparent to one of ordinary skill in the art by referring to Synthesis Examples provided below.

The organometallic compound represented by Formula 1 may be suitable for use as an organic layer in an organic light-emitting device, for example, as a dopant of an emission layer as one of the organic layers. In some embodiments, provided is an organic light-emitting device including:

a first electrode;
a second electrode; and
an organic layer disposed between the first electrode and the second electrode, wherein the organic layer includes an emission layer and at least one selected from the organometallic compounds represented by Formula 1.

The organic light-emitting device may have, due to the inclusion of an organic layer including the organometallic compound represented by Formula 1, low driving voltage, high efficiency, high brightness, and long lifespan.

The organometallic compound of Formula 1 may be used between a pair of electrodes of an organic light-emitting device. For example, the organometallic compound represented by Formula 1 may be included in the emission layer. In this regard, the organometallic compound may be a dopant, and the emission layer may further include a host (that is, an amount of the organometallic compound represented by Formula 1 is smaller than an amount of the host).

The expression "(an organic layer) includes at least one organometallic compound" used herein may include a case in which "(an organic layer) includes identical organometallic compounds of Formula 1 and a case in which (an organic layer) includes two or more different organometallic compounds of Formula 1.

For example, the organic layer may include, as the organometallic compound, only Compound 1. In this regard, Compound 1 may be situated in an emission layer of the organic light-emitting device. In some embodiments, the organic layer may include, as the organometallic compound, Compound 1 and Compound 2. In this regard, Compound 1 and Compound 2 may be situated in the same layer (for example, Compound 1 and Compound 2 all both be situated in an emission layer).

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode is an anode, and the second electrode is a cathode, and the organic layer includes i) a hole transport region that is disposed between the first electrode and the emission layer, wherein the hole transport region includes at least one of a hole injection layer, a hole transport layer, and an electron blocking layer, and ii) an electron transport region that is disposed between the emission layer and the second electrode, wherein the electron transport region includes at least one selected from a hole blocking layer, an electron transport layer, and an electron injection layer.

The term "organic layer" used herein refers to a single layer and/or a plurality of layers disposed between the first electrode and the second electrode of an organic light-emitting device. The "organic layer" may include, in addition to an organic compound, an organometallic complex including a metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

In FIG. 1, a substrate may be additionally disposed under the first electrode 11 or above the second electrode 19. For use as the substrate, any suitable substrate that is used in general organic light-emitting devices may be used. The substrate may be a glass substrate or transparent plastic substrate, each with excellent mechanical strength, thermal stability, transparency, surface smoothness, ease of handling, and water-proofness.

The first electrode 11 may be formed by depositing or sputtering a material for forming the first electrode on the substrate. The first electrode 11 may be an anode. The material for the first electrode 11 may be selected from materials with a high work function to allow holes to be easily provided. The first electrode 11 may be a reflective electrode or a transmissive electrode. The material for the first electrode 11 may be an indium tin oxide (ITO), indium zinc oxide (IZO), tin oxide ($SnO_2$), or zinc oxide (ZnO). In some embodiments, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers. For example, the first electrode 11 may have a three-layered structure of ITO/Ag/ITO, but the structure of the first electrode 110 is not limited thereto.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. According to another embodiment, the hole transport region may have a structure of hole injection layer/hole transport layer or hole injection layer/hole transport layer/electron blocking layer, which are sequentially stacked in this stated order from the first electrode 11.

When the hole transport region includes a hole injection layer (HIL), the hole injection layer may be formed on the first electrode 11 by using any one of various methods, for example, vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstrom per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

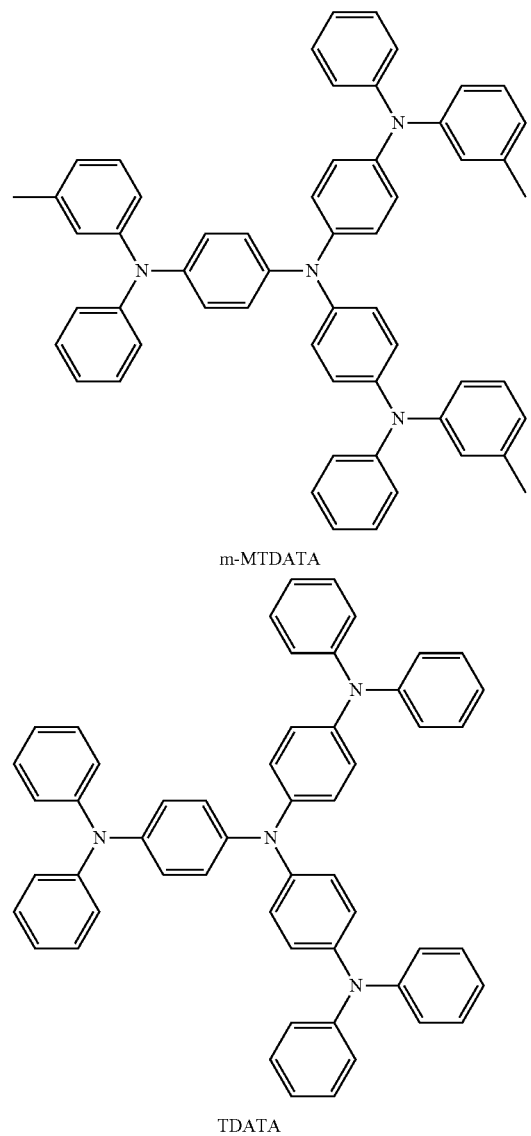

m-MTDATA

TDATA

-continued
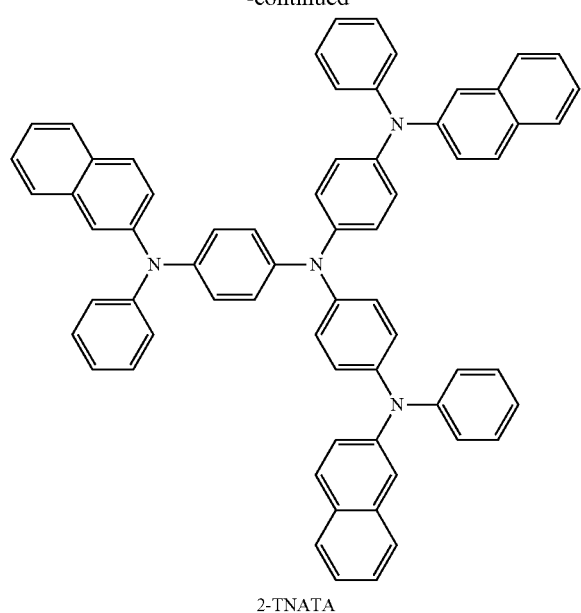
2-TNATA
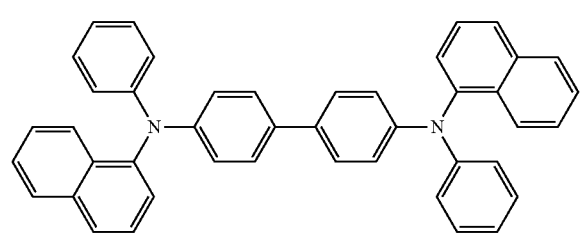
NPB
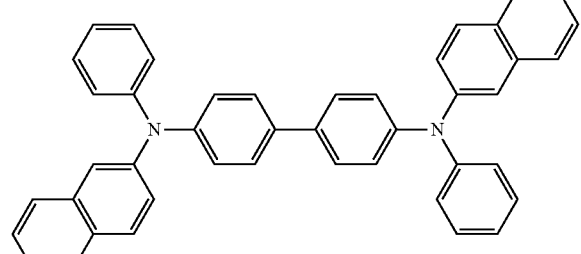
β-NPB
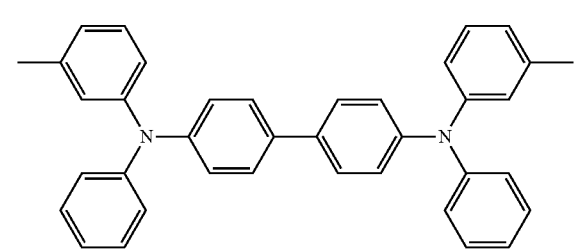
TPD
-continued
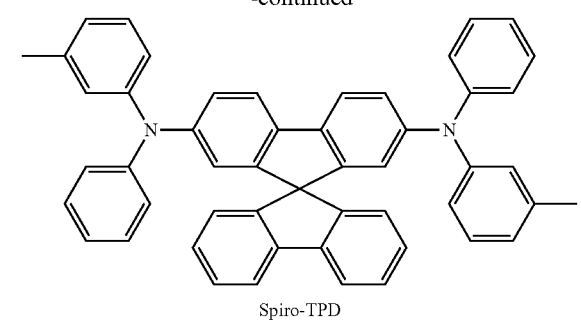
Spiro-TPD
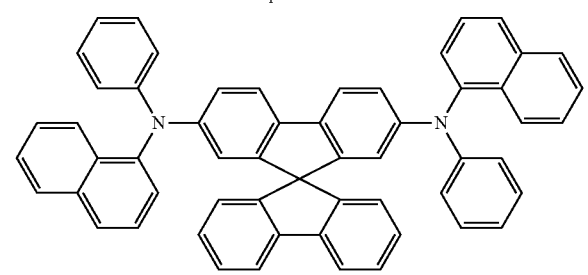
Spiro-NPB
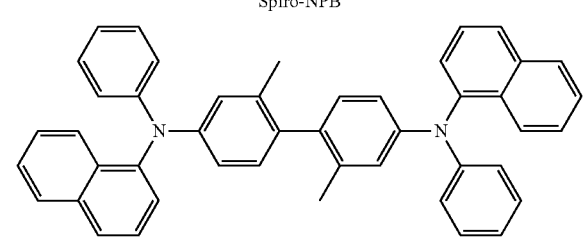
α-NPB
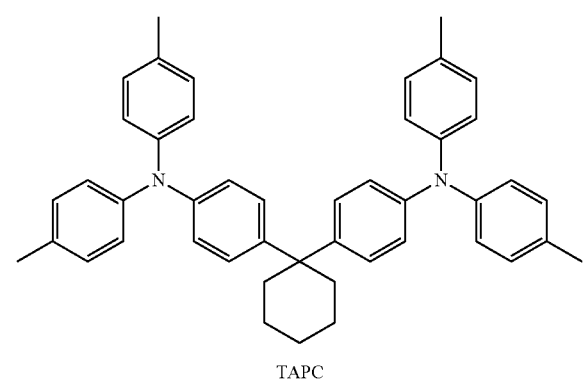
TAPC
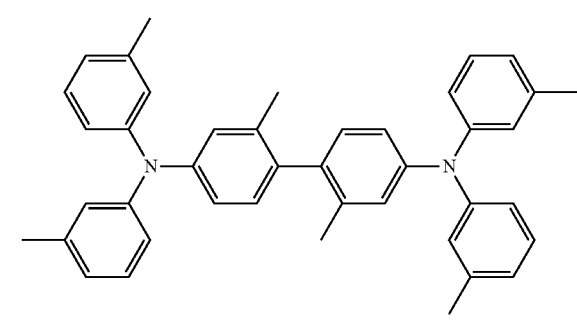
HMTPD Formula 201

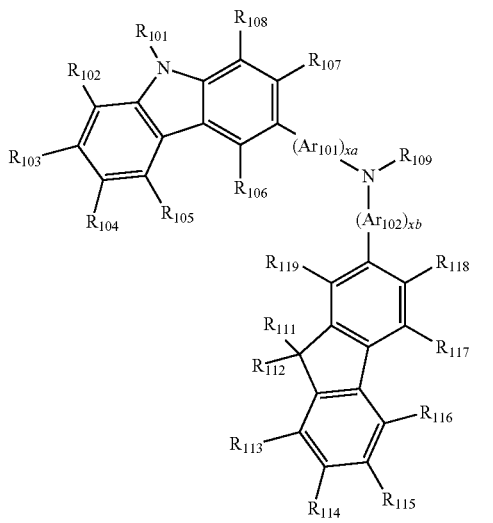

Formula 202

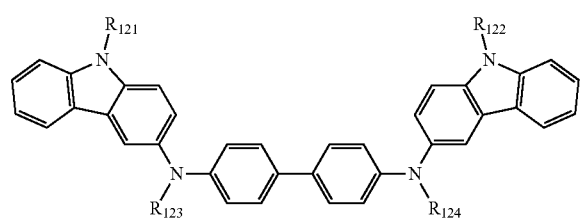

$Ar_{101}$ and $Ar_{102}$ in Formula 201 may be each independently selected from a phenylene, a pentalenylene, an indenylene, a naphthylene, an azulenylene, a heptalenylene, an acenaphthylene, a fluorenylene, a penalenylene, a phenanthrenylene, a anthracenylene, a fluoranthenylene, a triphenylenylene, a pyrenylene, a chrysenylenylene, a naphthacenylene, a picenylene, a perylenylene, and a pentacenylene; and a phenylene, a pentalenylene, an indenylene, a naphthylene, an azulenylene, a heptalenylene, an acenaphthylene, a fluorenylene, a penalenylene, a phenanthrenylene, an anthracenylene, a fluoranthenylene, a triphenylenylene, a pyrenylene, a chrysenylenylene, a naphthacenylene, a picenylene, a perylenylene, and a pentacenylene, each substituted with at least one selected from a deuterium, a halogen atom, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group.

xa and xb in Formula 201 may be each independently an integer of 0 to 5, or 0, 1, or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may be each independently selected from a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{10}$ alkyl (for example, methyl, ethyl, propyl, butyl, pentyl, or hexyl), and a $C_1$-$C_{10}$ alkoxy (for example, methoxy, ethoxy, propoxy, butoxy, or pentoxy);

a $C_1$-$C_{10}$ alkyl group and a $C_1$-$C_{10}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid or a salt thereof, and a phosphoric acid or a salt thereof;

a phenyl, a naphthyl, an anthracenyl, a fluorenyl, and a pyrenyl; and a phenyl, a naphthyl, an anthracenyl, a fluorenyl, and a pyrenyl, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{10}$ alkyl group, and a $C_1$-$C_{10}$ alkoxy group, but they are not limited thereto.

$R_{109}$ in Formula 201 may be one selected from a phenyl, a naphthyl, an anthracenyl, a biphenyl, and a pyridinyl; and a phenyl, a naphthyl, an anthracenyl, a biphenyl, and a pyridinyl, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{20}$ alkyl, and a $C_1$-$C_{20}$ alkoxy.

According to an embodiment, the compound represented by Formula 201 may also be represented by Formula 201A below, but is not limited thereto:

Formula 201A

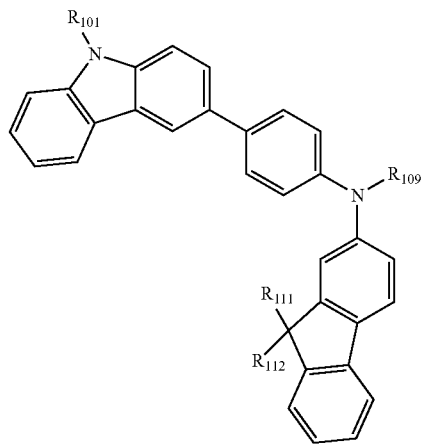

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1
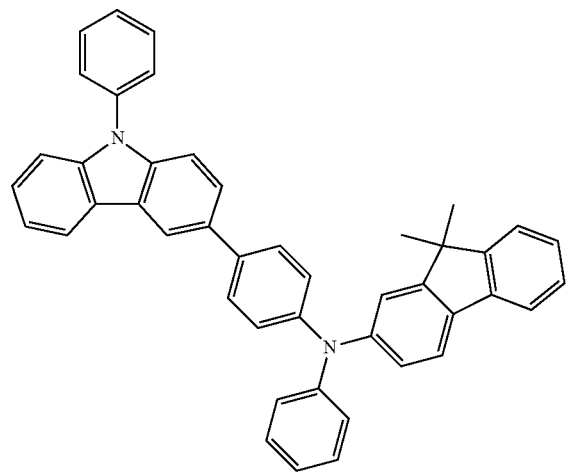
HT3
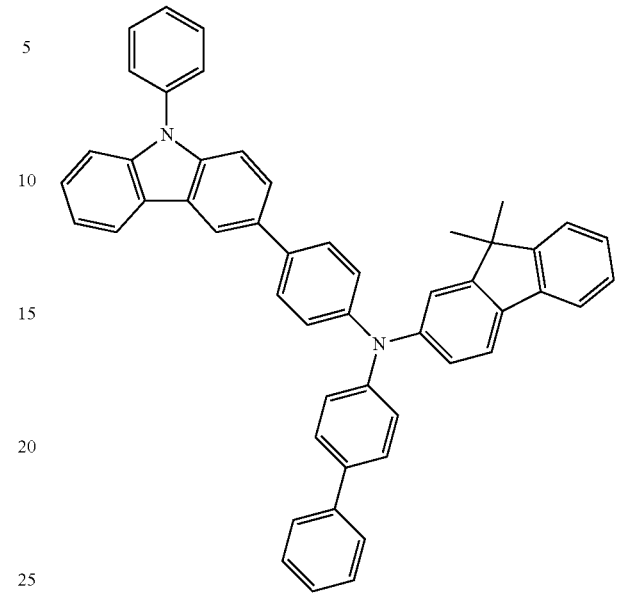
HT2
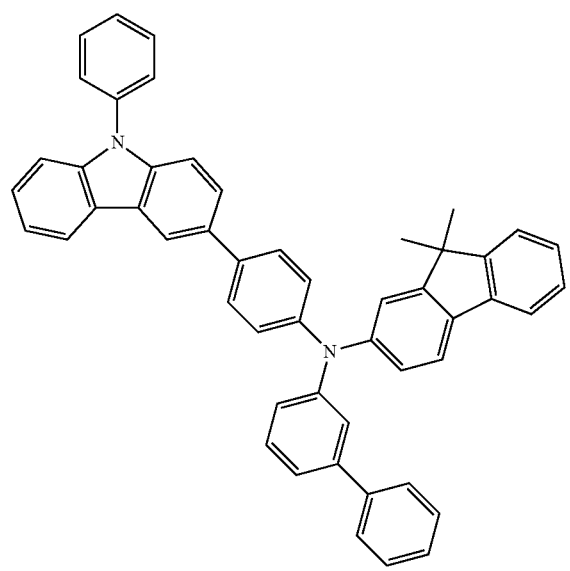
HT4
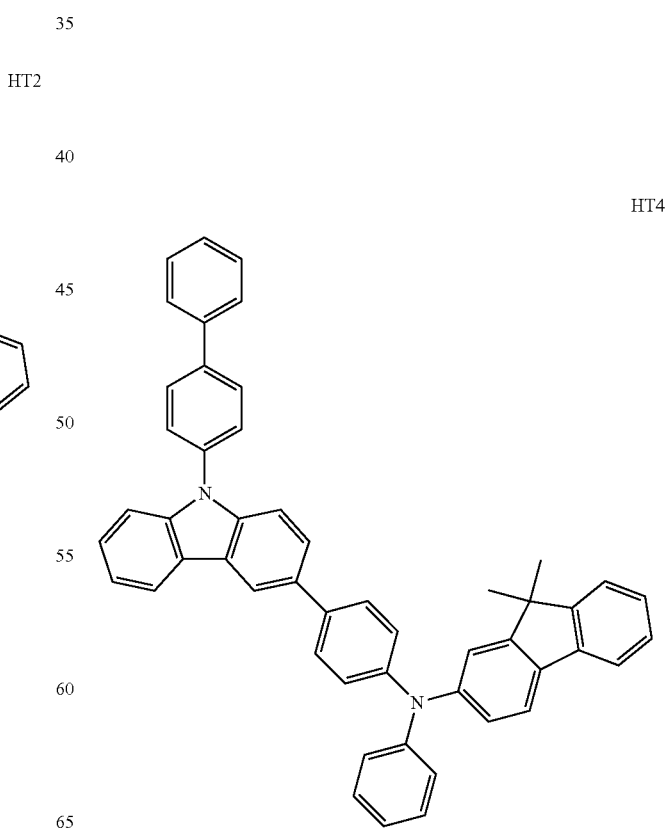

HT5
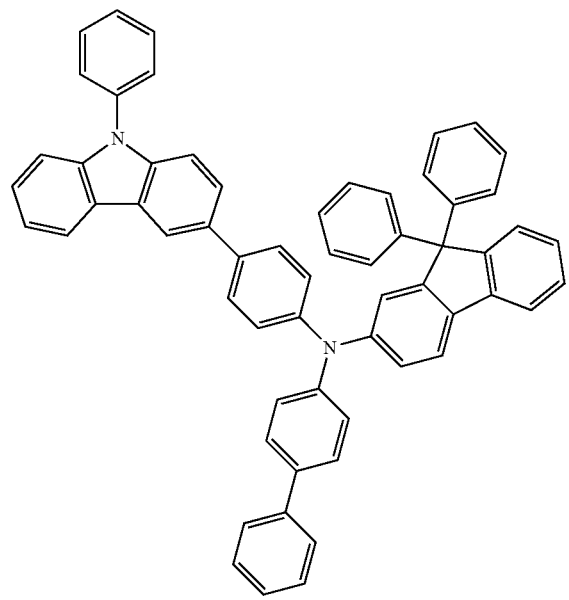
HT7
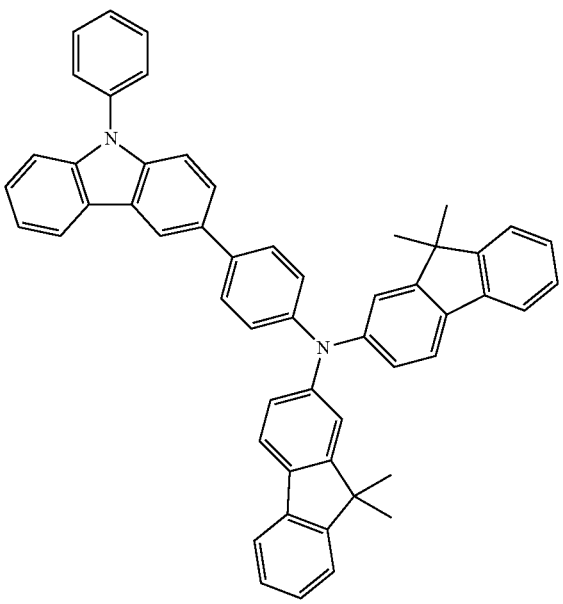
HT6
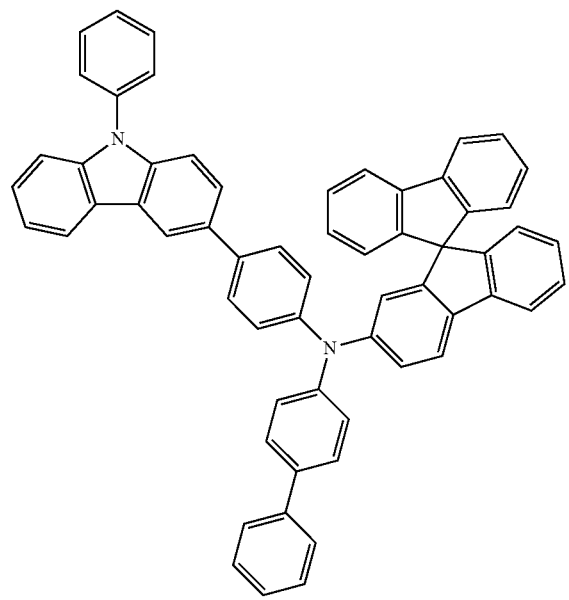
HT8
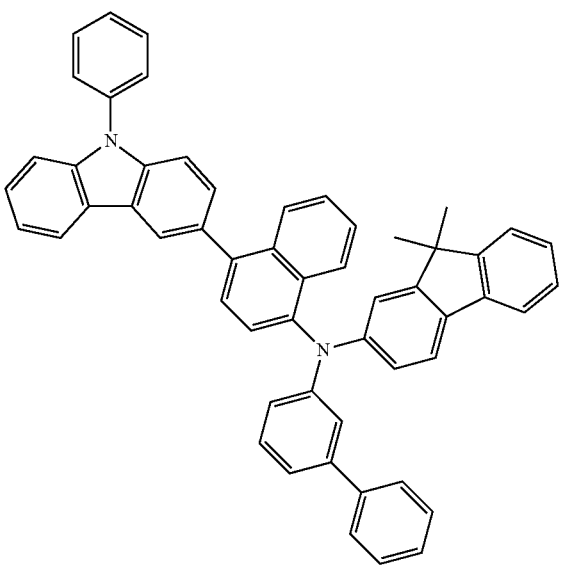

HT9
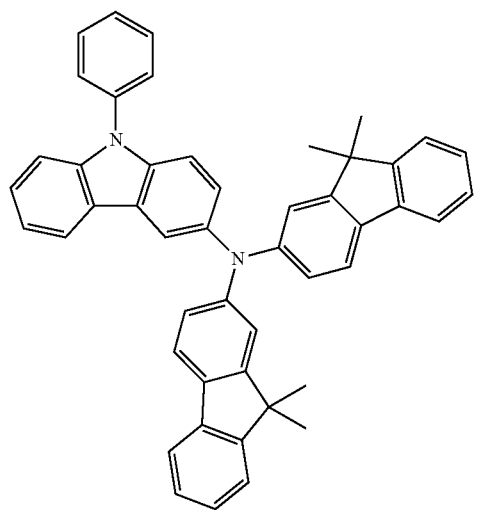
HT11
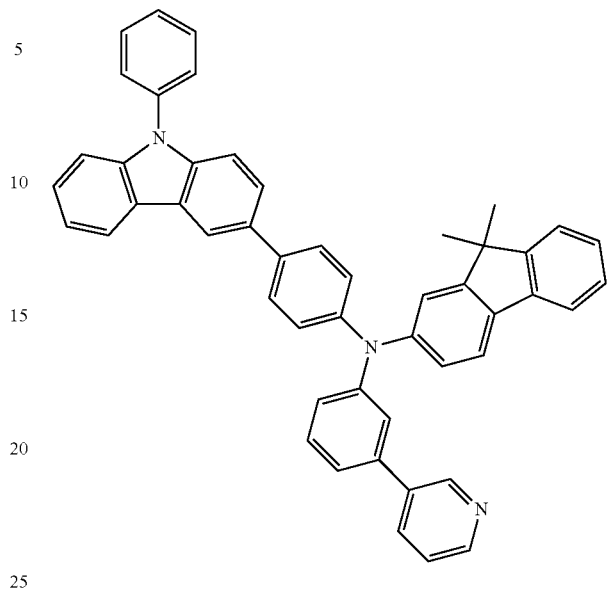
HT10
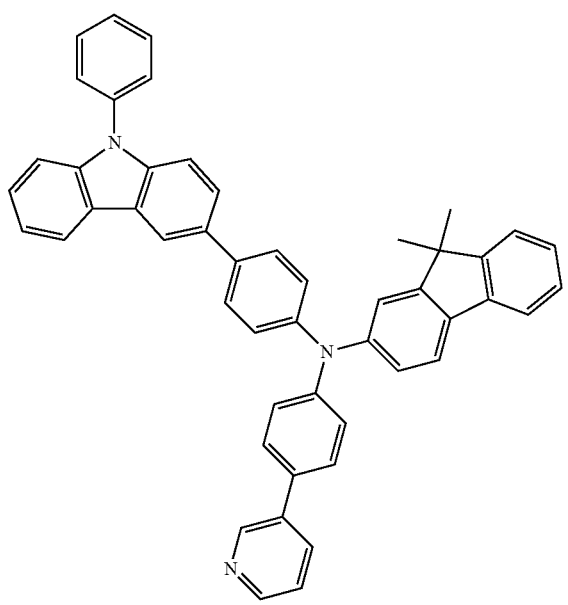
HT12
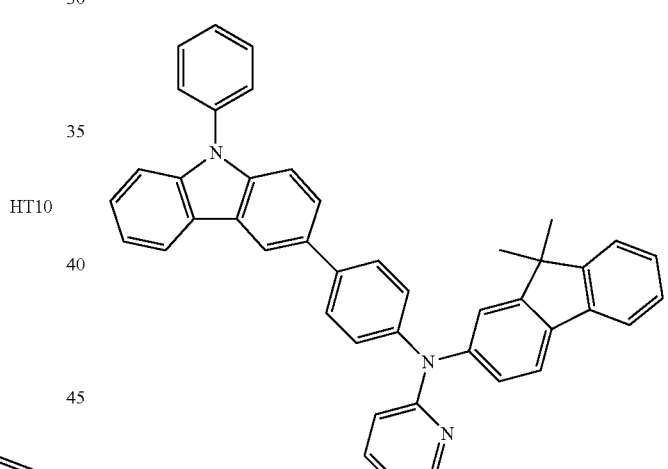
HT13
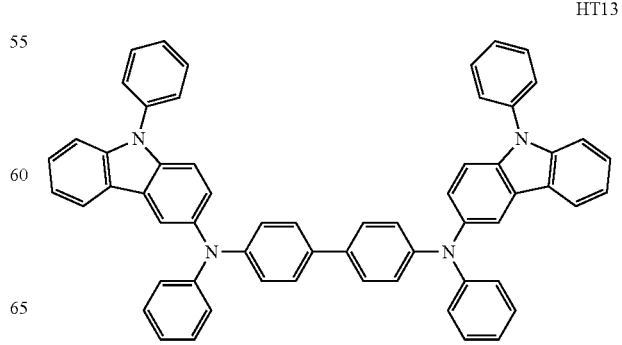

HT14
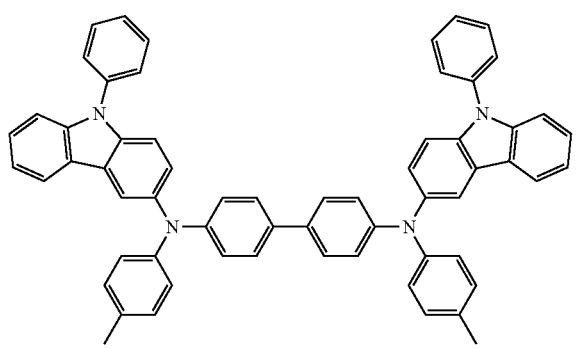

HT15
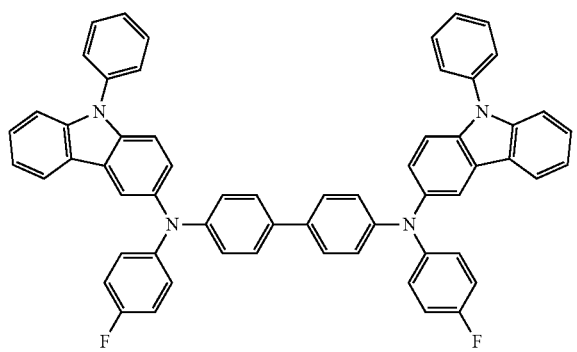

HT16
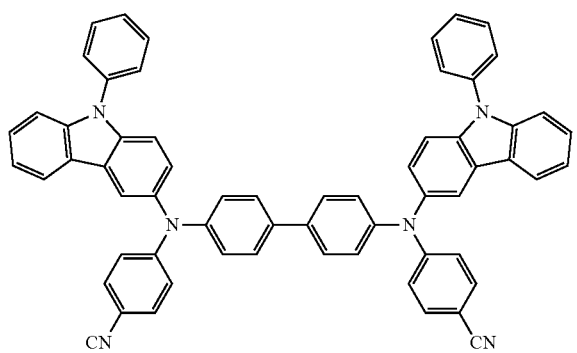

HT17
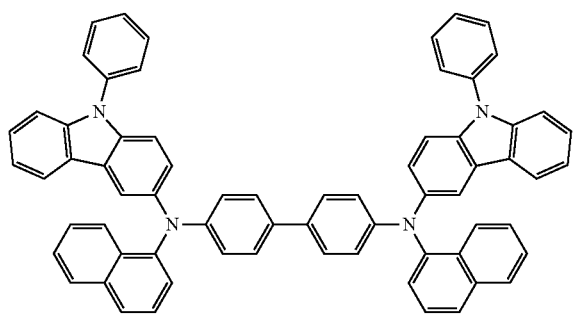

HT18
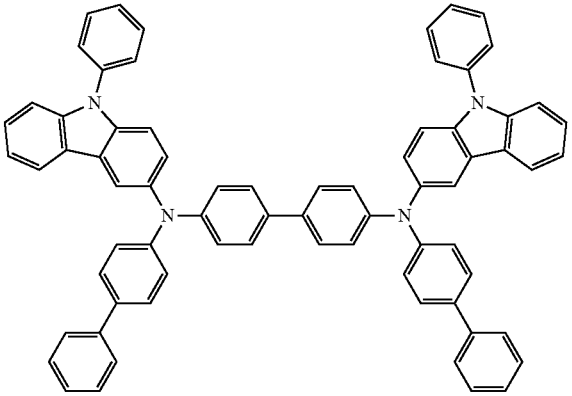

HT19
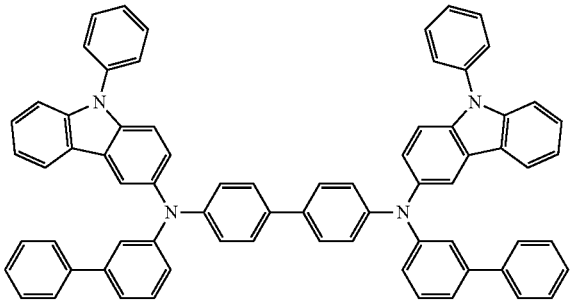

HT20
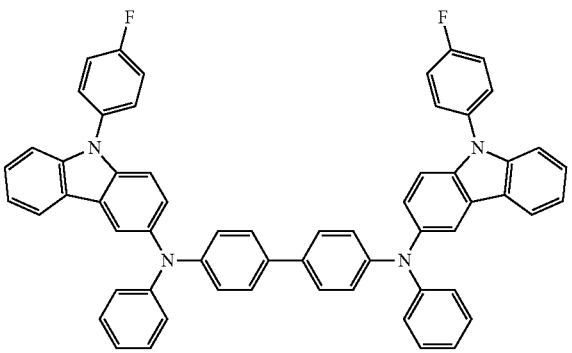

A thickness of the hole transport region may be in a range of about 100 Angstroms (Å) to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant include a quinone derivative, such as tetracyanoquinonedimethane (TCNQ) or 2,3,5,6-tetrafluoro-tetracyano-1, 4-benzoquinonedimethane (F4-TCNQ); a metal oxide, such as a tungsten oxide or a molybdenium oxide; and a cyano group-containing compound, such as Compound HT-D1 below, but are not limited thereto.

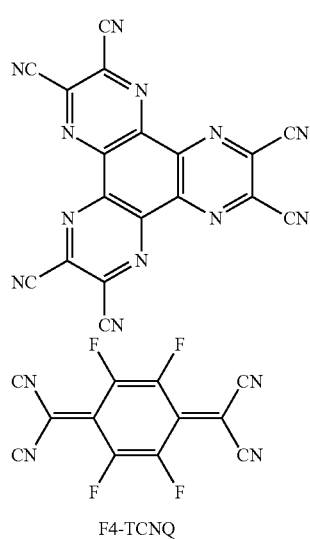

Compound HT-D1

F4-TCNQ

The hole transport region may include a buffer layer.

The buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant, and the dopant may include the organometallic compound represented by Formula 1.

The host may include at least one selected from TPBi, TBADN, ADN (also referred to as "DNA"), CBP, CDBP, and TCP:

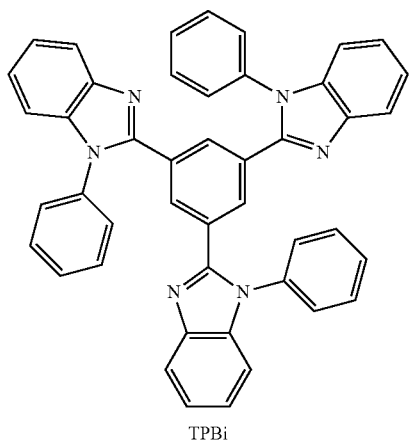

TPBi

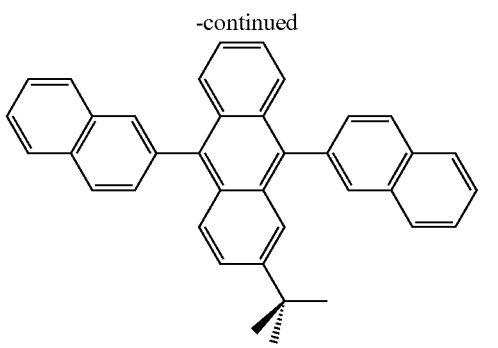

TBADN

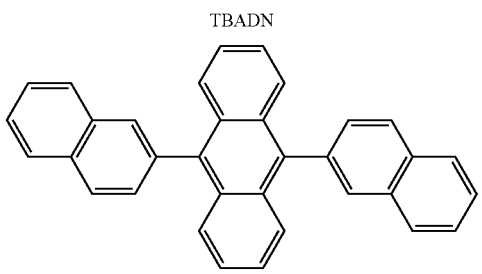

ADN

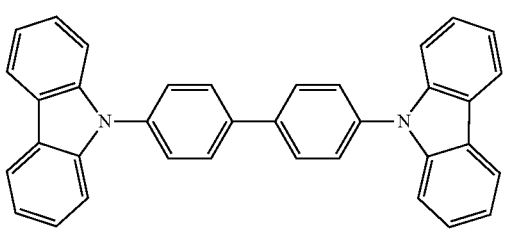

CBP

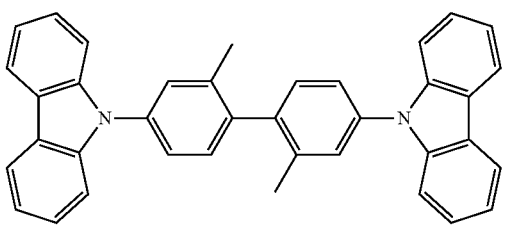

CDBP

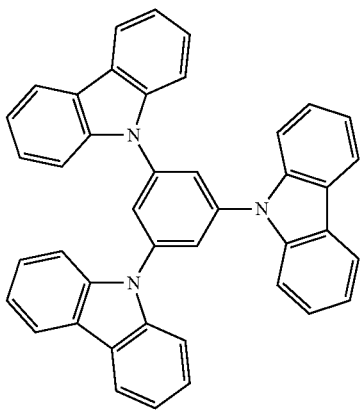

TCP

According to another embodiment, the host may include a compound represented by Formula 301 below.

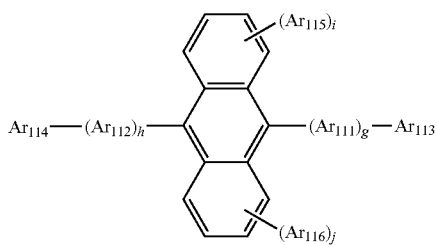

Formula 301

$Ar_{111}$ and $Ar_{112}$ in Formula 301 may be each independently selected from a phenylene, a naphthylene, a phenanthrenylene, and a pyrenylene; and a phenylene, a naphthylene, a phenanthrenylene, a fluorenyl, and a pyrenylene, each substituted with at least one selected from a phenyl, a naphthyl, and an anthracenyl.

$Ar_{113}$ to $Ar_{116}$ in Formula 301 may be each independently selected from a $C_1$-$C_{10}$ alkyl group; a phenyl, a naphthyl, a phenanthrenyl and a pyrenyl; and a phenyl, a naphthyl, a phenanthrenyl, a fluorenyl, and a pyrenyl, each substituted with at least one selected from a phenyl, a naphthyl, and an anthracenyl.

g, h, l, and j in Formula 301 may be each independently an integer of 0 to 4, for example, an integer of 0, 1, or 2.

$Ar_{113}$ and $Ar_{116}$ in Formula 301 may be each independently selected from a $C_1$-$C_{10}$ alkyl group substituted with at least one selected from a phenyl, a naphthyl, and an anthracenyl;

a phenyl, a naphthyl, an anthracenyl, a pyrenyl, a phenanthrenyl, and a fluorenyl;

a phenyl, a naphthyl, an anthracenyl, a pyrenyl, a phenanthrenyl, and a fluorenyl, each substituted with at least one selected from a deuterium, a halogen atom, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl, a naphthyl, an anthracenyl, a pyrenyl, a phenanthrenyl, and a fluorenyl; and

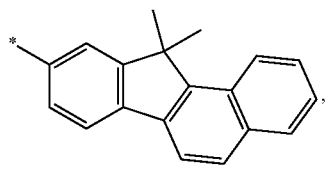 [SMILES: *c1ccc2c(c1)C(C)(C)c1c-2ccc2ccccc12]

but they are not limited thereto.

In some embodiments, the host may include a compound represented by Formula 302 below:

Formula 302

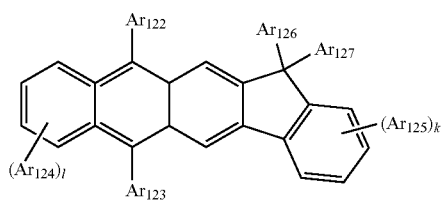

$Ar_{122}$ to $Ar_{125}$ in Formula 302 are the same as described in detail in connection with $Ar_{113}$ in Formula 301.

$Ar_{126}$ and $Ar_{127}$ in Formula 302 may be each independently a $C_1$-$C_{10}$ alkyl group (for example, a methyl group, an ethyl group, or a propyl group).

k and l in Formula 302 may be each independently an integer of 0 to 4. For example, k and l may be 0, 1, or 2.

The compound represented by Formula 301 and the compound represented by Formula 302 may include Compounds H1 to H42 illustrated below, but are not limited thereto.

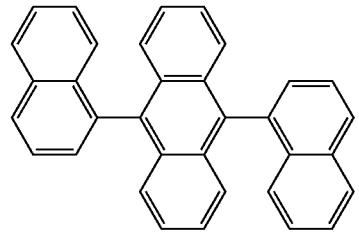

H1

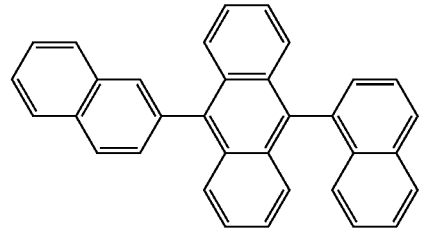

H2

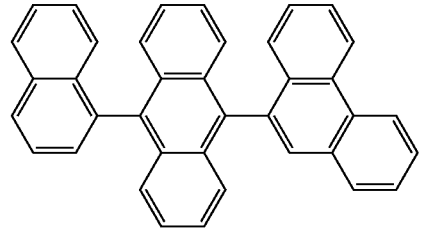

H3

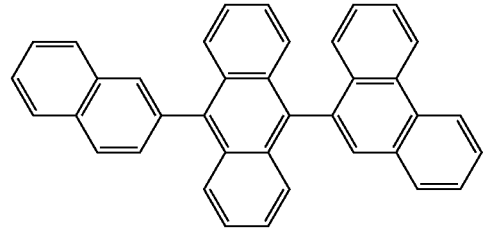

H4

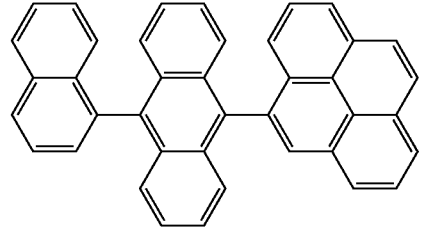

H5

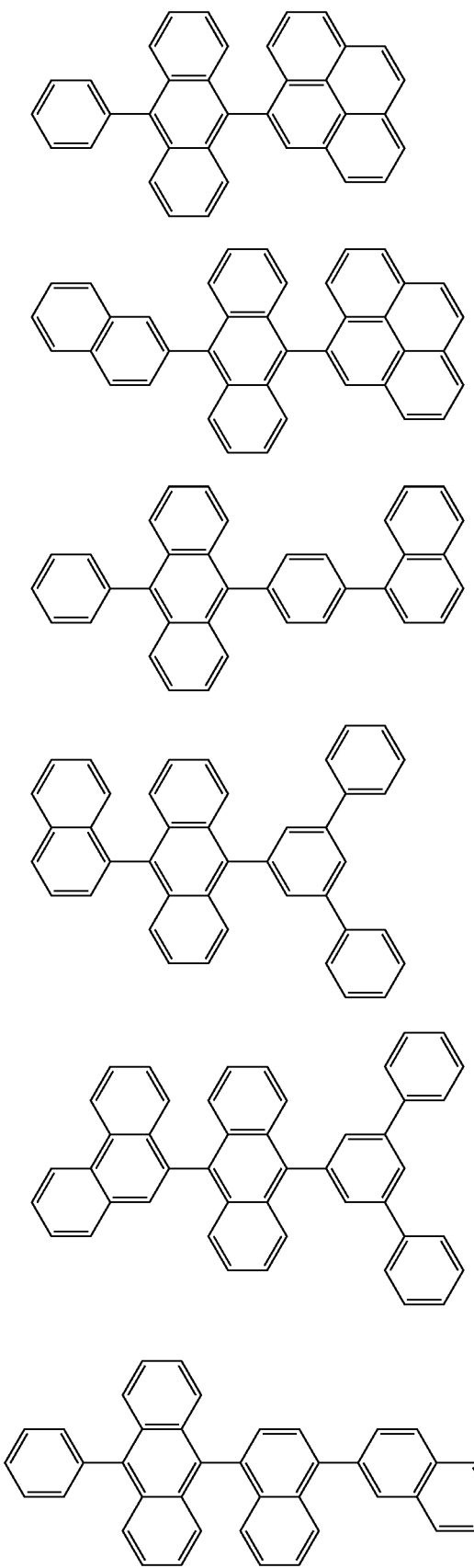
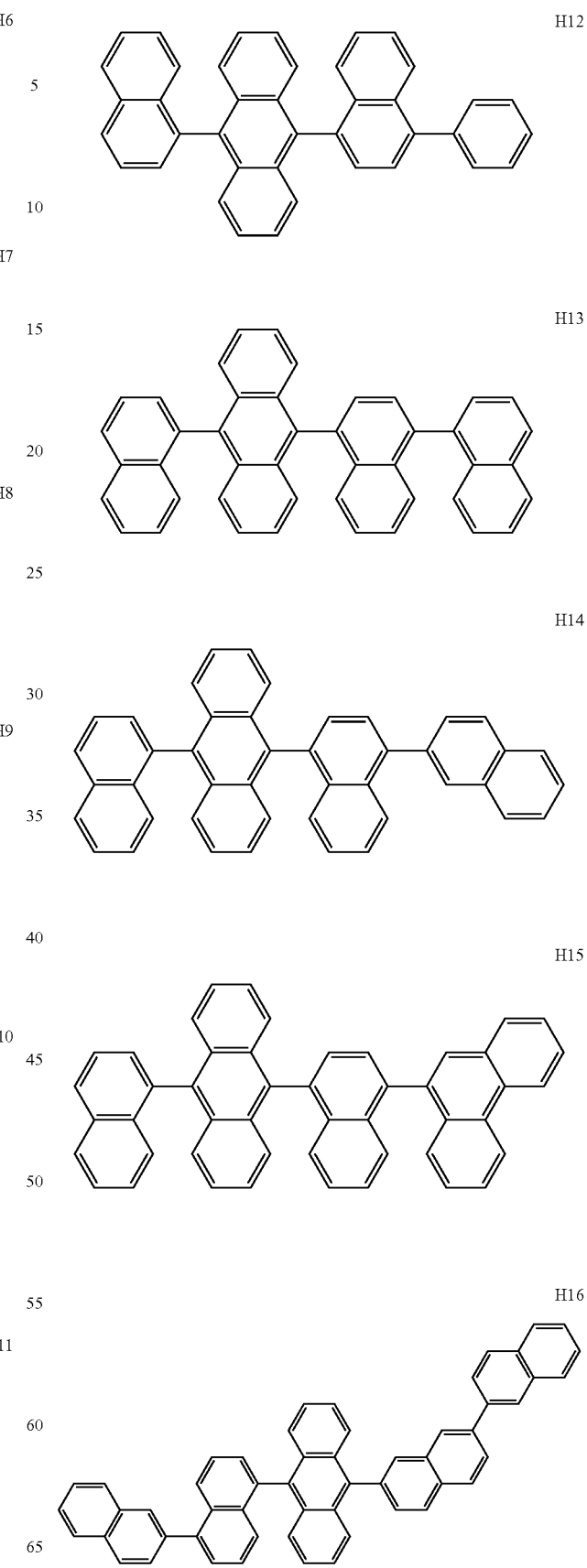

-continued
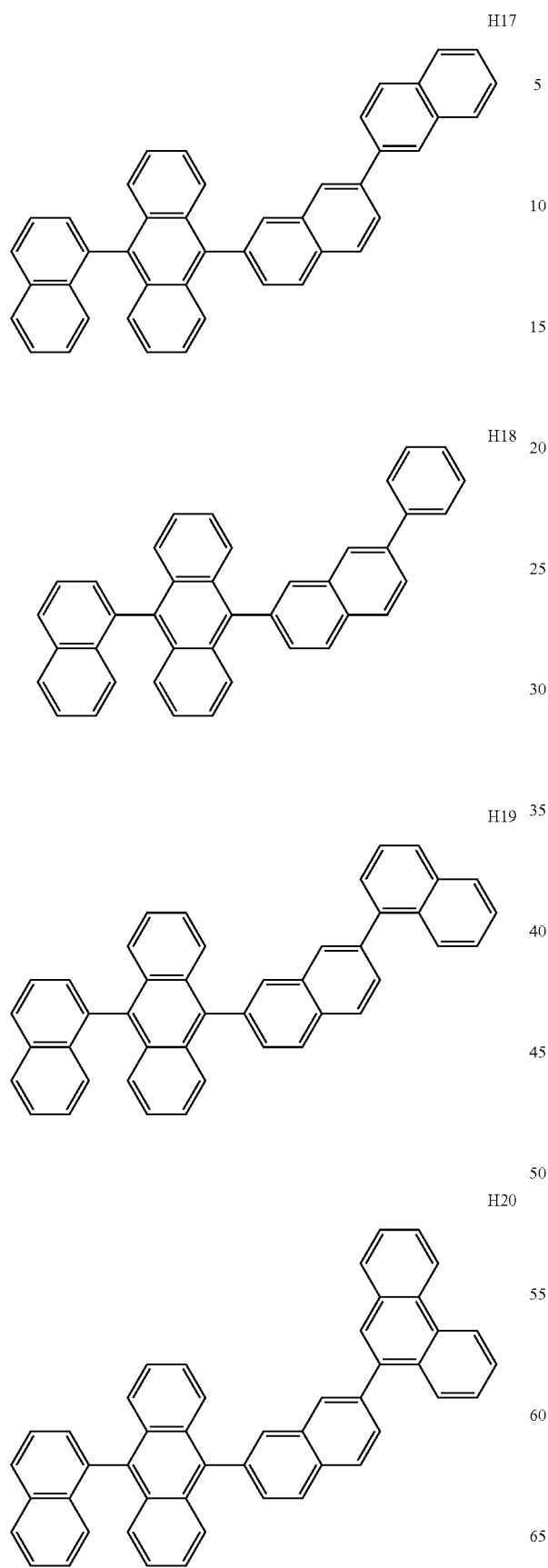
H17
H18
H19
H20
-continued
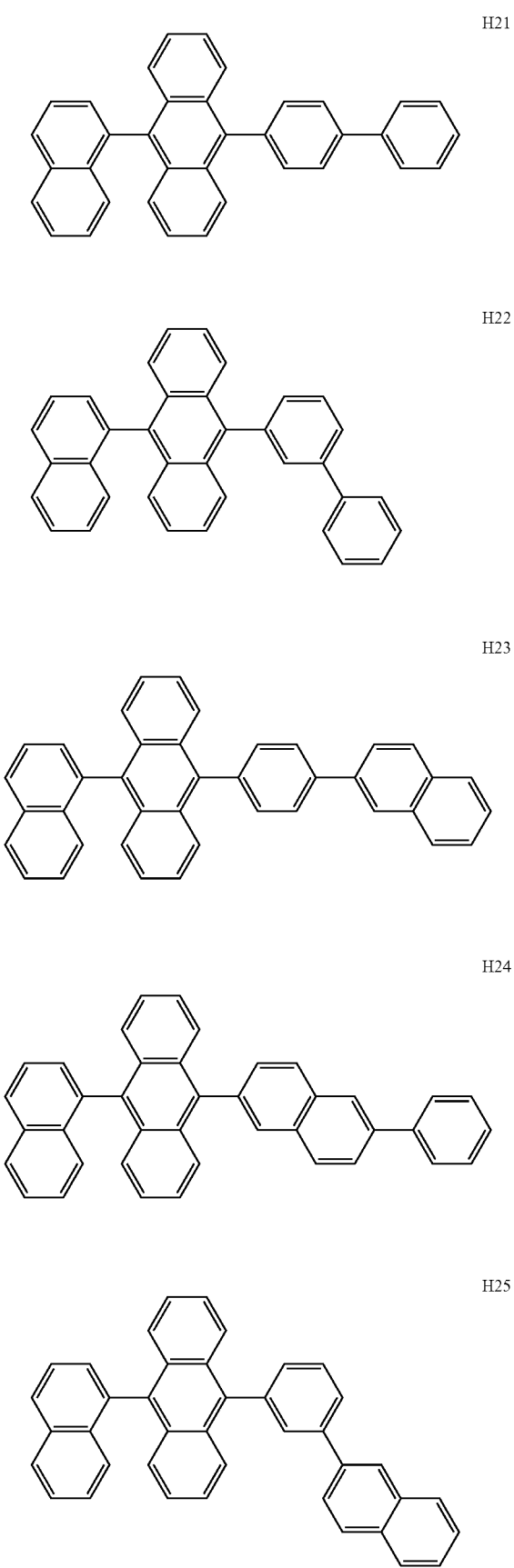
H21
H22
H23
H24
H25

H26
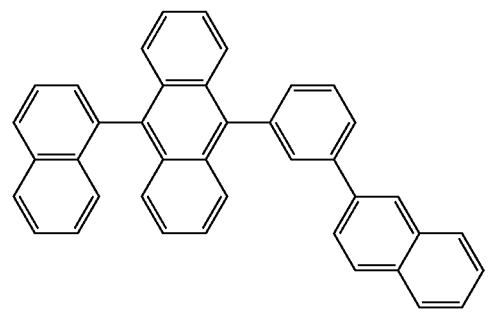
H27
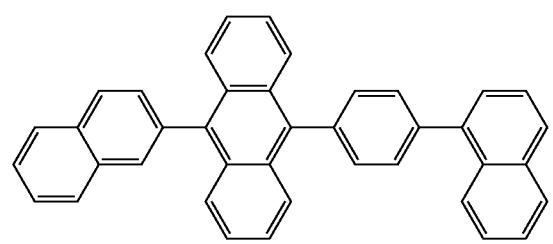
H28
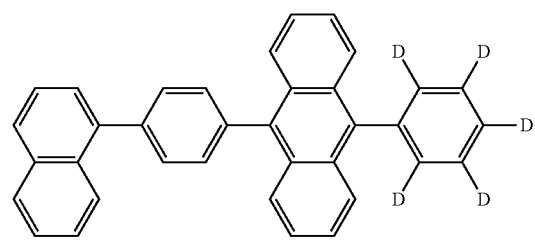
H29
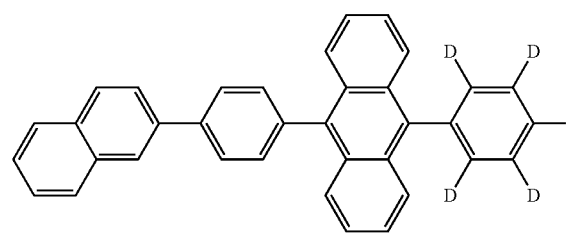
H30
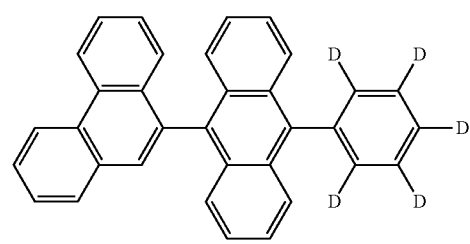
H31
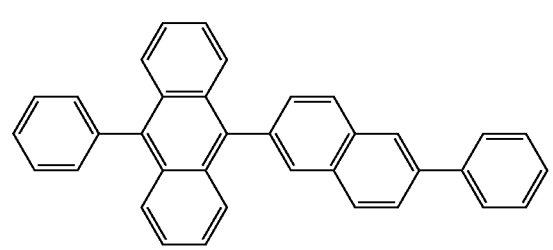
H32
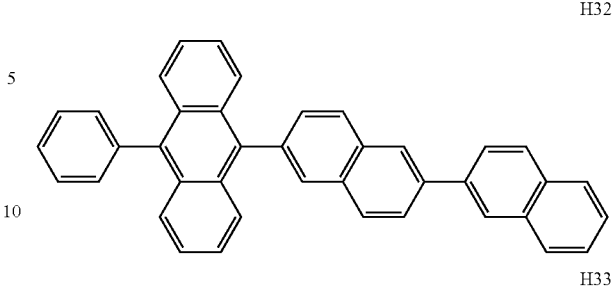
H33
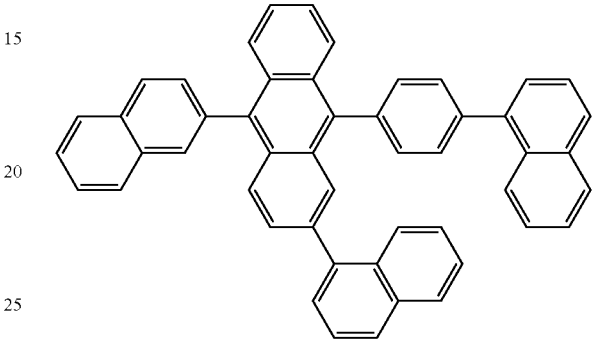
H34
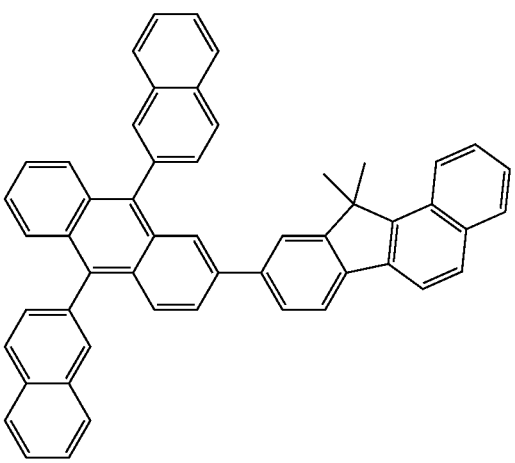
H35
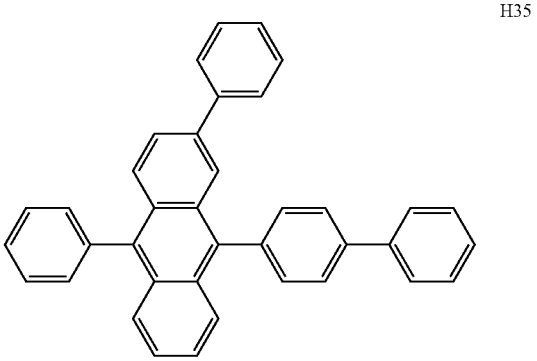

55
-continued
H36
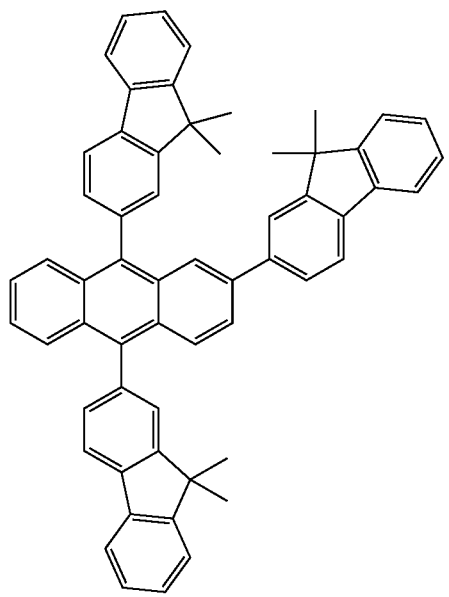
H37
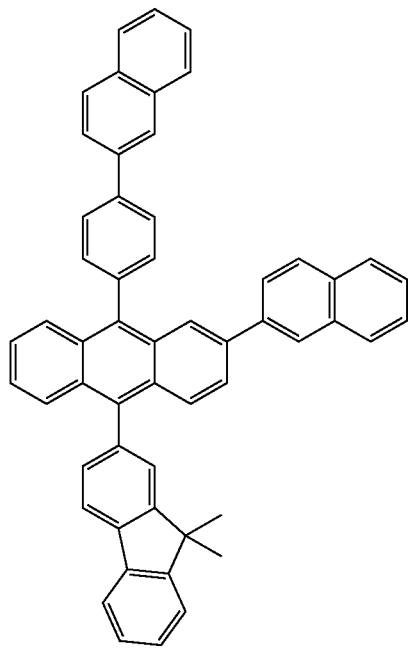
H38
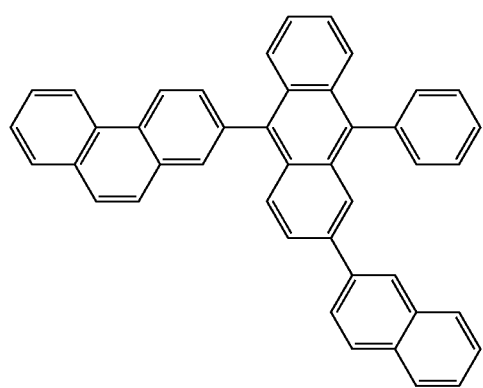
56
-continued
H39
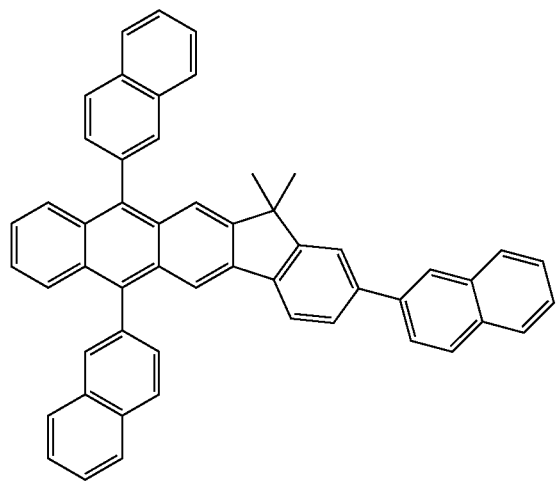
H40
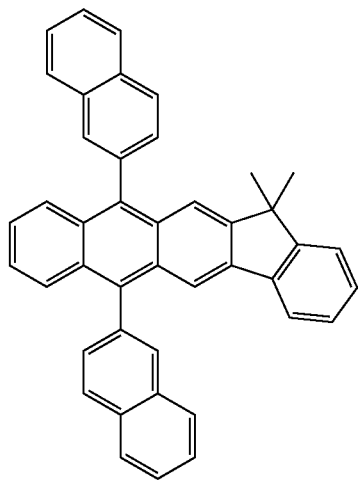
H41
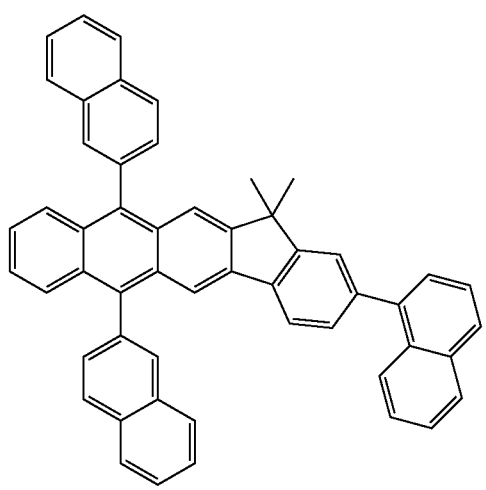

H42

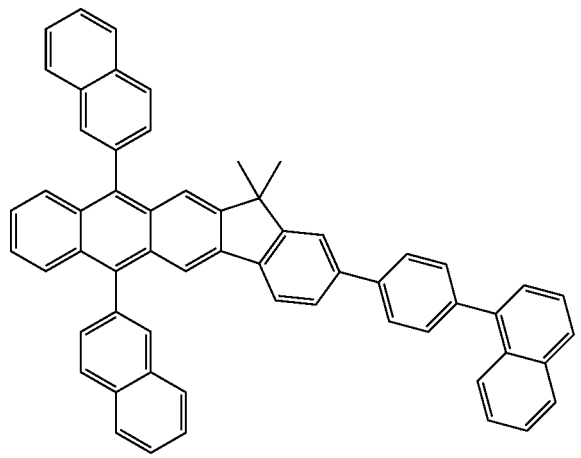

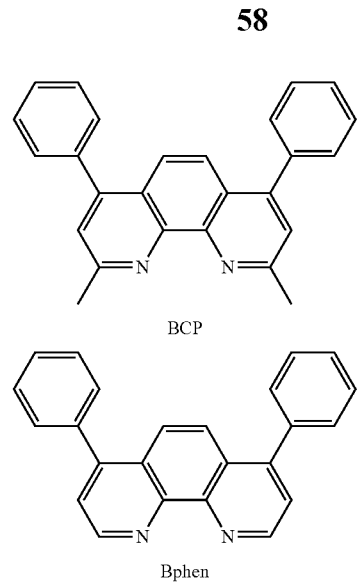

BCP

Bphen

When the organic light-emitting device is a full color organic light-emitting device, the emission layer may be patterned into a red emission layer, a green emission layer, and a blue emission layer. According to another embodiment, due to a stack structure including a red emission layer, a green emission layer, and/or a blue emission layer, the emission layer may emit white light.

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP and Bphen, but may also include other materials.

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, Balq, TAZ, and NTAZ.

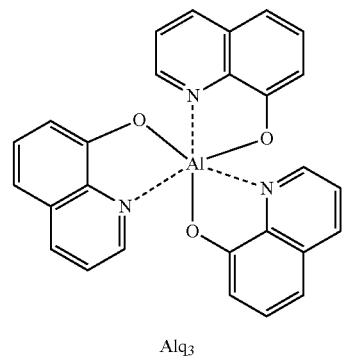

Alq$_3$

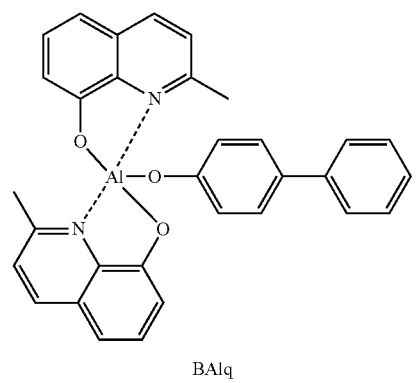

BAlq

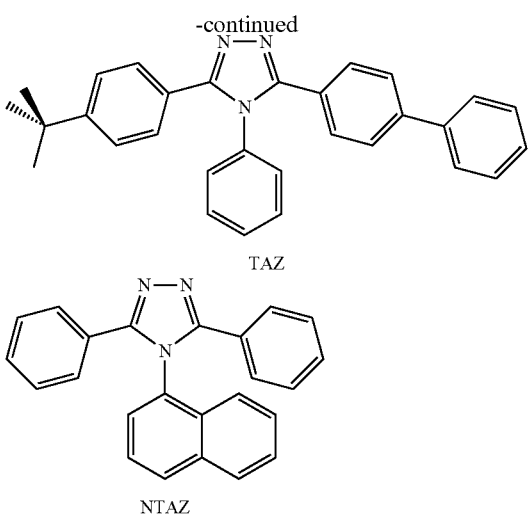

TAZ

NTAZ

According to another embodiment, the electron transport layer may include at least one of ET1 and ET2, but are not limited thereto:

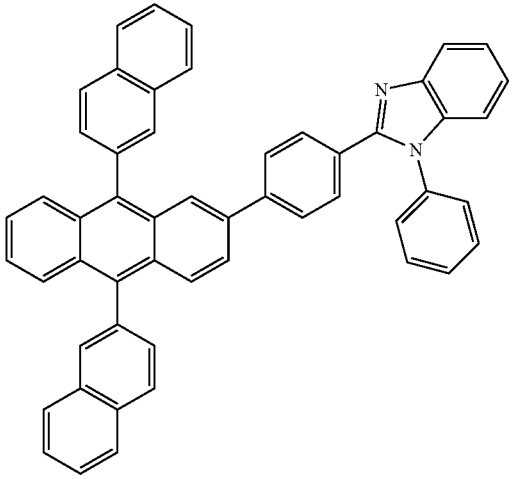

ET1

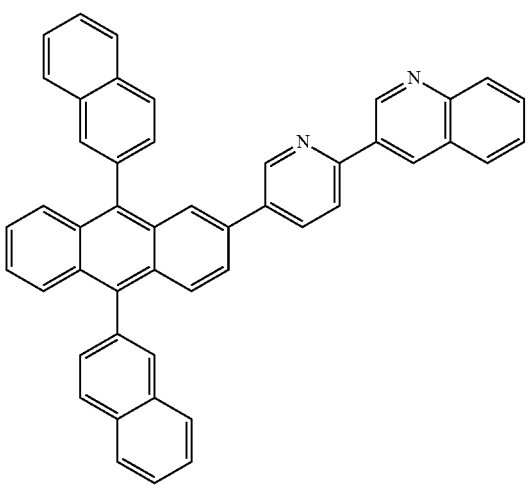

ET2

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

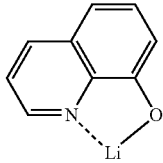

ET-D1

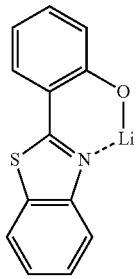

ET-D2

The electron transport region may include an electron injection layer (EIL) that allows electrons to be easily provided from a second electrode 19.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group used herein indicates a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group used herein indicates a divalent group having the same structure as the $C_1$-$C_{60}$ alkyl group.

A $C_1$-$C_{60}$ alkoxy group used herein indicates a monovalent group represented by —$OA_{101}$ (wherein $A_{101}$ is the $C_1$-$C_{60}$ alkyl group). Detailed examples thereof include a methoxy group, an ethoxy group, and an isopropyloxy group.

A $C_2$-$C_{60}$ alkenyl group used herein indicates a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group used herein indicates a divalent group having the same structure as the $C_2$-$C_{60}$ alkenyl group.

A $C_2$-$C_{60}$ alkynyl group used herein indicates a hydrocarbon group formed by substituting at least one carbon triple bond in the middle or at the terminal of the $C_2$-$C_{60}$ alkyl group. Detailed examples thereof are an ethynyl group, and a propynyl group. A $C_2$-$C_{60}$ alkynylene group used herein indicates a divalent group having the same structure as the $C_2$-$C_{60}$ alkynyl group.

A $C_3$-$C_{10}$ cycloalkyl group used herein indicates a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group used herein indicates a divalent group having the same structure as the $C_3$-$C_{10}$ cycloalkyl group.

A $C_1$-$C_{10}$ heterocycloalkyl group used herein indicates a monovalent monocyclic group having at least one hetero atom selected from N, O, P, and S as a ring-forming atom and 1 to 10 carbon atoms. Detailed examples thereof are a tetrahydrofuranyl group, and a tetrahydrothiophenyl group. A $C_1$-$C_{10}$ heterocycloalkylene group used herein indicates a divalent group having the same structure as the $C_1$-$C_{10}$ heterocycloalkyl group.

A $C_3$-$C_{10}$ cycloalkenyl group used herein indicates a monovalent monocyclic group that has 3 to 10 carbon atoms and at least one double bond in the ring thereof, which is not aromatic. Detailed examples thereof are a cyclopentenyl group, a cyclohexenyl group, and a cycloheptenyl group. A $C_3$-$C_{10}$ cycloalkenylene group used herein indicates a divalent group having the same structure as the $C_3$-$C_{10}$ cycloalkenyl group.

A $C_1$-$C_{10}$ heterocycloalkenyl group used herein indicates a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group used herein indicates a divalent group having the same structure as the $C_1$-$C_{10}$ heterocycloalkenyl group.

A $C_6$-$C_{60}$ aryl group used herein indicates a monovalent group having a carbocyclic aromatic system having 6 to 60 carbon atoms. A $C_6$-$C_{60}$ arylene group used herein indicates a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein indicates a monovalent group having a carbocyclic aromatic system that has at least one hetero atom selected from N, O, P, and S as a ring-forming atom, and 1 to 60 carbon atoms. A $C_1$-$C_{60}$ heteroarylene group used herein indicates a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

A monovalent non-aromatic condensed polycyclic group used herein indicates a monovalent group that has two or more rings condensed to each other, only carbon atoms (for example, the number of carbon atoms may be in a range of 8 to 60) as ring forming atoms, and which is non-aromatic in the entire molecular structure. An example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic hetero-condensed polycyclic group used herein refers to a monovalent group that has two or more rings condensed to each other, has a heteroatom selected from N, O P, and S, other than carbon atoms (for example, the number of carbon atoms may be in a range of 1 to 60), as ring forming atoms, and which is non-aromatic in the entire molecular structure. An example of the monovalent non-aromatic hetero-condensed polycyclic group is a carbazolyl group. A divalent non-aromatic hetero-condensed polycyclic group used herein refers to a divalent group having the same structure as the monovalent non-aromatic hetero-condensed polycyclic group.

Hereinafter, a compound and an organic light-emitting device according to embodiments are described in detail with reference to Synthesis Examples and Examples. However, the organic light-emitting device is not limited thereto. The wording "B was used instead of A" used in describing Synthesis Examples means that a molar equivalent of A was identical to a molar equivalent of B.

SYNTHESIS EXAMPLE

Synthesis Example 1: Synthesis of Compound 1

Compound 1 was synthesized according to Reaction Scheme 1 below:

Reaction Scheme 1

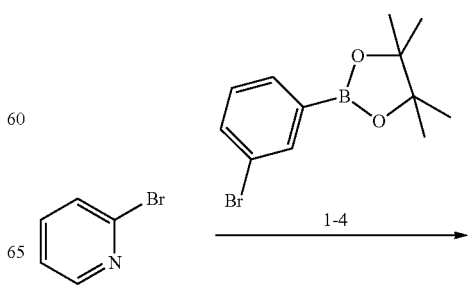

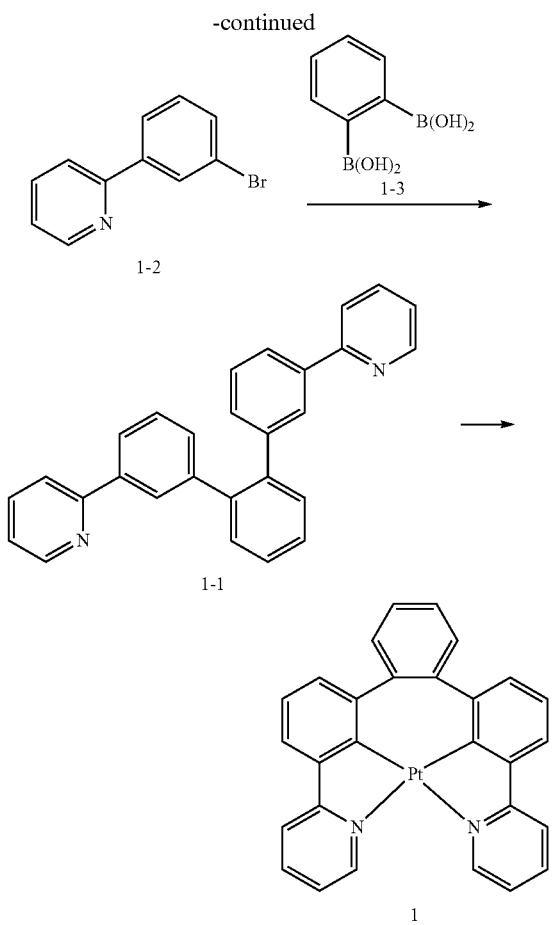

1) Synthesis of Intermediate 1-4

47.0 g (150.0 mmol) of 1-bromo-3-iodobenzene was dissolved in 600 ml of tetrahydrofuran, and then, 94.0 ml (150.0 mmol) of 1.6 M n-BuLi (in hexane) was added thereto and the result was stirred at a temperature of −78° C. for about 1 hour. Next, 37 ml (180.0 mmol) of 2-isopropoxy-4,4,5,5-tetramethyl-1,3,2-dioxaborolane was added thereto, and then stirred at a temperature of −78° C. for about 1 hour. Then, the result was stirred at room temperature for about 18 hours. When the reaction is completed, 400 ml of ethyl acetate and 500 ml of brine were added for an extraction process, and then an organic layer was dried with a magnesium sulfate and distilled under reduced pressure. The result was separation-purified by column chromatography, thereby obtaining about 38.2 g (135.0 mmol, yield of 90%) of Intermediate 1-4. The obtained compound was confirmed by LC-MS.

LC-MS m/z=284 (M+H)$^+$

2) Synthesis of Intermediate 1-2

6.0 g (38.0 mmol) of 2-bromopyridine was dissolved in 300 ml of tetrahydrofuran, and then 2.2 g (1.9 mmol) of tetrakistriphenylphosphine Pd(0) was added thereto at room temperature and the result was stirred for about 5 minutes. Next, 10.8 g (38.0 mmol) of 1-bromo-3-iodobenzene and 10.5 g (76.0 mmol) of potassium carbonate were added thereto. Then, 150 ml of distilled water was added thereto and refluxed while heating at a temperature of 70° C. for a day. When the reaction was completed, 100 ml of ethyl acetate added for an extraction process, and then an organic layer was dried with a magnesium sulfate and distilled under reduced pressure. The result was separation-purified by column chromatography, thereby obtaining about 7.6 g (32.3 mmol, yield of 85%) of Intermediate 1-2. The obtained compound was confirmed by LC-MS.

LC-MS m/z=234 (M+H)$^+$

3) Synthesis of Intermediate 1-1

6.0 g (25.6 mmol) of Intermediate 1-2 was dissolved in 200 ml of ethanol and 10 ml distilled water, and then, 0.8 g (0.6 mmol) of tetrakistriphenylphosphine Pd(0) was added thereto at room temperature and the result was stirred for about 5 minutes. Next, 2.0 g (12.0 mmol) of Intermediate 1-3 (Reference: Organometallics 2006, 25, 349-357) and 6.6 g (48.0 mmol) of potassium carbonate were added thereto, and then the result was refluxed while heating in a pressure flask at a temperature of 150° C. for two days. When the reaction was completed, the result was vacuum-evaporated, and 300 ml of dichloromethane and 100 ml of brine were added for an extraction process. The extracted organic layer was dried with a magnesium sulfate and distilled under reduced pressure. The result was separation-purified by column chromatography, thereby obtaining about 2.5 g (6.5 mmol, yield of 54%) of Intermediate 1-1. The obtained compound was confirmed by LC-MS.

LC-MS m/z=385 (M+H)$^+$

Synthesis of Compound 1

2.5 g (6.5 mmol) of Compound 1-1 was dissolved in 200 ml of acetic acid (glacial) at room temperature, and then 2.7 g (6.5 mmol) of K$_2$PtCl$_4$ and catalytic amount of Bu$_4$NCl were added thereto and refluxed while heating at 145° C. for 18 hours. After 18 hours, the result was cooled to room temperature, and dichloromethane and water were added for an extraction process. The extracted organic layer was dried with a magnesium sulfate and separation-purified by column chromatography, thereby obtaining about 0.6 g (1.0 mmol, yield of 15%) of Compound 1.

LC-MS m/z=578 (M+H)$^+$ $^1$H NMR (300 MHz, CDCl$_3$) δ=8.97-8.85 (m, 2H), 8.31-8.19 (m, 2H), 7.99-7.74 (m, 6H), 7.68-7.52 (m, 4H), 7.14-7.10 (m, 2H), 6.42-6.32 (m, 2H)

Synthesis Example 2: Synthesis of Compound 2

Compound 2 was synthesized according to Reaction Scheme 2 below:

Reaction Scheme 2

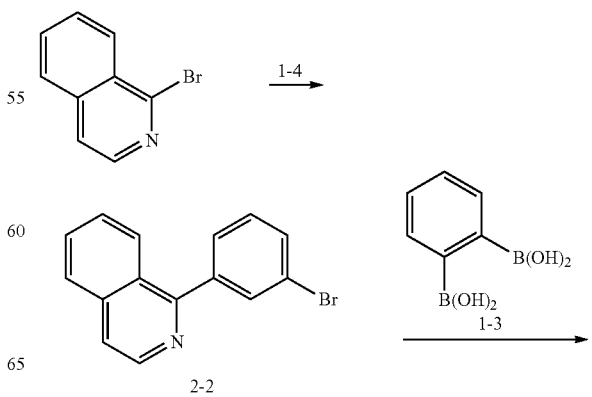

-continued

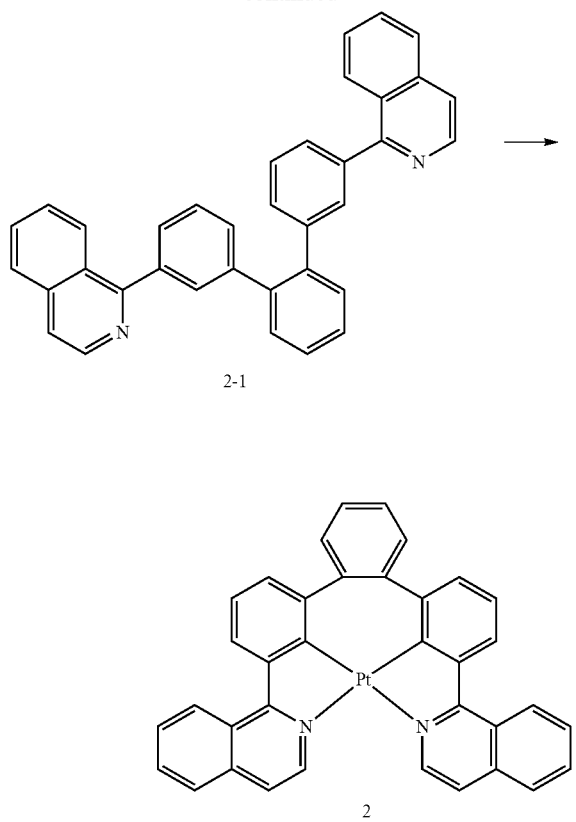

1) Synthesis of Intermediate 2-2

Intermediate 2-2 (yield of 63%) was synthesized in the same manner as Intermediate 1-2 of Synthesis Example 1, except that bromoisoquinoline was used instead of 2-bromopyridine. The obtained compound was confirmed by LC-MS.

LC-MS m/z=285 (M+H)$^+$

2) Synthesis of Intermediate 2-1

Intermediate 2-1 (yield of 40%) was synthesized in the same manner as Intermediate 1-1 of Synthesis Example 1, except that Intermediate 2-2 was used instead of Intermediate 1-2. The obtained compound was confirmed by LC-MS.

LC-MS m/z=485 (M+H)$^+$

3) Synthesis of Compound 2

1.0 g (2.0 mmol) of Compound 2-1 was dissolved in 200 ml of acetic acid (glacial) at room temperature, and then 0.8 g (2.0 mmol) of K$_2$PtCl$_4$ and catalytic amount of Bu$_4$NCl were added thereto and the result was refluxed while heating at a temperature of 145° C. for 18 hours. After 18 hours, the result was cooled to room temperature, and dichloromethane and water were added for an extraction process. The extracted organic layer was dried with a magnesium sulfate and separation-purified by column chromatography, thereby obtaining about 0.3 g (0.4 mmol, yield of 20%) of Compound 2.

LC-MS m/z=678 (M+H)$^+$ $^1$H NMR (300 MHz, CDCl$_3$) δ=8.72-8.68 (m, 2H), 8.28-8.22 (m, 2H), 7.98-7.38 (m, 18H).

Synthesis Example 3: Synthesis of Compound 3

Compound 3 was synthesized according to Reaction Scheme 3 below:

Reaction Scheme 3

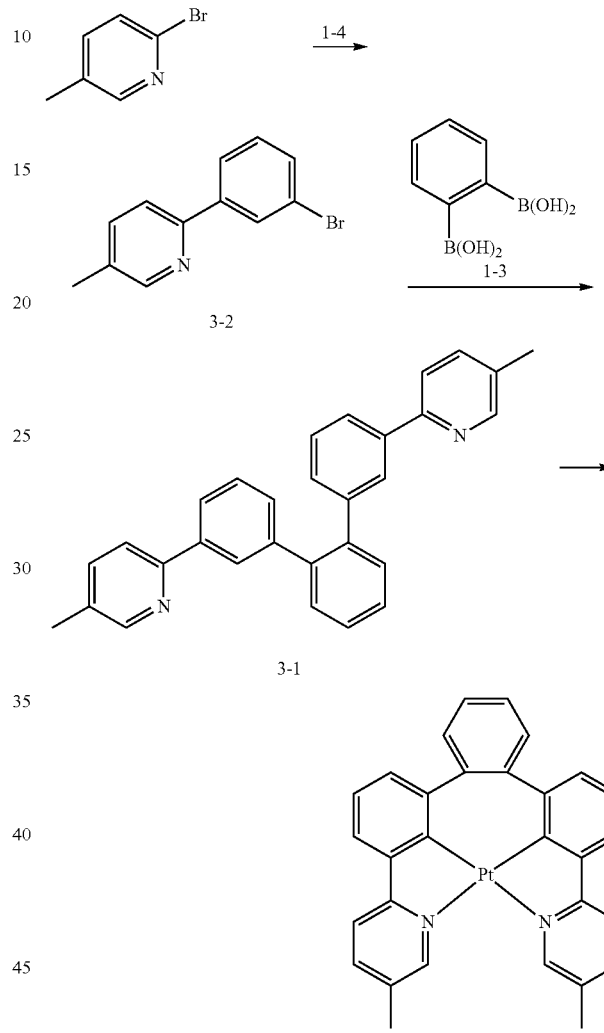

1) Synthesis of Intermediate 3-2

Intermediate 3-2 (yield of 65%) was synthesized in the same manner as Intermediate 1-2 of Synthesis Example 1, except that 2-bromo-5-methylpyridine was used instead of 2-bromopyridine. The obtained compound was confirmed by LC-MS.

LC-MS m/z=248 (M+H)$^+$

2) Synthesis of Intermediate 3-1

Intermediate 3-1 (yield of 50%) was synthesized in the same manner as Intermediate 1-1 of Synthesis Example 1, except that Intermediate 3-2 was used instead of Intermediate 1-2. The obtained compound was confirmed by LC-MS.

LC-MS m/z=399 (M+H)$^+$

3) Synthesis of Compound 3

Compound 3 (yield of 20%) was synthesized in the same manner as Compound 1 of Synthesis Example 1, except that Intermediate 3-1 was used instead of Intermediate 1-1. The obtained product was confirmed by LCMS and $^1$H NMR.

LC-MS m/z=606 (M+H)$^+$ $^1$H NMR (300 MHz, CDCl$_3$) δ=8.65 (s, 2H), 8.25 (d, 2H), 7.93-7.49 (m, 10H), 7.12 (d, 2H), 2.32 (s, 6H).

Synthesis Example 4: Synthesis of Compound 4

Compound 4 was synthesized according to Reaction Scheme 4 below:

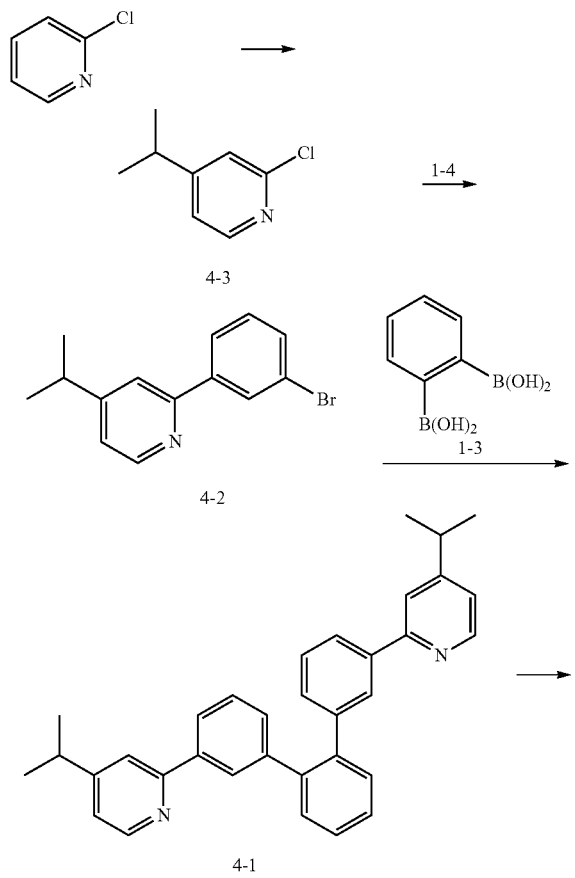

1) Synthesis of Intermediate 4-3

10.0 g (88.0 mmol) of 2-chloropyridine was dissolved in 200 ml of tetrahydrofuran, and then 15.6 g (96.8 mmol) of BF$_3$.OEt$_2$ was slowly added thereto at a temperature of 0° C. and the result was stirred at a temperature of 0° C. for about 30 minutes. Next, the result was cooled to a temperature of −78° C., and then 95.0 ml of iso-PrMgCl.LiCl (1.28 M in THF, 105.6 mmol) was slowly added thereto and the result was stirred for 1 hour. After an hour, 43.3 g (176.0 mmol) of chloranil was added thereto and the result was stirred at room temperature for 3 hours. When the reaction was completed, aqueous ammonia and ethyl acetate were added thereto for an extraction process, and an extracted organic layer was dried with a magnesium sulfate and distilled under reduced pressure. The result was separation-purified by column chromatography, thereby obtaining about 7.5 g (48.4 mmol, yield of 55%) of Intermediate 4-3. The obtained Compound was confirmed by LC-MS and NMR.

LC-MS m/z=156 (M+H)$^+$ $^1$H NMR (300 MHz, CDCl$_3$) δ=8.27 (d, 1H), 7.17 (br s, 1H), 7.05 (d, 1H), 2.99-2.80 (m, 1H), 1.26 (d, 6H)

2) Synthesis of Intermediate 4-2

Intermediate 4-4 (yield of 60%) was synthesized in the same manner as Intermediate 1-2 of Synthesis Example 1, except that Intermediate 4-3 was used instead of 2-bromopyridine. The obtained compound was identified by LC-MS.

LC-MS m/z=277 (M+H)$^+$

3) Synthesis of Intermediate 4-1

Intermediate 4-1 (yield of 60%) was synthesized in the same manner as Intermediate 1-1 of Synthesis Example 1, except that Intermediate 4-2 was used instead of Intermediate 1-2. The obtained compound was confirmed by LC-MS.

LC-MS m/z=469 (M+H)$^+$

4) Synthesis of Compound 4

Compound 4 (yield of 20%) was synthesized in the same manner as Compound 1 of Synthesis Example 1, except that Intermediate 4-1 was used instead of Intermediate 1-1. The obtained product was confirmed by LCMS and $^1$H NMR.

LC-MS m/z=662 (M+H)$^+$ $^1$H NMR (300 MHz, CDCl$_3$) δ=8.73 (d, 2H), 8.26-8.24 (m, 2H), 7.96-7.53 (m, 10H), 7.09 (d, 2H), 2.84-2.82 (m, 2H), 1.23 (d, 12H).

Synthesis Example 5: Synthesis of Compound 5

Compound 5 was synthesized according to Reaction Scheme 5 below:

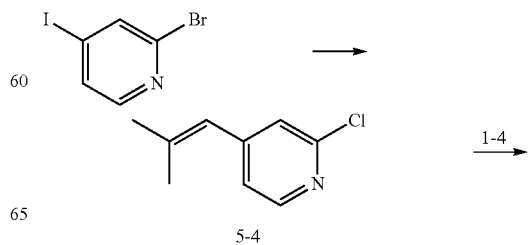

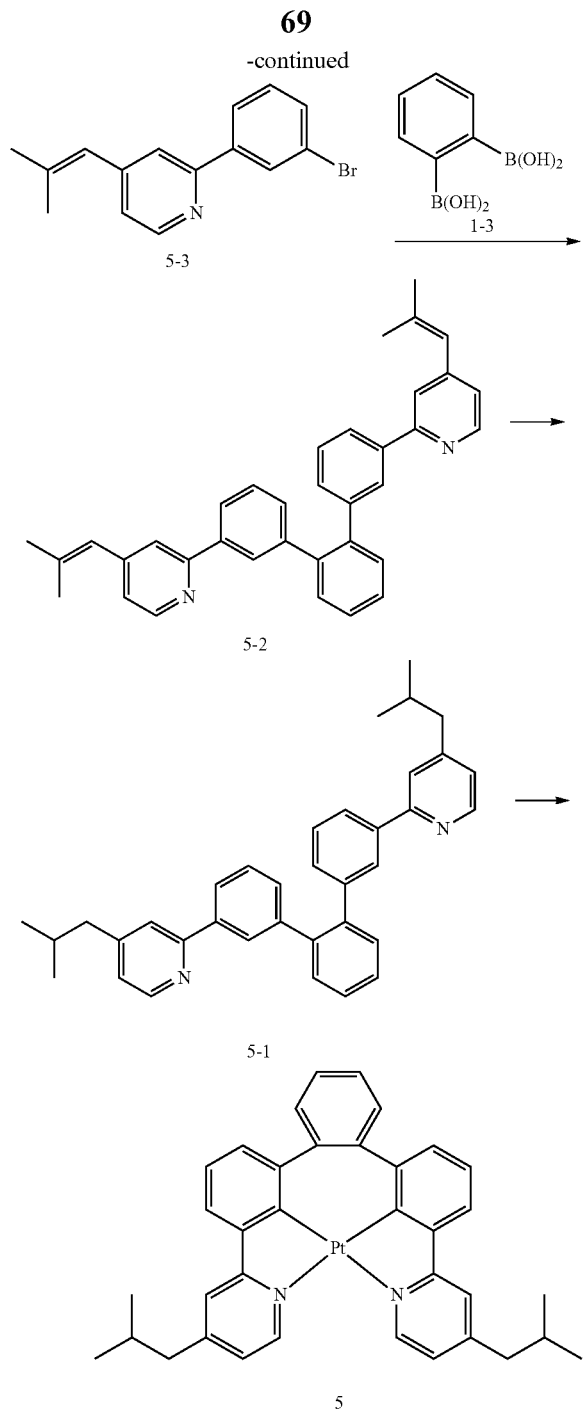

1) Synthesis of Intermediate 5-4

282.0 ml (141.0 mmol) of 2-methyl-1-propenylmagnesium bromide was dissolved in 400 ml of tetrahydrofuran 400 ml, and then 154.0 ml (155.3 mmol) of $ZnCl_2$ was slowly added thereto at a temperature of 0° C. and the result was stirred for about 1 hour. After an hour, 20.0 g (70.6 mmol) of 2-bromo-4-iodopyridine and 2.5 g (3.5 mmol) of bis(triphenylphosphine)palladium(II) dichloride were added thereto and the result was stirred at room temperature for 22 hours. When the reaction was completed, the result was neutralized with 4.0 N HCl aqueous solution, and then dichloromethane and distilled water were added thereto for an extraction process. The extracted organic layer was dried with a magnesium sulfate and distilled under reduced pressure. The result was separation-purified by column chromatography, thereby obtaining about 8.0 g (48.0 mmol, yield of 68%) of Intermediate 5-4. The obtained compound was confirmed by LC-MS.

LC-MS m/z=168 (M+H)$^+$

2) Synthesis of Intermediate 5-3

Intermediate 5-3 (yield of 55%) was synthesized in the same manner as Intermediate 1-2 of Synthesis Example 1, except that Intermediate 5-4 was used instead of 2-bromopyridine. The obtained compound was identified by LC-MS.

LC-MS m/z=288 (M+H)$^+$

3) Synthesis of Intermediate 5-2

Intermediate 5-2 (yield of 42%) was synthesized in the same manner as Intermediate 1-1 of Synthesis Example 1, except that Intermediate 5-3 was used instead of Intermediate 1-2. The obtained compound was confirmed by LC-MS.

LC-MS m/z=493 (M+H)$^+$

4) Synthesis of Intermediate 5-1

3.0 g (6.0 mmol) of Intermediate 5-2 was dissolved in 100 ml of anhydrous methanol, and then 0.6 g (10% by weight) of Pd/C was added thereto at room temperature; a hydrogen gas was injected thereto; and the result was stirred at room temperature for 18 hours. When the reaction was completed, the result was filtered by celite and distilled under reduced pressure. The result was separation-purified by column chromatography, thereby obtaining about 2.9 g (5.90 mmol, yield of 99%) of Intermediate 5-1. The obtained compound was confirmed by LC-MS.

LC-MS m/z=497 (M+H)$^+$

5) Synthesis of Compound 5

Compound 5 (yield of 15%) was synthesized in the same manner as Compound 1 of Synthesis Example 1, except that Intermediate 5-1 was used instead of Intermediate 1-1. The obtained product was confirmed by LCMS and $^1$H NMR.

LC-MS m/z=690 (M+H)$^+$ $^1$H NMR (300 MHz, CDCl$_3$) δ=8.56 (d, 2H), 8.25-8.22 (br s, 2H), 7.98-7.58 (m, 10H), 7.06 (d, 2H), 3.26 (d, 4H), 1.85-1.83 (m, 2H), 0.92 (d, 12H).

Synthesis Example 6: Synthesis of Compound 6

Compound 6 was synthesized according to Reaction Scheme 6 below:

Reaction Scheme 6

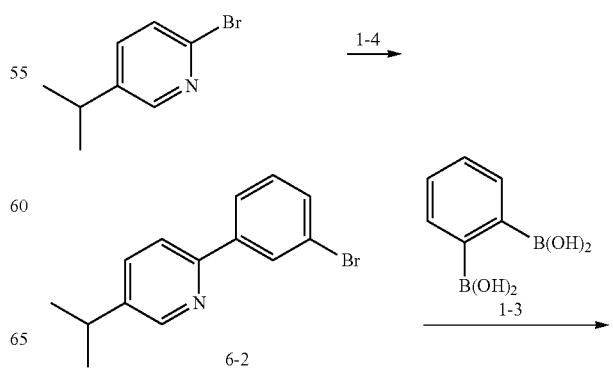

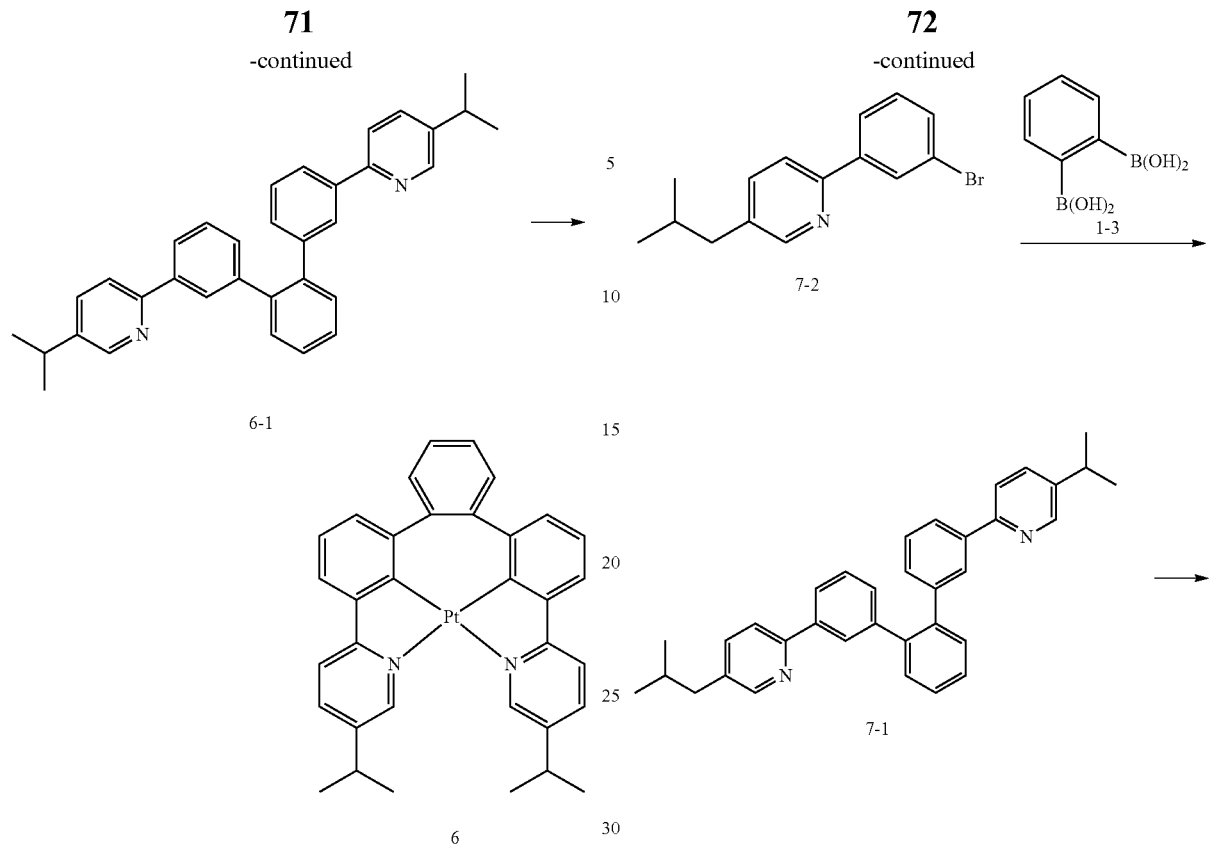

1) Synthesis of Intermediate 6-2

Intermediate 6-2 (yield of 65%) was synthesized in the same manner as Intermediate 1-2 of Synthesis Example 1, except that 2-bromo-5-iso-propylpyridine was used instead of 2-bromopyridine. The obtained compound was confirmed by LC-MS.

LC-MS m/z=276 (M+H)$^+$

2) Synthesis of Intermediate 6-1

Intermediate 6-1 (yield of 45%) was synthesized in the same manner as Intermediate 1-1 of Synthesis Example 1, except that Intermediate 6-2 was used instead of Intermediate 1-2. The obtained compound was confirmed by LC-MS.

LC-MS m/z=469 (M+H)$^+$

3) Synthesis of Compound 6

Compound 6 (yield of 15%) was synthesized in the same manner as Compound 1 of Synthesis Example 1, except that Intermediate 6-1 was used instead of Intermediate 1-1. The obtained product was confirmed by LCMS and $^1$H NMR.

LC-MS m/z=662 (M+H)$^+$ $^1$H NMR (300 MHz, CDCl$_3$) δ=8.62 (s, 2H), 8.28 (d, 2H), 7.95-7.55 (m, 10H), 7.16 (d, 2H), 2.86-2.84 (m, 2H), 1.19 (d, 12H).

Synthesis Example 7: Synthesis of Compound 7

Compound 7 was synthesized according to Reaction Scheme 7 below:

Reaction Scheme 7

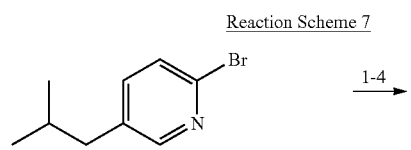

1) Synthesis of Intermediate 7-2

Intermediate 7-2 (yield of 75%) was synthesized in the same manner as Intermediate 1-2 of Synthesis Example 1, except that 2-bromo-5-iso-butylpyridine (Reference for Synthesis Example: European JOC, 2011(30), 6032-6038) was used instead of 2-bromopyridine. The obtained compound was identified by LC-MS.

LC-MS m/z=290 (M+H)$^+$

2) Synthesis of Intermediate 7-1

Intermediate 7-1 (yield of 45%) was synthesized in the same manner as Intermediate 1-1 of Synthesis Example 1, except that Intermediate 7-2 was used instead of Intermediate 1-2. The obtained compound was confirmed by LC-MS.

LC-MS m/z=483 (M+H)$^+$

3) Synthesis of Compound 7

Compound 7 (yield of 13%) was synthesized in the same manner as Compound 1 of Synthesis Example 1, except that Intermediate 7-1 was used instead of Intermediate 1-1. The obtained product was confirmed by LCMS and $^1$H NMR.

LC-MS m/z=690 (M+H)$^+$ $^1$H NMR (300 MHz, CDCl$_3$) δ=8.63 (s, 2H), 8.26 (d, 2H), 7.96-7.53 (m, 10H), 7.14 (d, 2H), 2.57 (s, 4H), 2.04-2.01 (m, 2H), 1.01 (d, 12H).

Synthesis Example 8: Synthesis of Compound 8

Compound 8 was synthesized according to Reaction Scheme 8 below:

Reaction Scheme 8

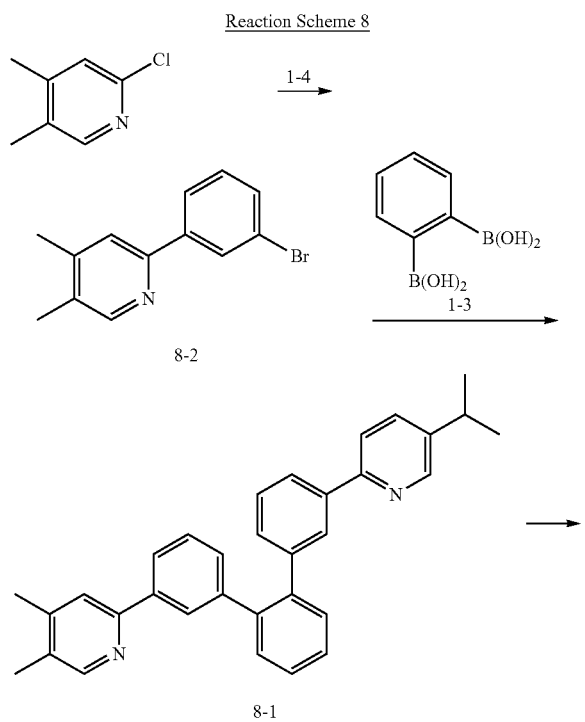

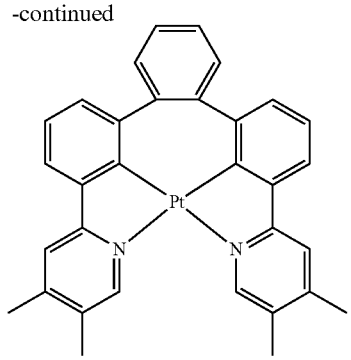

8

1) Synthesis of Intermediate 8-2

Intermediate 8-2 (yield of 65%) was synthesized in the same manner as Intermediate 1-2 of Synthesis Example 1, except that 2-chloro-4,5-dimethylpyridine a (Reference: European JOC, 2011(30), 6032-6038) was used instead of 2-bromopyridine, and 98% aqueous ethanol solution was used instead of tetrahydrofuran. The obtained compound was identified by LC-MS.

LC-MS m/z=262 (M+H)$^+$

2) Synthesis of Intermediate 8-1

Intermediate 8-1 (yield of 42%) was synthesized in the same manner as Intermediate 1-1 of Synthesis Example 1, except that Intermediate 8-2 was used instead of Intermediate 1-2. The obtained compound was confirmed by LC-MS.

LC-MS m/z=455 (M+H)$^+$

3) Synthesis of Compound 8

Compound 8 (yield of 16%) was synthesized in the same manner as Compound 1 of Synthesis Example 1, except that Intermediate 8-1 was used instead of Intermediate 1-1. The obtained product was confirmed by LCMS and $^1$H NMR.

LC-MS m/z=634 (M+H)$^+$ $^1$H NMR (300 MHz, CDCl$_3$) δ=8.58 (s, 2H), 8.29 (d, 2H), 7.95-7.51 (m, 8H), 7.21 (d, 2H), 2.36 (s, 6H), 2.34 (s, 6H).

Synthesis Example 9: Synthesis of Compound 9

Compound 9 was synthesized according to Reaction Scheme 9 below:

Reaction Scheme 9

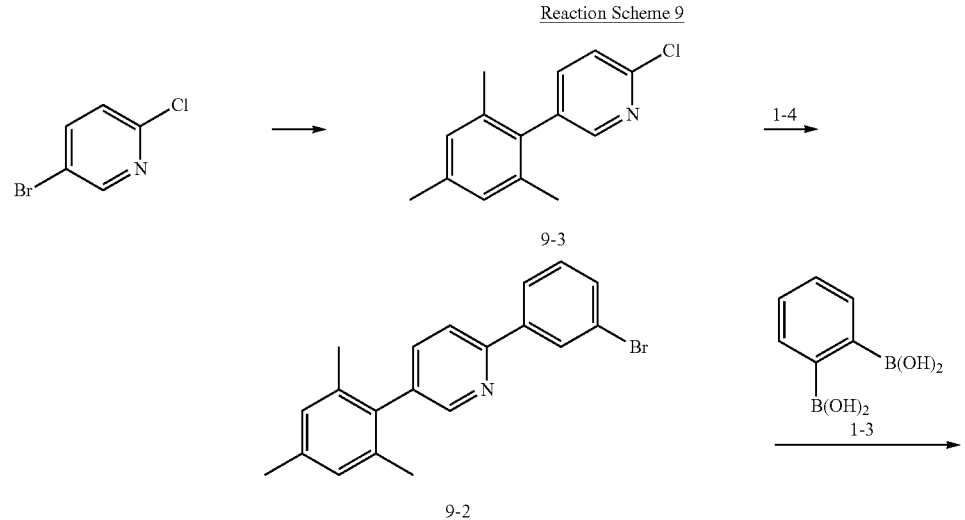

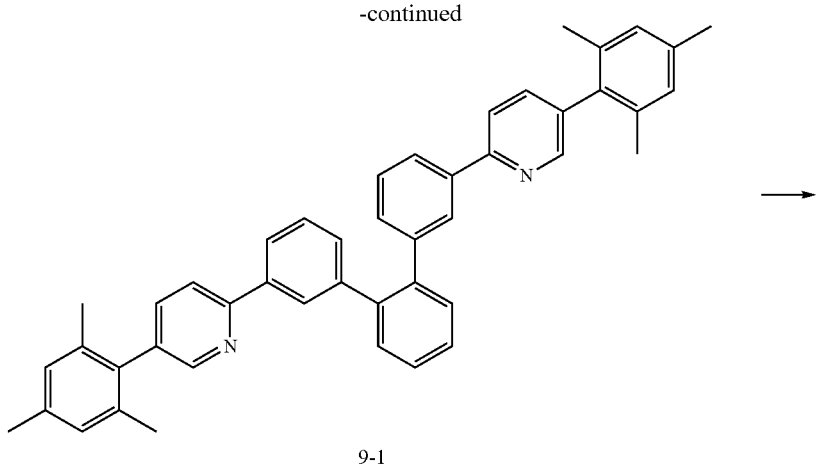

9-1

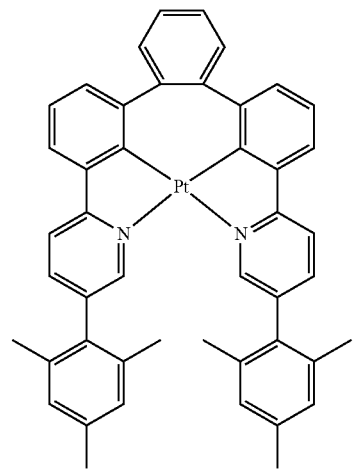

9

1) Synthesis of Intermediate 9-3

10.0 g (52.5 mmol) of 5-bromo-2-chloropyridine was dissolved in 500 ml of tetrahydrofuran, and then 3.0 g (2.6 mmol) of tetrakistriphenylphosphine Pd(0) was added thereto at room temperature and the result was stirred for about 5 minutes. Next, 9.5 g (57.89 mmol) of 2,4,6-trimethylphenyl boronic acid and 21.8 g (157.5 mmol) of potassium carbonate were added thereto. Then, 250 ml of distilled water was added thereto and the result was refluxed while heating at a temperature of 80° C. for a day. When the reaction was completed, 200 ml of ethyl acetate was added thereto for an extraction process. The extracted organic layer was dried with magnesium sulfate and distilled under reduced pressure. The result was separation-purified by column chromatography, thereby obtaining about 11.0 g (47.3 mmol, yield of 90%) of Intermediate 9-3. The obtained compound was confirmed by LC-MS.

LC-MS m/z=232 (M+H)$^+$

2) Synthesis of Intermediate 9-2

Intermediate 9-2 (yield of 72%) was synthesized in the same manner as Intermediate 1-2 of Synthesis Example 1, except that Intermediate 9-3 was used instead of 2-bromopyridine and 98% aqueous ethanol solution was used instead of tetrahydrofuran. The obtained compound was identified by LC-MS.

LC-MS m/z=353 (M+H)$^+$

3) Synthesis of Intermediate 9-1

Intermediate 9-1 (yield of 50%) was synthesized in the same manner as Intermediate 1-1 of Synthesis Example 1, except that Intermediate 9-2 was used instead of Intermediate 1-2. The obtained compound was confirmed by LC-MS.

LC-MS m/z=621 (M+H)$^+$

4) Synthesis of Compound 9

Compound 9 (yield of 15%) was synthesized in the same manner as Compound 1 of Synthesis Example 1, except that Intermediate 9-1 was used instead of Intermediate 1-1. The obtained product was confirmed by LCMS and $^1$H NMR.

LC-MS m/z=814 (M+H)$^+$ $^1$H NMR (300 MHz, CDCl$_3$) δ=8.87 (s, 2H), 8.26 (d, 2H), 8.03-7.70 (m, 10H), 7.23 (br s, 2H), 7.03 (s, 4H), 2.87 (s, 12H), 2.52 (s, 6H).

Synthesis Example 10: Synthesis of Compound 10
Compound 10 was synthesized according to Reaction Scheme 10 below:
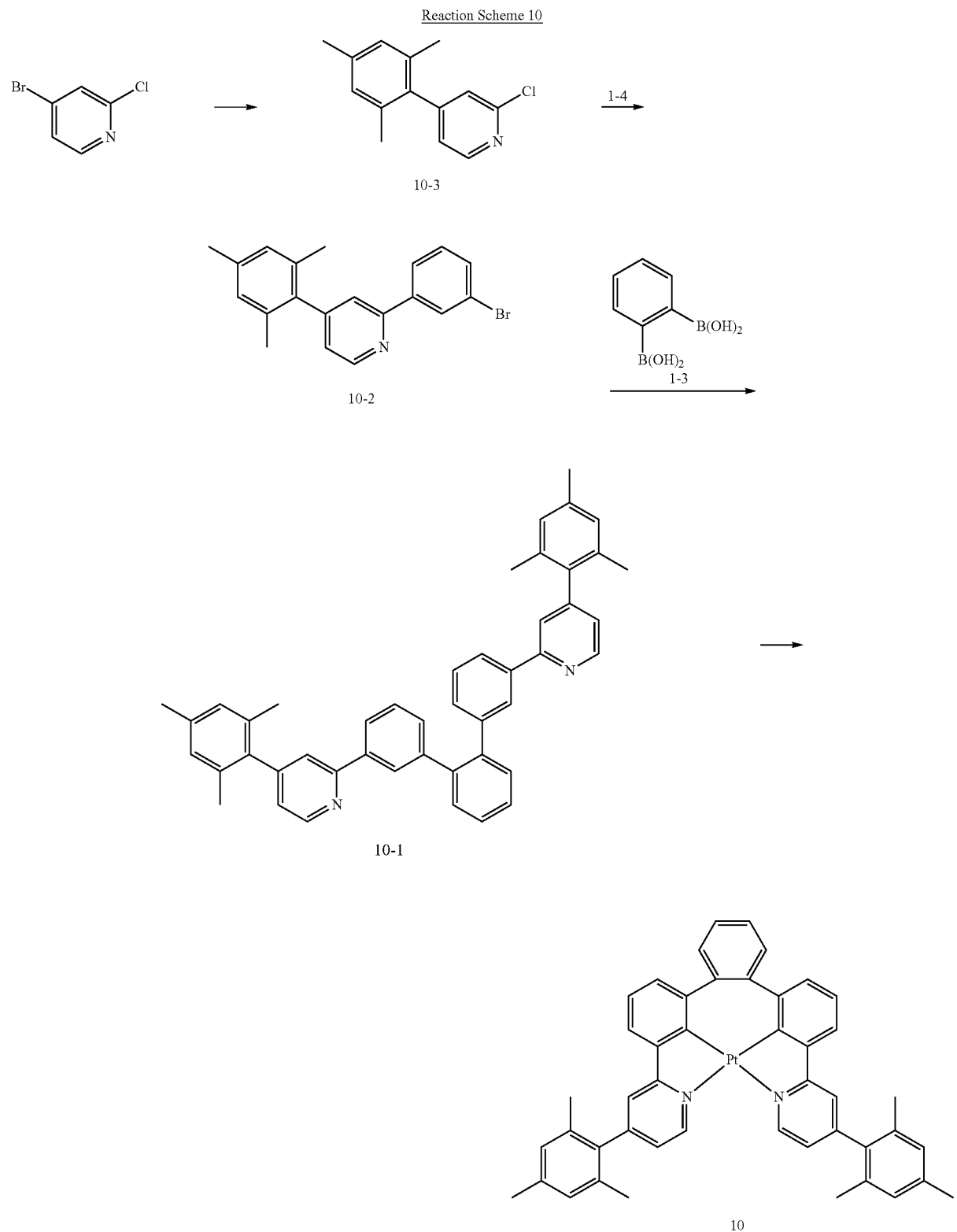

1) Synthesis of Intermediate 10-3

Intermediate 10-3 (yield of 81%) was synthesized in the same manner as Intermediate 9-3 of Synthesis Example 9, except that Intermediate 4-bromo-2-chloropyridine was used instead of 5-bromo-2-chloropyridine. The obtained compound was confirmed by LC-MS.

LC-MS m/z=232 (M+H)$^+$

2) Synthesis of Intermediate 10-2

Intermediate 10-2 (yield of 81%) was synthesized in the same manner as Intermediate 9-2 of Synthesis Example 9, except that Intermediate 10-3 was used instead of 2-bromopyridine. The obtained compound was confirmed by LC-MS.

LC-MS m/z=352 (M+H)$^+$

3) Synthesis of Intermediate 10-1

Intermediate 10-1 (yield of 45%) was synthesized in the same manner as Intermediate 9-1 of Synthesis Example 9, except that Intermediate 10-2 was used instead of Intermediate 9-2. The obtained compound was confirmed by LC-MS.

LC-MS m/z=621 (M+H)$^+$

4) Synthesis of Compound 10

Compound 10 (yield of 15%) was synthesized in the same manner as Compound 9 of Synthesis Example 9, except that Intermediate 10-1 was used instead of Intermediate 9-1. The obtained product was confirmed by LCMS and $^1$H NMR.

LC-MS m/z=814 (M+H)$^+$ $^1$H NMR (300 MHz, CDCl$_3$) δ=8.72 (d, 2H), 8.51 (br s, 2H), 8.30 (br s, 2H), 8.06-7.72 (m, 8H), 7.22 (br s, 2H), 7.01 (s, 4H), 2.90 (s, 12H), 2.51 (s, 6H).

Synthesis Example 11: Synthesis of Compound 11

Compound 11 was synthesized according to Reaction Scheme 11 below:

Reaction Scheme 11

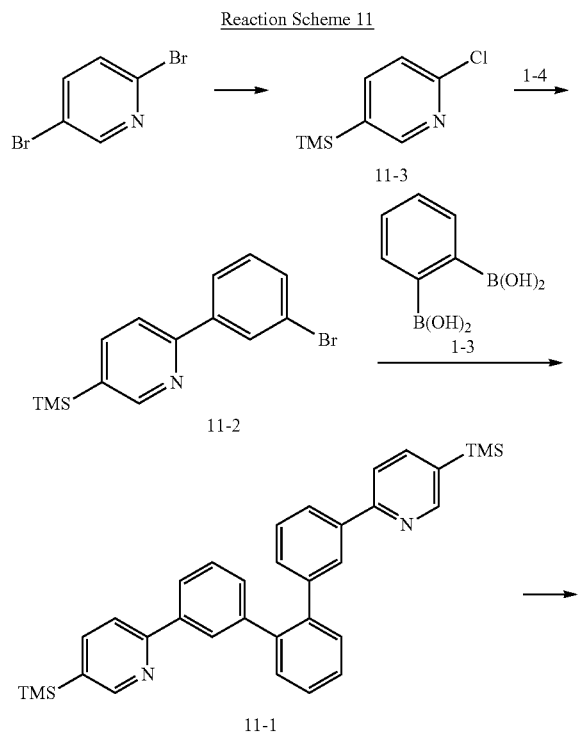

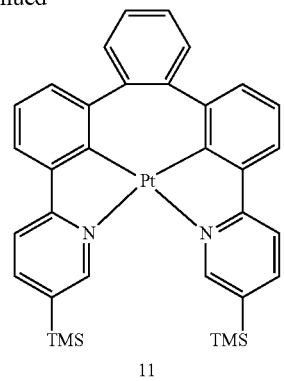

1) Synthesis of Intermediate 11-3

20.0 g (84.4 mmol) of 2,5-dibromopyridine was dissolved in 300 ml of diethylether, and then 53 ml (84.4 mmol) of 1.6 M n-BuLi in hexane was added thereto at a temperature of −78° C. and the result was stirred for about 1 hour. Next, 10.7 ml (84.4 mmol) of chlorotrimethylsilane was slowly added thereto; the result was stirred at a temperature of −78° C. for 2 hours and then heated to room temperature; and the result was stirred at room temperature for about 18 hours. When the reaction was completed, 200 ml of distilled water was added thereto, and 300 ml of ethyl acetate was added thereto for an extraction process. The extracted organic layer was dried with magnesium sulfate and distilled under reduced pressure. The result was fractionally distilled, thereby obtaining about 16.0 g (84.0 mmol, yield of 100%) of Intermediate 11-3. The obtained compound was confirmed by LC-MS.

LC-MS m/z=186 (M+H)$^+$

2) Synthesis of Intermediate 11-2

Intermediate 11-2 (yield of 65%) was synthesized in the same manner as Intermediate 1-2 of Synthesis Example 1, except that Intermediate 11-3 was used instead of 2-bromopyridine, and 98% aqueous ethanol solution was used instead of tetrahydrofuran. The obtained compound was identified by LC-MS.

LC-MS m/z=306 (M+H)$^+$

3) Synthesis of Intermediate 11-1

Intermediate 11-1 (yield of 53%) was synthesized in the same manner as Intermediate 1-1 of Synthesis Example 1, except that Intermediate 11-2 was used instead of Intermediate 1-2. The obtained compound was confirmed by LC-MS.

LC-MS m/z=529 (M+H)$^+$

4) Synthesis of Compound 11

Compound 11 (yield of 7%) was synthesized in the same manner as Compound 1 of Synthesis Example 1, except that Intermediate 11-1 was used instead of Intermediate 1-1. The obtained product was confirmed by LCMS and $^1$H NMR.

LC-MS m/z=722 (M+H)$^+$ $^1$H NMR (300 MHz, CDCl$_3$) δ=8.76 (s, 2H), 8.31 (d, 2H), 7.98-7.91 (m 2H), 7.89-7.70 (m, 8H), 7.26 (br s, 2H), 0.29 (s, 18H).

Synthesis Example 12: Synthesis of Compound 12

Compound 12 was synthesized according to Reaction Scheme 12 below:

Reaction Scheme 12

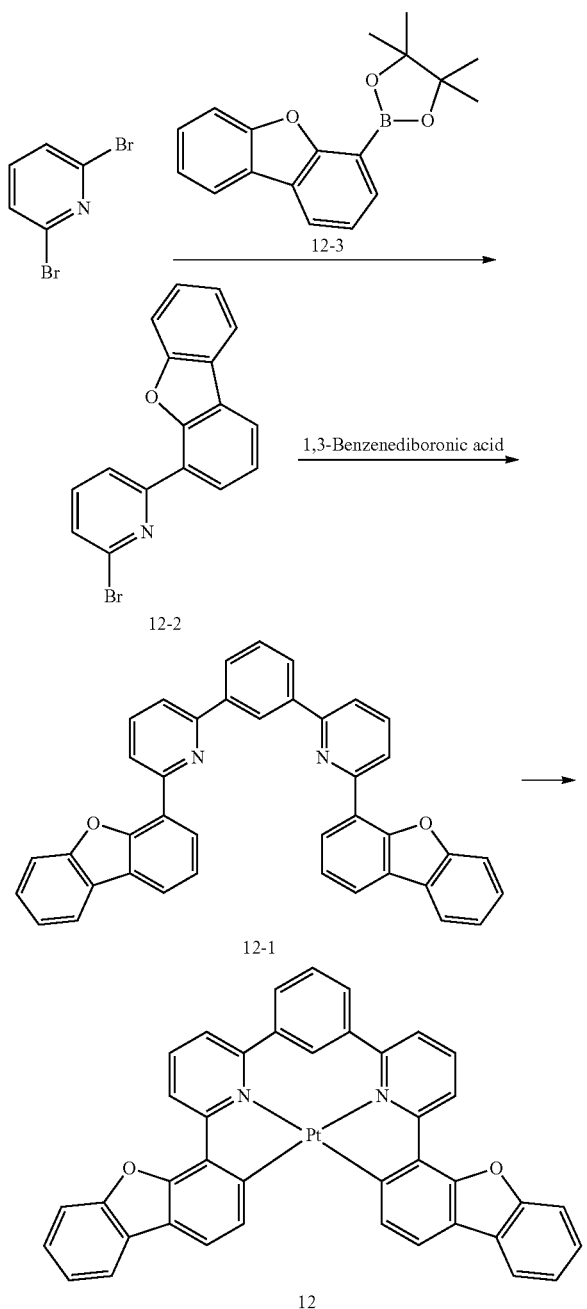

1) Synthesis of Intermediate 12-3

10.0 g (38.1 mmol) of 4-bromodibenzofuran was dissolved in 300 ml of tetrahydrofuran, and then 1.3 g (1.9 mmol) of bis(triphenylphosphine)palladium(II) dichloride was added thereto and the result was stirred for about 5 minutes. Next, 14.5 g (57.2 mmol) of bis(pinacolato)diboron and 11.2 g (114.3 mmol) of potassium acetate were added thereto and the result was refluxed while heating at a temperature of 80° C. for a day. When the reaction was completed, 200 ml of ethyl acetate was added thereto for an extraction process, and the extracted organic layer was dried with magnesium sulfate and distilled under reduced pressure. The result was separation-purified by column chromatography, thereby obtaining about 10.0 g (34.3 mmol, yield of 90%) of Intermediate 12-3. The obtained compound was confirmed by LC-MS.

LC-MS m/z=295 (M+H)$^+$

2) Synthesis of Intermediate 12-2

6.0 g (25.3 mmol) of 2,6-dibromipyridine was dissolved in 100 ml of toluene, and then 1.5 g (1.3 mmol) of tetrakistriphenylphosphine Pd(0) was added thereto at room temperature and the result was stirred for about 5 minutes. Next, 7.4 g (25.3 mmol) of Intermediate 12-3 and 8.0 g (75.9 mmol) of sodium carbonate were added thereto. Then, 30 ml of distilled water was added thereto and refluxed while heating for a day. When the reaction was completed, the result was filtered with diatomite and distilled under reduced pressure. 400 ml of ethyl acetate and 100 ml of distilled water were added thereto for an extraction process. The extracted organic layer was dried with magnesium sulfate and distilled under reduced pressure. The result was separation-purified by column chromatography, thereby obtaining about 4.6 g (14.2 mmol, yield of 56%) of Intermediate 12-2. The obtained compound was confirmed by LC-MS.

LC-MS m/z=325 (M+H)$^+$

3) Synthesis of Intermediate 12-1

4.5 g (13.9 mmol) of Intermediate 12-2 was dissolved in 200 ml of ethanol and 10 ml of distilled water, and then 0.8 g (0.7 mmol) of tetrakistriphenylphosphine Pd(0) was added thereto at room temperature and the result was stirred for about 5 minutes. Next, 1.1 g (6.7 mmol) of 1,3-benzenediboronic acid and 2.8 g (20.1 mmol) of potassium carbonate were added thereto and the result was refluxed while heating in a pressure flask at a temperature of 150° C. for three days. When the reaction was completed, the result was vacuum-concentrated; 300 ml of dichloromethane and 50 ml of brine was added thereto for an extraction process; and the extracted organic layer was dried with magnesium sulfate and distilled under reduced pressure. The result was separation-purified by column chromatography, thereby obtaining about 2.8 g (4.9 mmol, yield of 74%) of Intermediate 12-1. The obtained compound was confirmed by LC-MS.

LC-MS m/z=565 (M+H)$^+$

4) Synthesis of Compound 12

Compound 12 (yield of 20%) was synthesized in the same manner as Compound 1 of Synthesis Example 1, except that Intermediate 11-1 was used instead of Intermediate 1-1. The obtained product was confirmed by LCMS and $^1$H NMR.

LC-MS m/z=758 (M+H)$^+$ $^1$H NMR (300 MHz, CDCl$_3$) δ=8.92 (s, 1H), 8.67 (br s, 2H), 8.02-7.85 (m, 4H), 7.81 (br s, 1H), 7.72-7.35 (m, 12H), 7.22 (br s, 2H).

Synthesis Example 13: Synthesis of Compound 13

Compound 13 was synthesized according to Reaction Scheme 13 below:

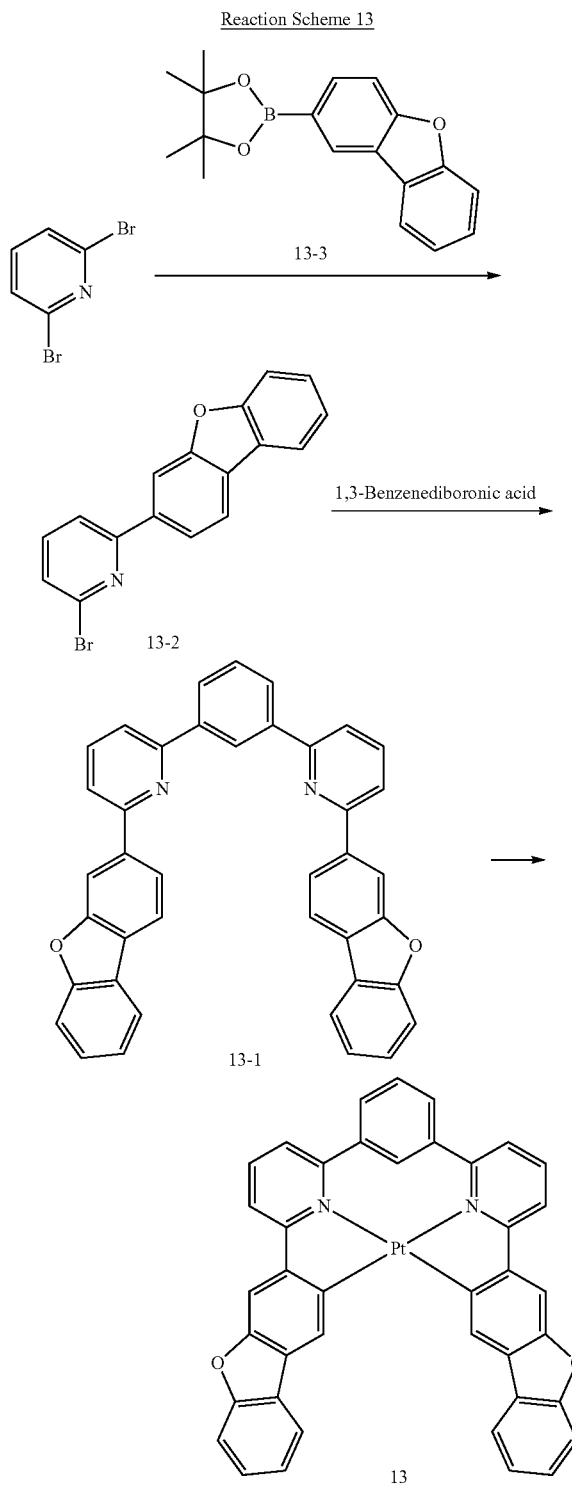

1) Synthesis of Intermediate 13-3

Intermediate 13-3 (yield of 90%) was synthesized in the same manner as Intermediate 12-3 of Synthesis Example 12, except that 2-bromodibenzofuran was used instead of 4-bromodibezofuran. The obtained compound was confirmed by LC-MS.

LC-MS m/z=295 (M+H)+

2) Synthesis of Intermediate 13-2

Intermediate 13-2 (yield of 58%) was synthesized in the same manner as Intermediate 12-2 of Synthesis Example 12, except that Intermediate 13-3 was used instead of Intermediate 12-3. The obtained compound was confirmed by LC-MS.

LC-MS m/z=323 (M+H)+

3) Synthesis of Intermediate 13-1

Intermediate 13-1 (yield of 65%) was synthesized in the same manner as Compound 12-1 of Synthesis Example 12, except that Intermediate 13-2 was used instead of Intermediate 12-2. The obtained product was confirmed by LCMS and $^1$H NMR.

LC-MS m/z=565 (M+H)+

4) Synthesis of Compound 13

Compound 13 (yield of 15%) was synthesized in the same manner as Compound 12 of Synthesis Example 12, except that Intermediate 13-1 was used instead of Intermediate 12-1. The obtained product was confirmed by LCMS and $^1$H NMR.

LC-MS m/z=758 (M+H)+

$^1$H NMR (300 MHz, CDCl$_3$) δ=8.95 (s, 1H), 8.46 (s, 2H), 8.42 (br s, 2H), 8.01 (s, 2H), 7.99 (br s, 2H), 7.82 (br s, 1H), 7.69-7.35 (m, 10H), 7.22-7.18 (m, 2H).

Synthesis Example 14: Synthesis of Compound 14

Compound 14 was synthesized according to Reaction Scheme 14 below:

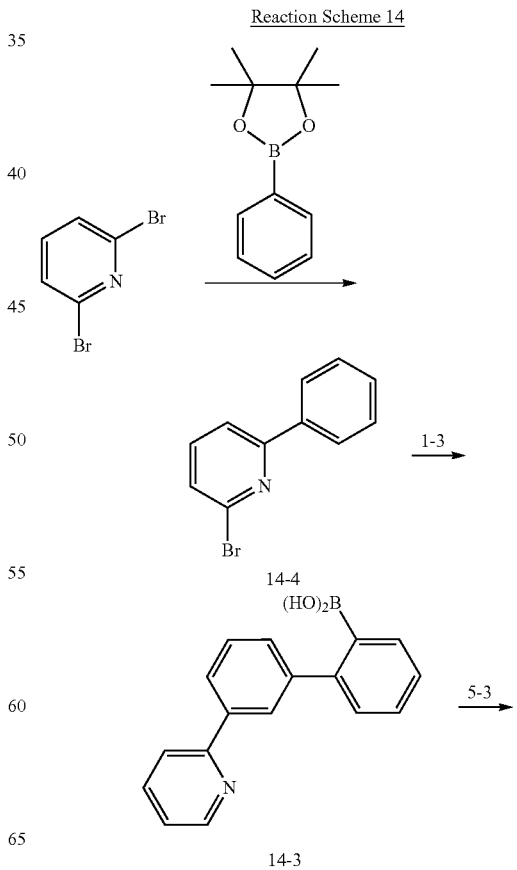

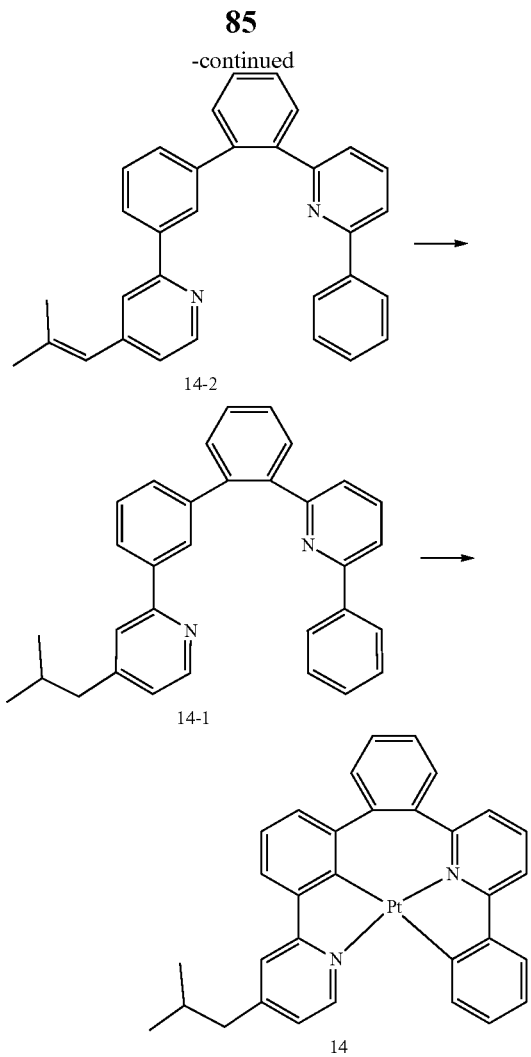

14-2

14-1

14

1) Synthesis of Intermediate 14-4

Intermediate 14-4 (yield of 68%) was synthesized in the same manner as Intermediate 12-2 of Synthesis Example 12, except that phenylboronic acid pinacol ester was used instead of Intermediate 12-3. The obtained compound was confirmed by LC-MS.

LC-MS m/z=235 (M+H)$^+$

2) Synthesis of Intermediate 14-3

8.5 g (36.3 mmol) of Intermediate 14-4 was dissolved in 300 ml of ethanol, and then 2.1 g (1.8 mmol) of tetrakistriphenylphosphine Pd(0) was added thereto at room temperature and the result was stirred for about 5 minutes. Next, 6.0 g (36.3 mmol) of Intermediate 1-3 and 15.0 g (108.9 mmol) of potassium carbonate were added thereto. Then, 15 ml of distilled water was added thereto and the result was stirred at a temperature of 50° C. for a day. When the reaction was completed, the result was distilled under reduced pressure, and then the obtained compound was extracted by adding 300 ml of dichloromethane 300 ml and 50 ml of distilled water. The extracted organic layer was dried with magnesium sulfate and distilled under reduced pressure, thereby obtaining about 10.3 g (31.2 mmol, yield of 86%) of Intermediate 14-3 without a purification process. The obtained compound was confirmed by LC-MS.

LC-MS m/z=276 (M+H)$^+$

3) Synthesis of Intermediate 14-2

10.0 g (30.3 mmol) of Intermediate 14-3 was dissolved in 300 ml of ethanol, and then 1.8 g (1.5 mmol) of tetrakistriphenylphosphine Pd(0) was added thereto at room temperature and the result was stirred for about 5 minutes. Next, 10.5 g (36.3 mmol) of Intermediate 5-3 and 12.6 g (90.9 mmol) of potassium carbonate were added thereto. Then, 15 ml of distilled water was added thereto and the result was refluxed while heating for a day. When the reaction was completed, the result was distilled under reduced pressure and the obtained compound was extracted by adding 300 ml of dichloromethane and 100 ml of brine. The extracted organic layer was dried with magnesium sulfate and distilled under reduced pressure. The result was separation-purified by column chromatography, thereby obtaining about 4.7 g (10.9 mmol, yield of 36%) of Intermediate. The obtained compound was confirmed by LC-MS.

LC-MS m/z=439 (M+H)$^+$

4) Synthesis of Intermediate 14-1

4.5 g (10.3 mmol) of Intermediate 14-2 was dissolved in 200 ml of anhydrous methanol; 0.5 g (10% by weight) of Pd/C was added thereto at room temperature; a hydrogen gas was injected thereinto; and the result was stirred at room temperature for 24 hours. When the reaction was completed, the result was filtered with celite and distilled under reduced pressure. The result was separation-purified by column chromatography, thereby obtaining about 4.5 g (10.2 mmol, yield of 99%) of Intermediate 14-1. The obtained compound was confirmed by LC-MS.

LC-MS m/z=441 (M+H)$^+$

5) Synthesis of Compound 14

Compound 14 (yield of 32%) was synthesized in the same manner as Compound 1 of Synthesis Example 1, except that Intermediate 14-1 was used instead of Intermediate 1-1. The obtained product was confirmed by LCMS and $^1$H NMR.

LC-MS m/z=634 (M+H)$^+$ $^1$H NMR (300 MHz, CDCl$_3$) δ=8.63 (br s, 1H), 8.35-8.22 (m, 3H), 8.07-7.85 (m, 4H), 7.68-7.41 (m, 7H), 7.22 (br s, 1H), 7.06 (br s, 1H), 3.20 (d, 2H), 1.84-1.82 (m, 1H), 0.90 (d, 6H).

Synthesis Example 15: Synthesis of Compound 15

Compound 15 was synthesized according to Reaction Scheme 15 below:

Reaction Scheme 15

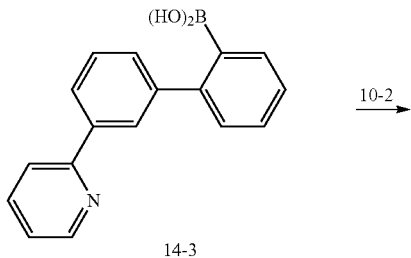

14-3

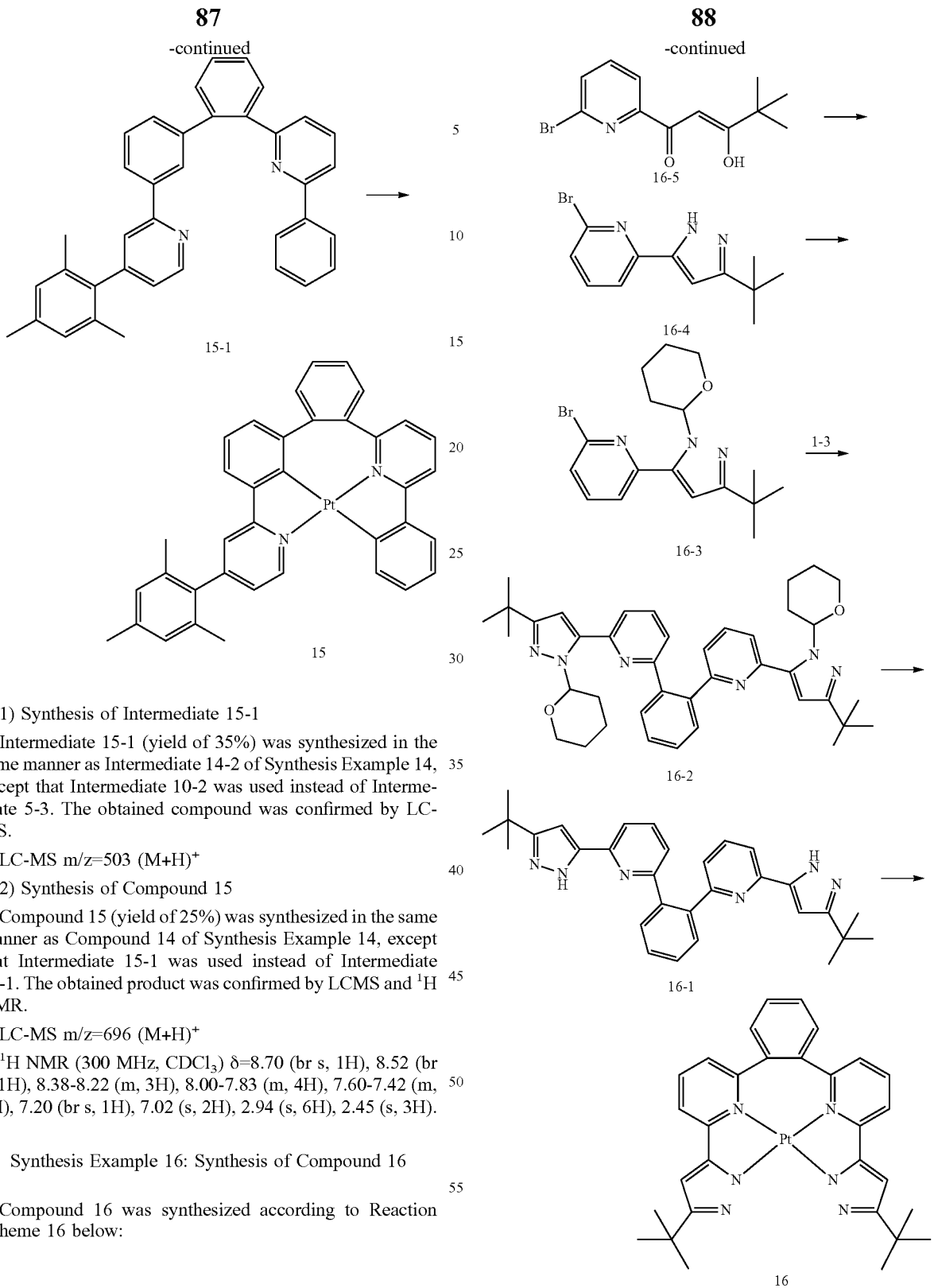

1) Synthesis of Intermediate 15-1

Intermediate 15-1 (yield of 35%) was synthesized in the same manner as Intermediate 14-2 of Synthesis Example 14, except that Intermediate 10-2 was used instead of Intermediate 5-3. The obtained compound was confirmed by LC-MS.

LC-MS m/z=503 (M+H)+

2) Synthesis of Compound 15

Compound 15 (yield of 25%) was synthesized in the same manner as Compound 14 of Synthesis Example 14, except that Intermediate 15-1 was used instead of Intermediate 14-1. The obtained product was confirmed by LCMS and $^1$H NMR.

LC-MS m/z=696 (M+H)+

$^1$H NMR (300 MHz, CDCl$_3$) δ=8.70 (br s, 1H), 8.52 (br s, 1H), 8.38-8.22 (m, 3H), 8.00-7.83 (m, 4H), 7.60-7.42 (m, 7H), 7.20 (br s, 1H), 7.02 (s, 2H), 2.94 (s, 6H), 2.45 (s, 3H).

Synthesis Example 16: Synthesis of Compound 16

Compound 16 was synthesized according to Reaction Scheme 16 below:

1) Synthesis of Intermediate 16-5

1.05 g (26.1 mmol) of NaH was added to 150 ml of anhydrous tetrahydrofuran, and then 2.1 g (21.72 mmol) of dimethyl-2-butanone was added thereto at a temperature of 0° C. and the result was stirred for about 30 minutes. Next, 4.8 g (21.72 mmol) of methyl-6-bromopyridine-2-carboxylate dissolved in 50 ml of anhydrous tetrahydrofuran was slowly added thereto at a temperature of 0° C., and then the result was stirred for about 1 hour. After 1 hour, the result was stirred at a temperature of 80° C. for 18 hours. When the reaction was completed, 50 ml of distilled water was added thereto, and an extraction process was performed three times by adding 200 ml of methylene chloride, thereby obtaining an organic layer. The extracted organic layer was dried with magnesium sulfate and distilled under reduced pressure. The result was separation-purified by column chromatography, thereby obtaining 3.3 g (11.3 mmol, yield of 52%) of Intermediate 16-5. The obtained product was confirmed by LCMS and $^1$H NMR.

LC-MS m/z=284 (M+H)$^+$ $^1$H NMR (300 MHz, CDCl$_3$) δ=8.41-8.39 (m, 1H), 7.92-7.76 (m, 2H), 6.81 (s, 1H), 1.15 (s, 9H)

2) Synthesis of Intermediate 16-4

3.3 g (11.3 mmol) Intermediate 16-5 was dissolved in 30 ml of ethanol, and then 57 ml (57.0 mmol) of hydrazine hydrate was added thereto, and the result was refluxed while heating for about 24 hours. When the reaction was completed, the result was neutralized with 4 M aqueous hydrochloric acid, and concentrated in a vacuum evaporator. 100 ml of distilled water and 200 ml of methylene chloride were added to the concentrated Compound for an extraction process. The extracted organic layer was dried with magnesium sulfate and distilled under reduced pressure. The result was separation-purified by column chromatography 1.8 g (6.9 mmol, yield of 60%) of Intermediate 16-4. The obtained product was confirmed by LCMS and $^1$H NMR.

LC-MS m/z=281 (M+H)$^+$

3) Synthesis of Intermediate 16-3

1.8 g (6.9 mmol) of Intermediate 16-4 was dissolved in 80 ml of toluene, and then 0.6 g (7.2 mmol) of 3,4-dihydro-2H-pyran and 26 microliters (μl) (0.3 mmol) of trifluoroacetic acid were added thereto and the result was refluxed while heating for about 24 hours. When the reaction was completed, the result was distilled under reduced pressure, and the obtained Compound was extracted by adding 300 ml of dichloromethane and 100 ml of brine. The extracted organic layer was dried with magnesium sulfate and distilled under reduced pressure. The result was separation-purified by column chromatography, thereby obtaining about 2.4 g (6.6 mmol, yield of 95%) of Intermediate 16-3. The obtained compound was confirmed by LC-MS.

LC-MS m/z=364 (M+H)$^+$

4) Synthesis of Intermediate 16-2

Intermediate 16-2 (yield of 62%) was synthesized in the same manner as Compound 12-1 of Synthesis Example 12, except that Intermediate 16-3 was used instead of Intermediate 12-2. The obtained compound was confirmed by LC-MS.

LC-MS m/z=645 (M+H)$^+$

5) Synthesis of Intermediate 16-1

1.25 g (1.9 mmol) of Intermediate 16-2 was dissolved in 50 ml of 1,4-dioxane 50 ml, and then 4.8 ml (9.5 mmol) of 2.0 N HCl in ether was added thereto and the result was stirred at room temperature for about 18 hours. When the reaction was completed, the result was distilled under reduced pressure, and the obtained Compound was extracted by adding 100 ml of dichloromethane and 50 ml of saturated sodium hydrogen carbonate aqueous solution. The extracted organic layer was dried with magnesium sulfate and distilled under reduced pressure. The result was separation-purified by column chromatography, thereby obtaining about 0.9 g (1.8 mmol, yield of 95%) of Intermediate 16-1. The obtained compound was confirmed by LC-MS.

LC-MS m/z=477 (M+H)$^+$

6) Synthesis of Compound 16

0.09 g (3.6 mmol) of NaH was dissolved in 20 ml of anhydrous N,N-dimethylformamide (DMF), and then 0.8 g (1.8 mmol) of Intermediate 16-1 was slowly added thereto at a temperature of 0° C. and the result was stirred at room temperature for about 1 hour. Next, 0.75 g (1.8 mmol) of K$_2$PtCl$_4$ dissolved in 10 ml of distilled water was slowly added thereto at room temperature and the result was stirred at a temperature of 100° C. for 24 hours. After 24 hours, the result was cooled to room temperature, and dichloromethane and water were added for an extraction process. The extracted organic layer was dried with magnesium sulfate and separation-purified by column chromatography, thereby obtaining about 0.5 g (0.8 mmol, yield of 43%) of Compound 16.

LC-MS m/z=670 (M+H)$^+$ $^1$H NMR (300 MHz, CDCl$_3$) δ=8.31 (br s, 2H), 7.71 (br s, 2H), 7.45-7.38 (m, 6H), 6.29 (s, 2H), 1.40 (s, 18H).

Synthesis Example 17: Synthesis of Compound 17

Compound 17 was synthesized according to Reaction Scheme 17 below:

Reaction Scheme 17

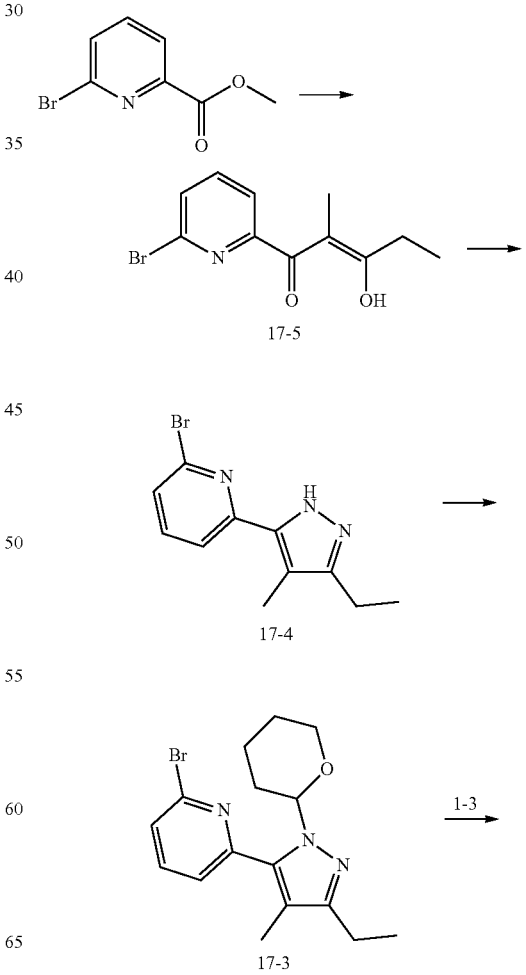

-continued

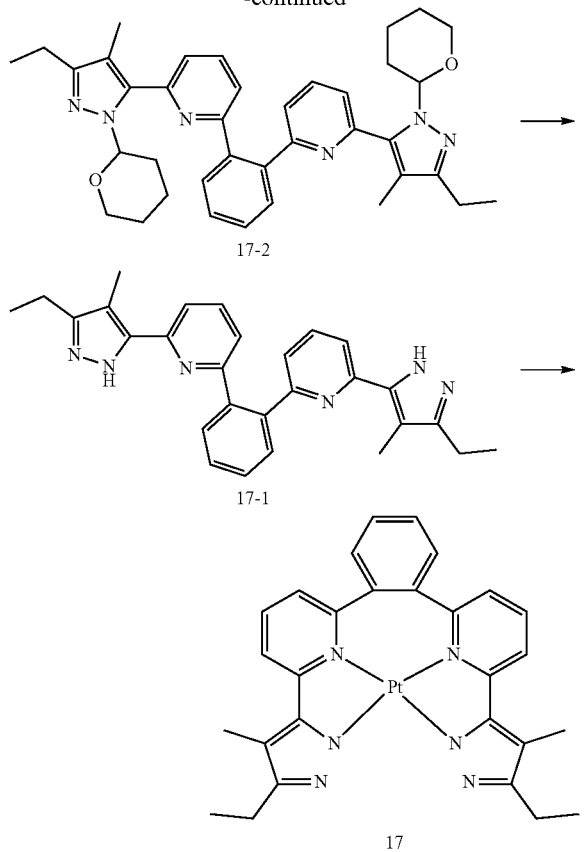

17-2

17-1

17

1) Synthesis of Intermediate 17-5

Intermediate 17-5 (yield of 60%) was synthesized in the same manner as Compound 16-5 of Synthesis Example 16, except that 3-pentanone was used instead of dimethyl-2-butanone. The obtained compound was confirmed by LC-MS.

LC-MS m/z=270 (M+H)$^+$

2) Synthesis of Intermediate 17-4

Intermediate 17-4 (yield of 60%) was synthesized in the same manner as Compound 16-4 of Synthesis Example 16, except that Intermediate 17-5 was used instead of Intermediate 16-5. The obtained compound was confirmed by LC-MS.

LC-MS m/z=266 (M+H)$^+$

3) Synthesis of Intermediate 17-3

Intermediate 17-3 (yield of ~100%) was synthesized in the same manner as Compound 16-4 of Synthesis Example 16, except that Intermediate 17-4 was used instead of Intermediate 16-4. The obtained compound was confirmed by LC-MS.

LC-MS m/z=350 (M+H)$^+$

4) Synthesis of Intermediate 17-2

Intermediate 17-2 (yield of 55%) was synthesized in the same manner as Compound 12-1 of Synthesis Example 12, except that Intermediate 17-3 was used instead of Intermediate 12-2. The obtained compound was confirmed by LC-MS.

LC-MS m/z=617 (M+H)$^+$

5) Synthesis of Intermediate 17-1

Intermediate 17-1 (yield of ~100%) was synthesized in the same manner as Compound 16-1 in Synthesis Example 16, except that Intermediate 17-2 was used instead of Intermediate 16-2. The obtained compound was confirmed by LC-MS.

LC-MS m/z=449 (M+H)$^+$

6) Synthesis of Compound 17

Compound 17 (yield of 40%) was synthesized in the same manner as used to synthesize Compound 16 in Synthesis Example 16, except that Intermediate 17-1 was used instead of Intermediate 16-1.

LC-MS m/z=642 (M+H)$^+$ $^1$H NMR (300 MHz, CDCl$_3$) δ=8.33 (br s, 2H), 7.72 (br s, 2H), 7.44-7.35 (m, 6H), 2.84 (q, 4H), 2.06 (s, 6H), 1.19 (t, 6H).

Synthesis Example 18: Synthesis of Compound 18

Compound 18 was synthesized according to Reaction Scheme 18 below:

Reaction Scheme 18

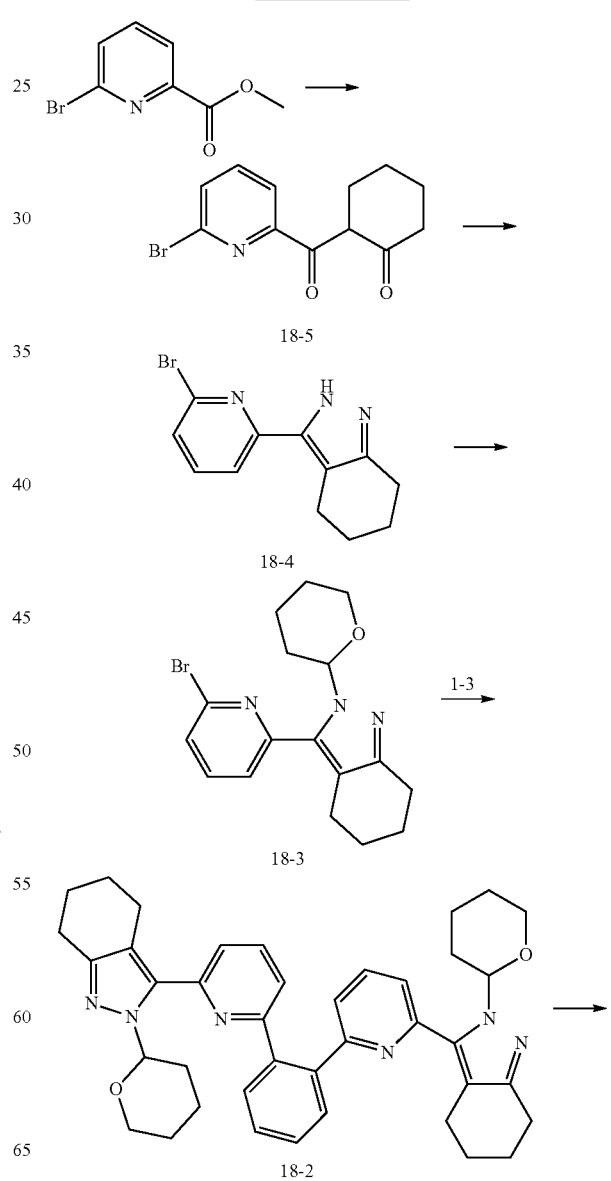

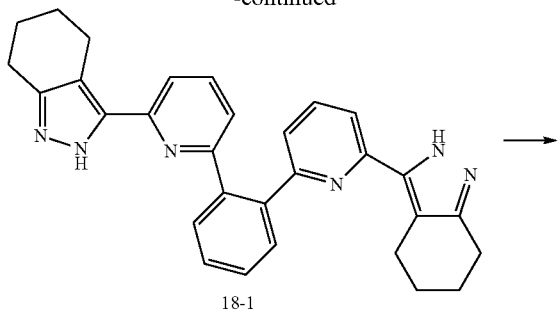

18-1

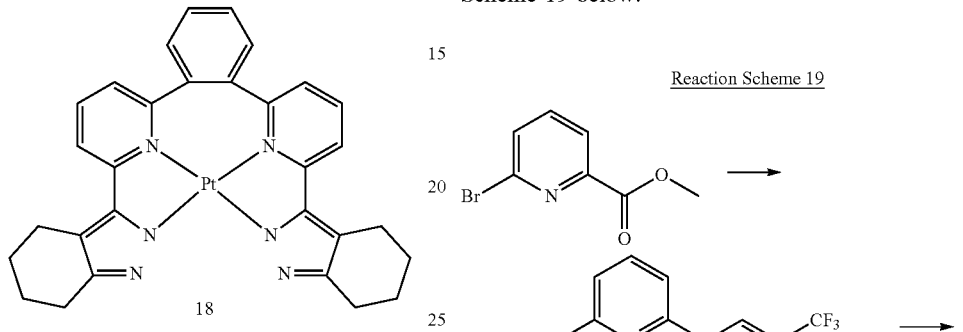

18

1) Synthesis of Intermediate 18-5

Intermediate 18-5 (yield of 42%) was synthesized in the same manner as Compound 16-5 in Synthesis Example 16, except that cyclohexanone was used instead of dimethyl-2-butanone.

The obtained compound was confirmed by LC-MS.

LC-MS m/z=282 (M+H)$^+$

2) Synthesis of Intermediate 18-4

Intermediate 18-4 (yield of 55%) was synthesized in the same manner as Compound 16-4 in Synthesis Example 16, except that Intermediate 18-5 was used instead of Intermediate 16-5. The obtained compound was confirmed by LC-MS.

LC-MS m/z=278 (M+H)$^+$

3) Synthesis of Intermediate 18-3

Intermediate 18-3 (yield of 99%) was synthesized in the same manner as Compound 16-3 in Synthesis Example 16, except that Intermediate 18-4 was used instead of Intermediate 16-4. The obtained compound was confirmed by LC-MS.

LC-MS m/z=362 (M+H)$^+$

4) Synthesis of Intermediate 18-2

Intermediate 18-2 (yield of 55%) was synthesized in the same manner as Compound 12-1 in Synthesis Example 12, except that Intermediate 18-3 was used instead of Intermediate 12-2. The obtained compound was confirmed by LC-MS.

LC-MS m/z=641 (M+H)$^+$

5) Synthesis of Intermediate 18-1

Intermediate 18-1 (yield of ~100%) was synthesized in the same manner as Compound 16-1 in Synthesis Example 16, except that Intermediate 18-2 was used instead of Intermediate 16-2. The obtained compound was confirmed by LC-MS.

LC-MS m/z=473 (M+H)$^+$

6) Synthesis of Compound 18

Intermediate 17-1 was used instead of Intermediate 16-1, and the result was stirred at a temperature of 100° C. for 24 hours and then cooled to room temperature. The solid obtained from the process was filtered and washed with methanol, thereby obtaining Compound 18 (yield of 50%). The obtained Compound 18 was sublimation-purified.

LC-MS m/z=666 (M+H)$^+$ $^1$H NMR (300 MHz, CDCl$_3$) δ=8.31 (d, 2H), 7.68 (br s, 2H), 7.51-7.44 (m, 6H), 2.53-2.50 (m, 8H), 1.91-1.88 (m, 8H).

Synthesis Example 19: Synthesis of Compound 19

Compound 19 was synthesized according to Reaction Scheme 19 below:

Reaction Scheme 19

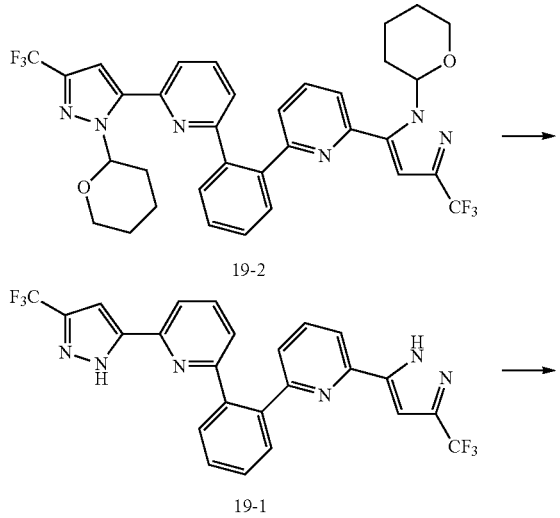

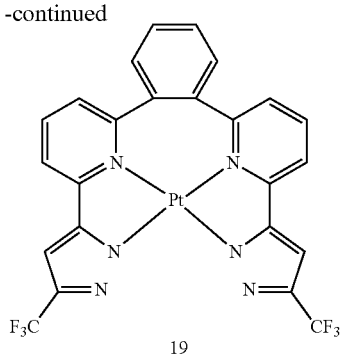

19

1) Synthesis of Intermediate 19-5

Intermediate 19-5 (yield of 55%) was synthesized in the same manner as Compound 16-5 in Synthesis Example 16, except that 1,1,1-trifluoroacetone was used instead of dimethyl-2-butanone. The obtained compound was confirmed by LC-MS.

LC-MS m/z=296 (M+H)+

2) Synthesis of Intermediate 19-4

Intermediate 19-4 (yield of 55%) was synthesized in the same manner as Compound 16-4 in Synthesis Example 16, except that Intermediate 19-5 was used instead of Intermediate 16-5. The obtained compound was confirmed by LC-MS.

LC-MS m/z=292 (M+H)+

3) Synthesis of Intermediate 19-3

Intermediate 19-3 (yield of 95%) was synthesized in the same manner as Compound 16-3 in Synthesis Example 16, except that Intermediate 19-4 was used instead of Intermediate 16-4. The obtained compound was confirmed by LC-MS.

LC-MS m/z=376 (M+H)+

4) Synthesis of Intermediate 19-2

Intermediate 19-2 (yield of 46%) was synthesized in the same manner as Compound 12-1 in Synthesis Example 12, except that Intermediate 19-3 was used instead of Intermediate 12-2. The obtained compound was confirmed by LC-MS.

LC-MS m/z=669 (M+H)+

5) Synthesis of Intermediate 19-1

Intermediate 19-1 (yield of ~98%) was synthesized in the same manner as Compound 16-1 in Synthesis Example 16, except that Intermediate 19-2 was used instead of Intermediate 16-2. The obtained compound was confirmed by LC-MS.

LC-MS m/z=501 (M+H)+

6) Synthesis of Compound 19

Compound 19 (yield of 35%) was synthesized in the same manner as Compound 16 in Synthesis Example 16, except that Intermediate 19-1 was used instead of Intermediate 16-1.

LC-MS m/z=694 (M+H)+

1H NMR (300 MHz, CDCl3) δ=8.33 (br s, 2H), 7.65 (br s, 2H), 7.57-7.50 (m, 6H), 6.21 (s, 2H).

Synthesis Example 20: Synthesis of Compound 20

Compound 20 was synthesized according to Reaction Scheme 20 below:

Reaction Scheme 20

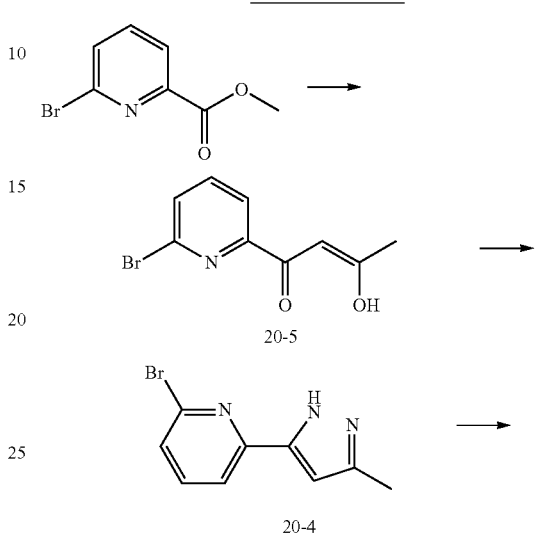

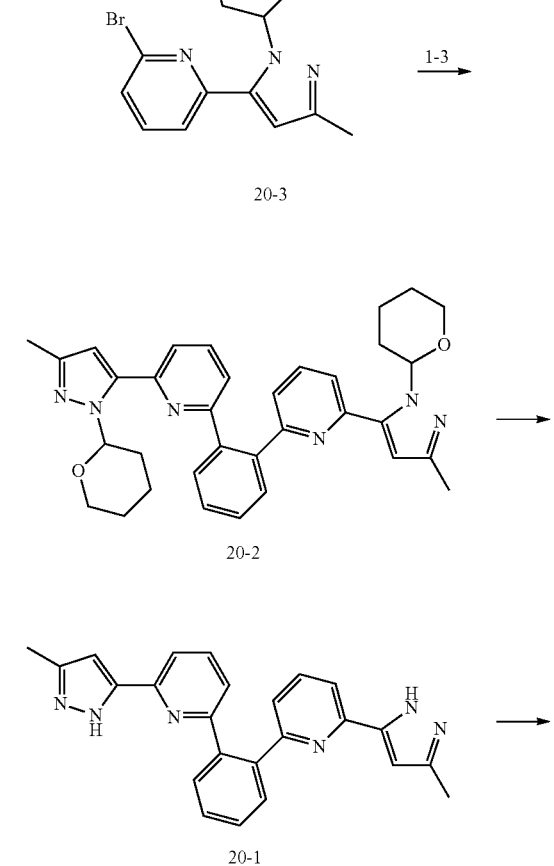

97

-continued

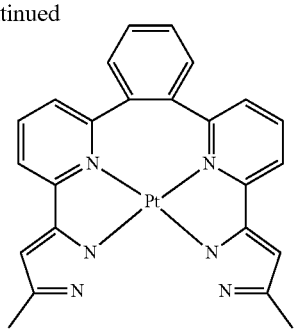

20

1) Synthesis of Intermediate 20-5

4.0 ml (54.5 mmol) of acetone was added to 150 ml of anhydrous tetrahydrofuran, and then 55.0 ml (54.5 mmol) of 1.0 M lithium bis(trimethylsilyl)amide solution was slowly added thereto at a temperature of −78° C. and the result was stirred for about 1 hour. After 1 hour, 9.1 g (42.0 mmol) of methyl-6-bromopyridine-2-carboxylate dissolved in 50 ml of anhydrous tetrahydrofuran was slowly added thereto at a temperature of −78° C., and the result was stirred for about 1 and then stirred at room temperature for about 18 hours. When the reaction was completed, 54.4 mmol of acetic acid (glacial grade) was added thereto and the result was stirred at room temperature for 30 minutes. A small amount of distilled water, which is about 10 ml, and 300 ml of dichloromethane were added for an extraction process. The extracted organic layer was dried with magnesium sulfate and distilled under reduced pressure, thereby obtaining 6.7 g (27.7 mmol, yield of 66%) of Intermediate 20-5 without a purification process. The obtained product was confirmed by LCMS and $^1$H NMR.

LC-MS m/z=242 (M+H)$^+$

2) Synthesis of Intermediate 20-4

Intermediate 20-4 (yield of 61%) was synthesized in the same manner as Compound 16-4 in Synthesis Example 16, except that Intermediate 20-5 was used instead of Intermediate 16-5. The obtained compound was confirmed by LC-MS.

LC-MS m/z=238 (M+H)$^+$

3) Synthesis of Intermediate 20-3

Intermediate 20-3 (yield of 95%) was synthesized in the same manner as Compound 16-3 in Synthesis Example 16, except that Intermediate 20-4 was used instead of Intermediate 16-4. The obtained compound was confirmed by LC-MS.

LC-MS m/z=322 (M+H)$^+$

4) Synthesis of Intermediate 20-2

Intermediate 20-2 (yield of 42%) was synthesized in the same manner as Compound 12-1 in Synthesis Example 12, except that Intermediate 20-3 was used instead of Intermediate 12-2. The obtained compound was confirmed by LC-MS.

LC-MS m/z=561 (M+H)$^+$

5) Synthesis of Intermediate 20-1

Intermediate 20-1 (yield of ~98%) was synthesized in the same manner as Compound 16-1 in Synthesis Example 16, except that Intermediate 20-2 was used instead of Intermediate 16-2. The obtained compound was confirmed by LC-MS.

LC-MS m/z=393 (M+H)$^+$

98

6) Synthesis of Compound 20

Compound 20 (yield of 40%) was synthesized in the same manner as Compound 16 in Synthesis Example 16, except that Intermediate 20-1 was used instead of Intermediate 16-1.

LC-MS m/z=586 (M+H)$^+$ $^1$H NMR (300 MHz, CDCl$_3$) δ=8.30 (d, 2H), 7.68 (br s, 2H), 7.45-7.40 (m, 6H), 6.26 (s, 2H), 2.16 (s, 6H).

Synthesis Example 21: Synthesis of Compound 21

Compound 21 was synthesized according to Reaction Scheme 21 below:

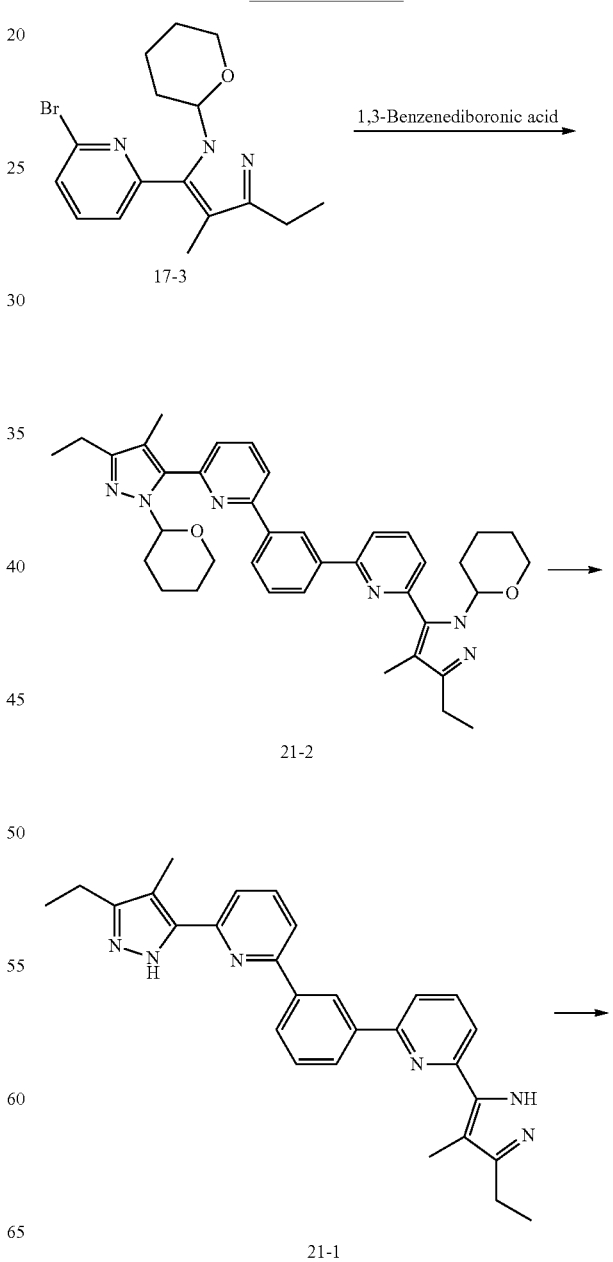

1) Synthesis of Intermediate 21-2

Intermediate 21-2 (yield of 45%) was synthesized in the same manner as Compound 12-1 in Synthesis Example 12, except that Intermediate 17-3 was used instead of Intermediate 12-2. The obtained compound was confirmed by LC-MS.

LC-MS m/z=617 (M+H)+

2) Synthesis of Intermediate 21-1

Intermediate 21-1 (yield of 98%) was synthesized in the same manner as Compound 16-1 in Synthesis Example 16, except that Intermediate 21-2 was used instead of Intermediate 16-2. The obtained compound was confirmed by LC-MS.

LC-MS m/z=449 (M+H)+

3) Synthesis of Compound 21

Compound 21 (yield of 34%) was synthesized in the same manner as Compound 16 in Synthesis Example 16, except that Intermediate 21-1 was used instead of Intermediate 16-1.

LC-MS m/z=642 (M+H)+

$^1$H NMR (300 MHz, CDCl$_3$) δ=8.52 (br s, 1H), 8.13 (d, 2H), 7.81 (br s, 2H), 7.53-7.40 (m, 5H), 2.82 (q, 4H), 2.10 (s, 6H), 1.22 (t, 6H).

Synthesis Example 22: Synthesis of Compound 22

Compound 22 was synthesized according to Reaction Scheme 22 below:

1) Synthesis of Intermediate 22-2

Intermediate 22-2 (yield of 42%) was synthesized in the same manner as Compound 21-2 in Synthesis Example 21, except that Intermediate 18-3 was used instead of Intermediate 17-3. The obtained compound was confirmed by LC-MS.

LC-MS m/z=669 (M+H)+

2) Synthesis of Intermediate 22-1

Intermediate 22-1 (yield of 98%) was synthesized in the same manner as Compound 21-1 in Synthesis Example 21, except that Intermediate 22-2 was used instead of Intermediate 21-2. The obtained compound was confirmed by LC-MS.

LC-MS m/z=501 (M+H)+

3) Synthesis of Compound 22

Compound 22 (yield of 33%) was synthesized in the same manner as Compound 21 in Synthesis Example 21, except that Intermediate 22-1 was used instead of Intermediate 21-1.

LC-MS m/z=694 (M+H)+

$^1$H NMR (300 MHz, CDCl$_3$) δ=8.58 (s, 1H), 8.26 (br s, 2H), 7.91 (br s, 2H), 7.66-7.48 (m, 5H), 6.13 (s, 2H).

Synthesis Example 23: Synthesis of Compound 23

Compound 23 was synthesized according to Reaction Scheme 23 below:

Reaction Scheme 23

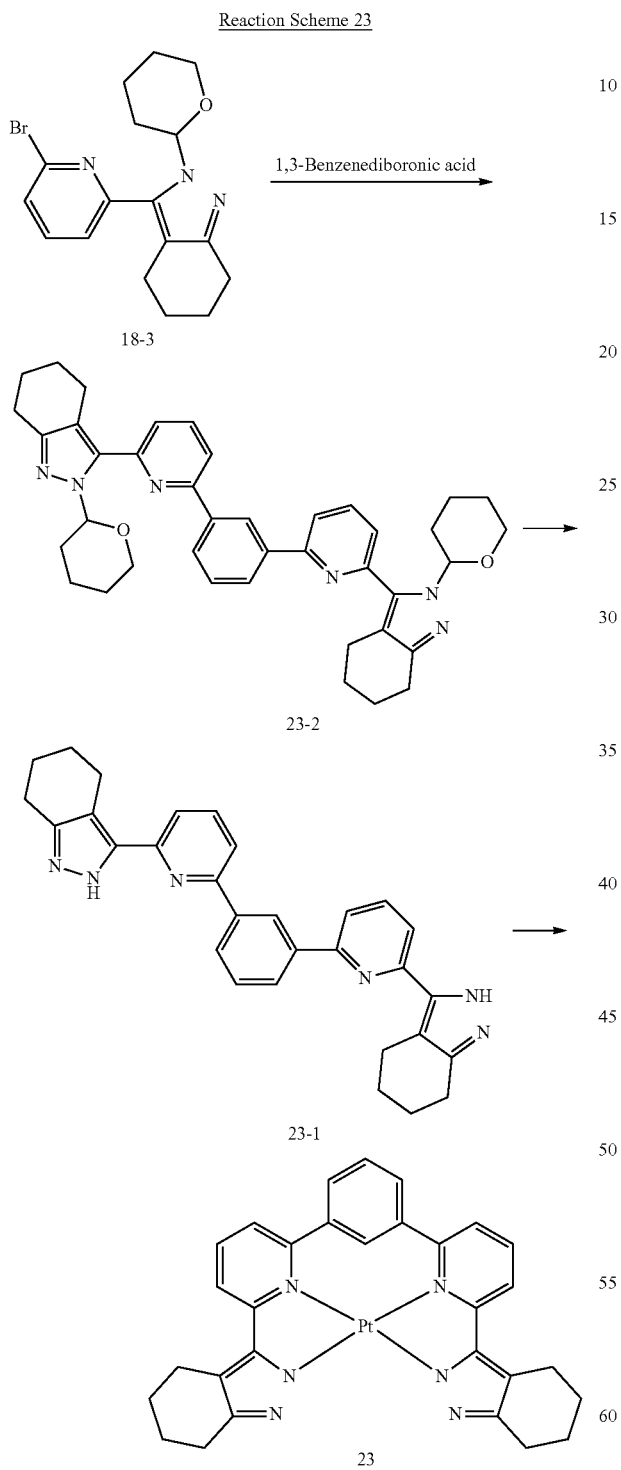

1) Synthesis of Intermediate 23-2

Intermediate 23-2 (yield of 51%) was synthesized in the same manner as Compound 21-2 in Synthesis Example 21, except that Intermediate 18-3 was used instead of Intermediate 17-3. The obtained compound was confirmed by LC-MS.

LC-MS m/z=641 (M+H)$^+$

2) Synthesis of Intermediate 23-1

Intermediate 23-1 (yield of 98%) was synthesized in the same manner as Compound 21-1 in Synthesis Example 21, except that Intermediate 23-2 was used instead of Intermediate 21-2. The obtained compound was confirmed by LC-MS.

LC-MS m/z=473 (M+H)$^+$

3) Synthesis of Compound 23

Compound 23 (yield of 40%) was synthesized in the same manner as Compound 21 in Synthesis Example 21, except that Intermediate 23-1 was used instead of Intermediate 21-1.

LC-MS m/z=666 (M+H)$^+$ $^1$H NMR (300 MHz, CDCl$_3$) δ=8.52 (br s, 2H), 8.13 (br s, 2H), 7.98-7.95 (m, 2H), 7.45-7.39 (m, 5H), 2.55-2.1 (m, 8H), 1.87-1.83 (m, 8H).

Synthesis Example 24: Synthesis of Compound 24

Compound 24 was synthesized according to Reaction Scheme 24 below:

Reaction Scheme 24

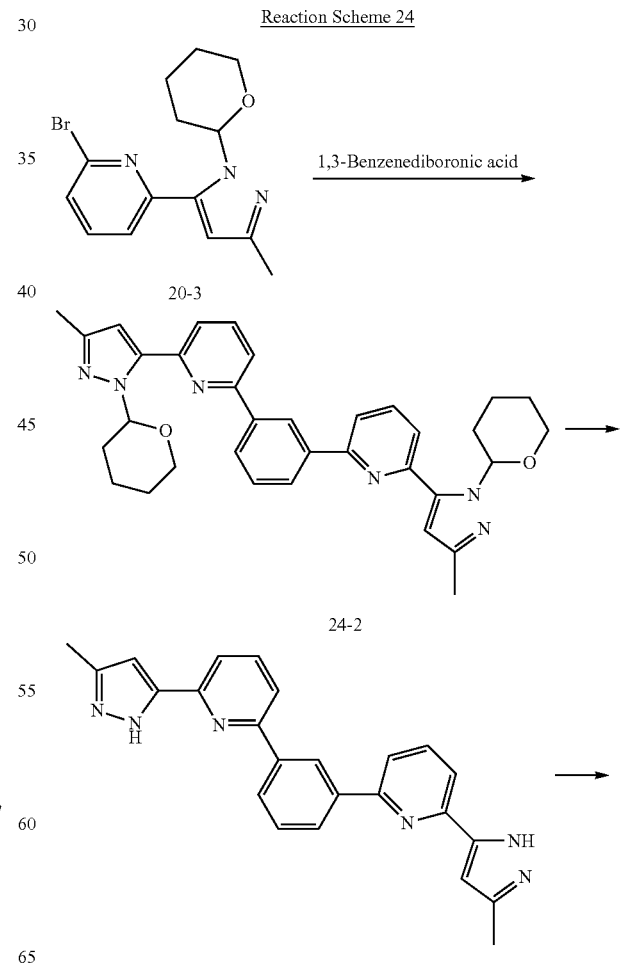

-continued

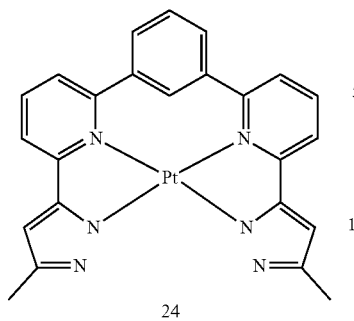

24

1) Synthesis of Intermediate 24-2

Intermediate 24-2 (yield of 38%) was synthesized in the same manner as Compound 21-2 in Synthesis Example 21, except that Intermediate 20-3 was used instead of Intermediate 17-3.

The obtained compound was confirmed by LC-MS.

LC-MS m/z=561 (M+H)$^+$

2) Synthesis of Intermediate 24-1

Intermediate 24-1 (yield of 95%) was synthesized in the same manner as Compound 21-1 in Synthesis Example 21, except that Intermediate 24-2 was used instead of Intermediate 21-2. The obtained compound was confirmed by LC-MS.

LC-MS m/z=393 (M+H)$^+$

3) Synthesis of Compound 24

Compound 24 (yield of 36%) was synthesized in the same manner as Compound 21 in Synthesis Example 21, except that Intermediate 22-1 was used instead of Intermediate 21-1.

LC-MS m/z=586 (M+H)$^+$ $^1$H NMR (300 MHz, CDCl$_3$) δ=8.57 (br s, 1H), 8.30 (br s, 2H), 7.90 (br s, 2H), 7.57-7.45 (m, 5H), 6.15 (s, 2H), 2.27 (s, 6H).

Synthesis Example 25: Synthesis of Compound 25

Compound 25 was synthesized according to Reaction Scheme 25 below:

Reaction Scheme 25

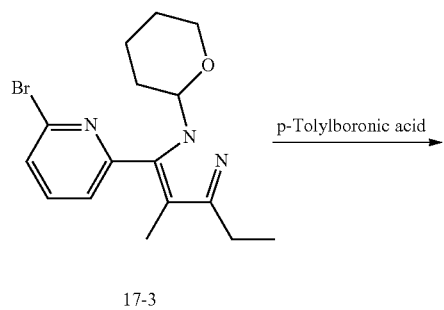

17-3

-continued

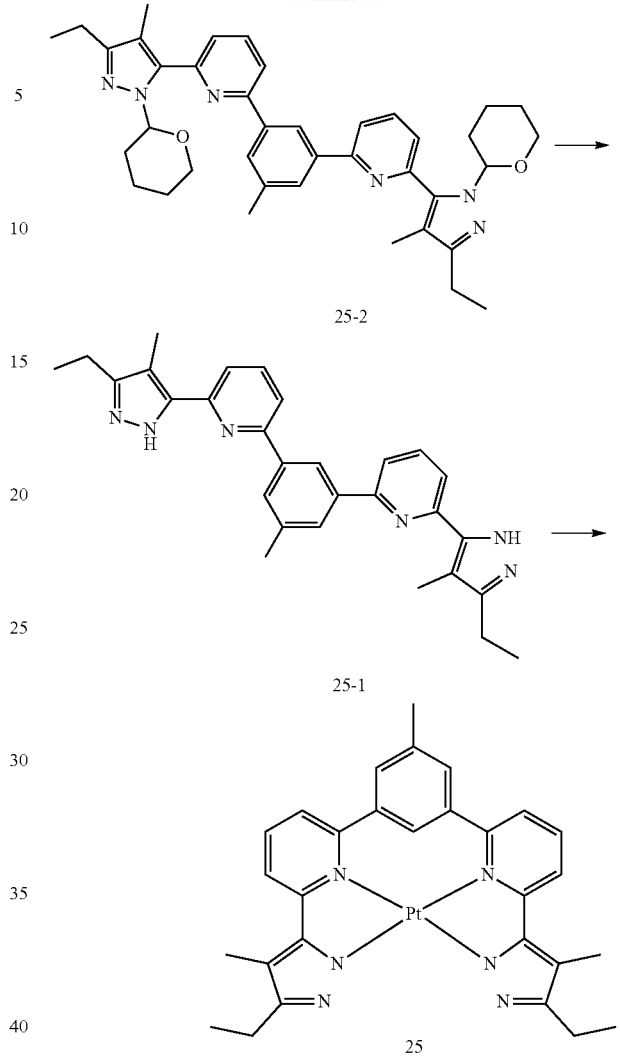

1) Synthesis of Intermediate 25-2

Intermediate 25-2 (yield of 48%) was synthesized in the same manner as Compound 21-2 in Synthesis Example 21, except that p-tolylboronic acid was used instead of 1,3-benzenediboronic acid. The obtained compound was confirmed by LC-MS.

LC-MS m/z=631 (M+H)$^+$

2) Synthesis of Intermediate 25-1

Intermediate 25-1 (yield of 97%) was synthesized in the same manner as Compound 21-1 in Synthesis Example 21, except that Intermediate 25-2 was used instead of Intermediate 21-2. The obtained compound was confirmed by LC-MS.

LC-MS m/z=463 (M+H)$^+$

3) Synthesis of Compound 25

Compound 25 (yield of 33%) was synthesized in the same manner as Compound 21 in Synthesis Example 21, except that Intermediate 25-1 was used instead of Intermediate 21-1.

LC-MS m/z=656 (M+H)$^+$ $^1$H NMR (300 MHz, CDCl$_3$) δ=8.50 (s, 1H), 8.18 (s, 2H), 7.73-7.70 (m, 2H), 7.55-7.44 (m, 4H), 2.83 (q, 4H), 2.33 (s, 3H), 2.09 (s, 6H), 1.20 (t, 6H).

Synthesis Example 26: Synthesis of Compound 26

Compound 26 was synthesized according to Reaction Scheme 26 below:

Reaction Scheme 26

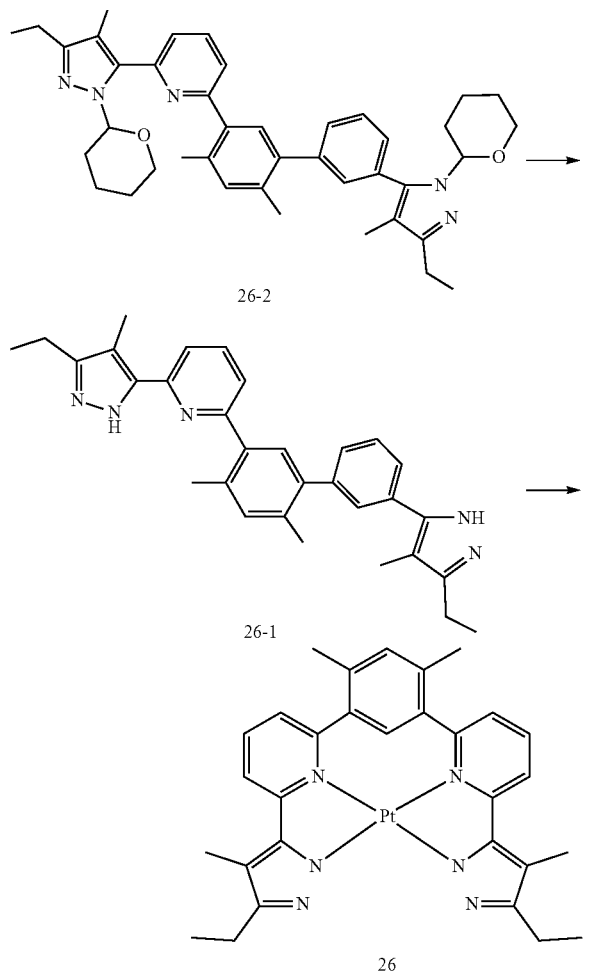

1) Synthesis of Intermediate 26-2

Intermediate 26-2 (yield of 45%) was synthesized in the same manner as Compound 21-2 in Synthesis Example 21, except that 3,5-dimethylphenylboronic acid was used instead of 1,3-benzenediboronic acid. The obtained compound was confirmed by LC-MS.

LC-MS m/z=645 (M+H)$^+$

2) Synthesis of Intermediate 26-1

Intermediate 26-1 (yield of 97%) was synthesized in the same manner as Compound 21-1 in Synthesis Example 21, except that Intermediate 25-2 was used instead of Intermediate 21-2. The obtained compound was confirmed by LC-MS.

LC-MS m/z=477 (M+H)$^+$

3) Synthesis of Compound 26

Compound 26 (yield of 35%) was synthesized in the same manner as Compound 21 in Synthesis Example 21, except that Intermediate 26-1 was used instead of Intermediate 21-1.

LC-MS m/z=670 (M+H)$^+$ $^1$H NMR (300 MHz, CDCl$_3$) δ=8.55 (br s, 1H), 7.76-7.72 (m, 2H), 7.52-7.31 (m, 6H), 2.85 (q, 4H), 2.38 (s, 6H), 2.12 (s, 6H), 1.22 (t, 6H).

Synthesis Example 27: Synthesis of Compound 27

Compound 27 was synthesized according to Reaction Scheme 27 below:

Reaction Scheme 27

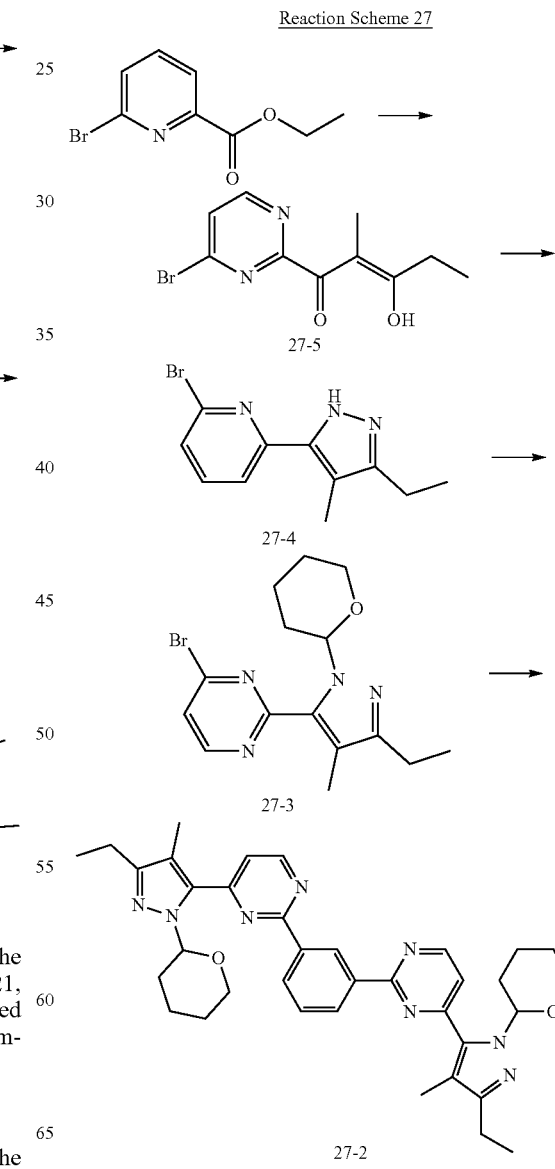

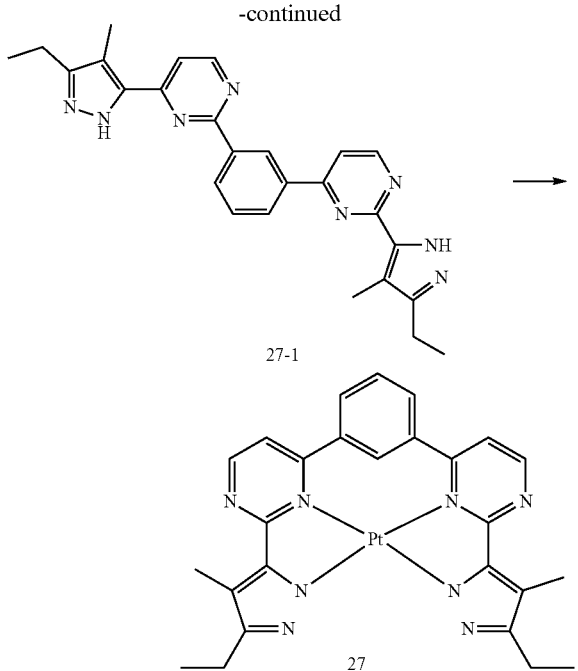

27-1

27

1) Synthesis of Intermediate 27-5

3.0 g (34.8 mmol) of 3-pentanone was added to 150 ml of anhydrous tetrahydrofuran, and then 35 ml (35.0 mmol) of 1.0 M LiHMDS in THF was slowly added thereto at a temperature of −78° C. and the result was stirred for about 1 hour. Next, 6.2 g (26.8 mmol) of ethyl 4-bromopyrimidine-2-carboxylate dissolved in anhydrous tetrahydrofuran was slowly added thereto at a temperature of −78° C., and the result was stirred for about 1 hour. After 1 hour, the result was stirred at room temperature for 24 hours. When the reaction was completed, 2 ml of acetic acid (glacial grade) 2 ml was added thereto and the result was stirred for about 30 minutes. After 30 minutes, 10 ml of distilled water and 200 ml of methylene chloride were added thereto for an extraction process. Then, the extracted organic layer was dried with magnesium sulfate and distilled under reduced pressure. The result was separation-purified by column chromatography, thereby obtaining 3.5 g (12.9 mmol, yield of 48%) of Intermediate 27-5. The obtained compound was confirmed by LC-MS.

LC-MS m/z=271 (M+H)$^+$

2) Synthesis of Intermediate 27-4

Intermediate 27-4 (yield of 55%) was synthesized in the same manner as Compound 16-4 in Synthesis Example 16, except that Intermediate 27-5 was used instead of Intermediate 16-5.

The obtained compound was confirmed by LC-MS.

LC-MS m/z=267 (M+H)$^+$

3) Synthesis of Intermediate 27-3

Intermediate 27-3 (yield of 98%) was synthesized in the same manner as Compound 16-3 in Synthesis Example 16, except that Intermediate 27-4 was used instead of Intermediate 16-4.

The obtained compound was confirmed by LC-MS.

LC-MS m/z=351 (M+H)$^+$

4) Synthesis of Intermediate 27-2

Intermediate 27-2 (yield of 40%) was synthesized in the same manner as Compound 21-2 in Synthesis Example 21, except that Intermediate 27-3 was used instead of Intermediate 21-3. The obtained compound was confirmed by LC-MS.

LC-MS m/z=619 (M+H)$^+$

5) Synthesis of Intermediate 27-1

Intermediate 27-1 (yield of 98%) was synthesized in the same manner as Compound 21-1 in Synthesis Example 21, except that Intermediate 27-2 was used instead of Intermediate 21-2. The obtained compound was confirmed by LC-MS.

LC-MS m/z=451 (M+H)$^+$

6) Synthesis of Compound 27

Compound 27 (yield of 30%) was synthesized in the same manner as Compound 21 in Synthesis Example 21, except that Intermediate 27-1 was used instead of Intermediate 21-1. LC-MS m/z=644 (M+H)$^+$ $^1$H NMR (300 MHz, CDCl$_3$) δ=8.66 (d, 1H), 8.10 (d, 2H), 8.02-7.99 (m, 3H), 7.41 (br s, 1H), 2.81 (q, 4H), 2.12 (s, 6H), 1.26 (t, 6H).

Synthesis Example 28: Synthesis of Compound 28

Compound 28 was synthesized according to Reaction Scheme 28 below:

Reaction Scheme 28

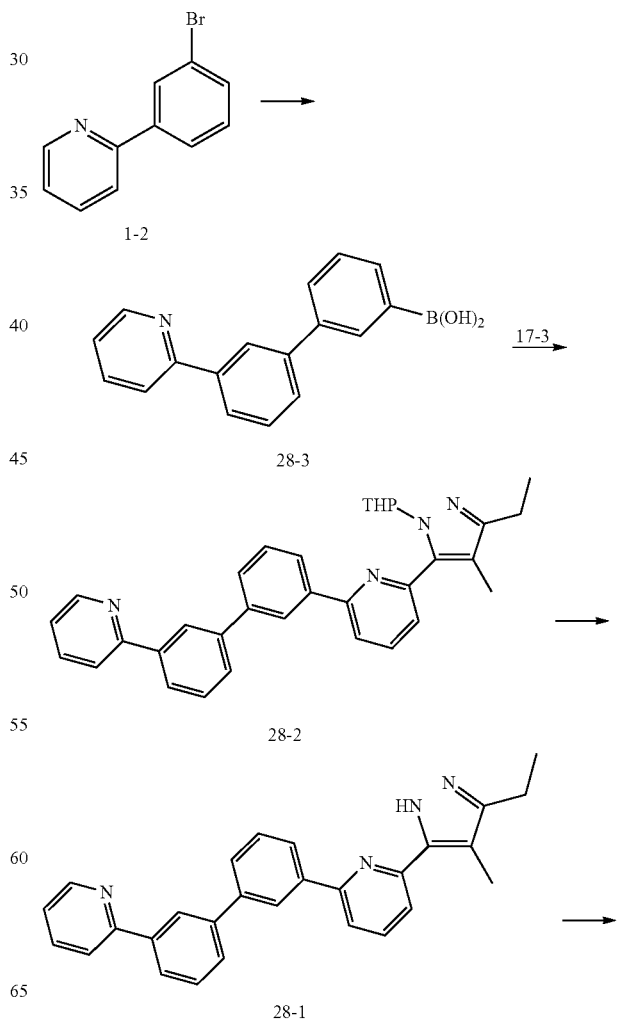

1-2

28-3

28-2

28-1

109

-continued

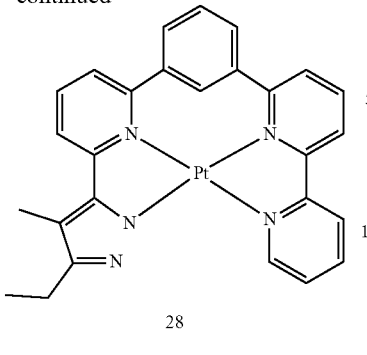

28

1) Synthesis of Intermediate 28-3

5.0 g (21.4 mmol) of Intermediate 1-2 was dissolved in 200 ml of ethanol, and then 1.2 g (1.1 mmol) tetrakistriphenylphosphine Pd(0) was added thereto at room temperature and the result was stirred for about 5 minutes. Next, 3.6 g (21.4 mmol) of 1,3-benzenediboronic acid and 8.9 g (64.2 mmol) of potassium carbonate were added thereto. Then, 10 ml of distilled water was added thereto and the result was stirred at a temperature of 50° C. for two days. When the reaction was completed, the result was distilled under reduced pressure and the obtained Compound was extracted by adding 300 ml of dichloromethane 300 ml and 50 ml of distilled water. The extracted organic layer was dried with magnesium sulfate and distilled under reduced pressure, thereby obtaining about 3.8 g (13.9 mmol, yield of 65%) of Intermediate 28-2 without a purification process. The obtained compound was confirmed by LC-MS.

LC-MS m/z=276 (M+H)$^+$

2) Synthesis of Intermediate 28-2

Intermediate 28-2 (yield of 65%) was synthesized in the same manner as Compound 14-2 in Synthesis Example 14, except that Intermediate 28-3 was used instead of Intermediate 14-3, and Intermediate 17-3 was used instead of Intermediate 5-2. The obtained compound was confirmed by LC-MS.

LC-MS m/z=501 (M+H)$^+$

3) Synthesis of Intermediate 28-1

Intermediate 28-1 (yield of 98%) was synthesized in the same manner as Compound 21-1 in Synthesis Example 21, except that Intermediate 28-2 was used instead of Intermediate 21-2. The obtained compound was confirmed by LC-MS.

LC-MS m/z=417 (M+H)$^+$

4) Synthesis of Compound 28

0.03 g (1.3 mmol) of NaH was dissolved in 20 ml of anhydrous N,N-dimethylformamide (DMF), and then 0.5 g (1.2 mmol) of Intermediate 28-1 was slowly added thereto at a temperature of 0° C. and the result was stirred at room temperature for about 1 hour. Next, 0.75 g (1.8 mmol) of K$_2$PtCl$_4$ dissolved in 10 ml of distilled water was slowly added thereto, and then the result was stirred at a temperature of 100° C. for 6 hours and refluxed while heating for 24 hours. Then, the result was cooled to room temperature, and the obtained solid was filtered and washed with ether and ethanol. The solid obtained from the above process was sublimation-purified, thereby obtaining about 0.1 g (0.16 mmol, yield of 13%) of Compound 28.

LC-MS m/z=610 (M+H)$^+$

110

Synthesis Example 29: Synthesis of Compound 29

Compound 29 was synthesized according to Reaction Scheme 29 below:

Reaction Scheme 29

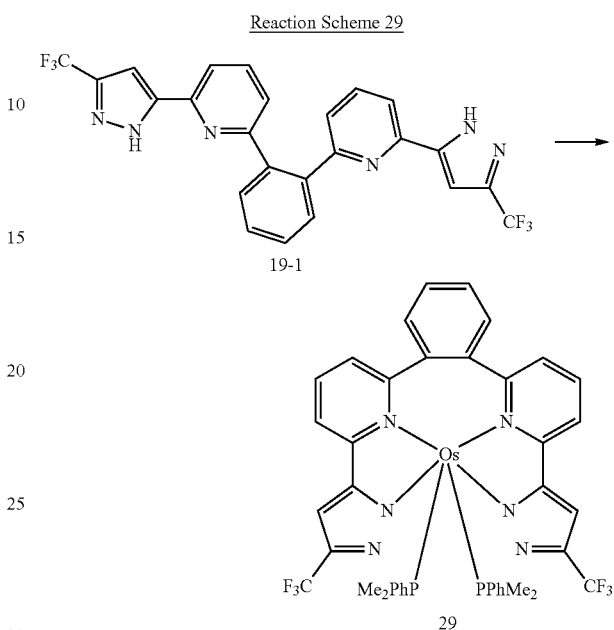

29

1) Synthesis of Compound 29

3.0 g (6.0 mmol) of Intermediate 19-1 was dissolved in 40 ml of diethylene glycol monoethyl ether, and then 0.9 g (1.0 mmol) of Os$_3$(CO)$_{12}$ was added thereto and the result was stirred at a temperature of 180° C. for 24 hours. Then, the result was cooled to a temperature of 140° C.; 0.4 g (5.0 mmol) of trimethylamine N-oxide was added thereto; and the result was stirred at a temperature of 180° C. for 5 minutes. After 5 minutes, 5.0 mmol of dimethyl(phenyl) phosphine (PPhMe$_2$) was added thereto and the result was stirred for 24 hours. When the reaction was completed, 80 ml of distilled water was added to the reaction solution and then, 200 ml of ethyl acetate was added thereto, followed by an extraction process. The extracted organic layer was dried with magnesium sulfate and distilled under reduced pressure. The result was separation-purified by column chromatography and then sublimation-purified, thereby obtaining 3.0 g (3.1 mmol, yield of 52%) of Compound 29.

LC-MS m/z=967 (M+H)$^+$ $^1$H NMR (300 MHz, CDCl$_3$) δ=9.35 (br s, 2H), 9.02 (br s, 2H), 8.75-8.68 (m, 6H), 7.65-7.52 (m, 6H), 7.28-7.22 (m, 4H), 6.51 (s, 2H), 0.81 (m, 6H), 0.60 (m, 6H).

Example 1

An anode was prepared by cutting a substrate with ITO/Ag/ITO having a thickness of 70/1,000/70 Å deposited thereon to a size of 50 mm×50 mm×0.7 mm, ultrasonically cleaning the glass substrate by using isopropyl alcohol and pure water for 5 minutes each, and then irradiating UV light for 30 minutes thereto and exposing to ozone to clean. Then, the anode was loaded into a vacuum deposition apparatus.

By vacuum-depositing 2-TNATA on the glass substrate, a hole injection layer having a thickness of 600 Å was formed, and then by vacuum-depositing NPB, a hole transport layer having a thickness of 1,000 Å was formed.

CBP and Compound 1 were co-deposited on the upper portion of the hole transport layer in a weight ratio of 91:9, thereby forming an emission layer having a thickness of 250 Å. BCP was vacuum-deposited on the upper portion of the emission layer, and thus a hole blocking layer having a thickness of 50 Å was formed. Alq3 was deposited on the upper portion of the hole blocking layer, and thus an electron transport layer having a thickness of 350 Å was formed. LiF was vacuum-deposited on the upper portion of the electron transport layer, and thus an electron injection layer having a thickness of 10 Å was formed. Then, by vacuum-depositing Mg and Ag on the upper portion of the electron injection layer in a weight ratio of 90:10 and forming an electrode having a thickness of 120 Å, an organic light-emitting device was manufacture.

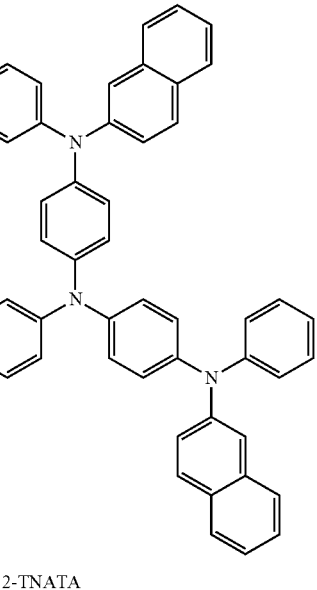

2-TNATA

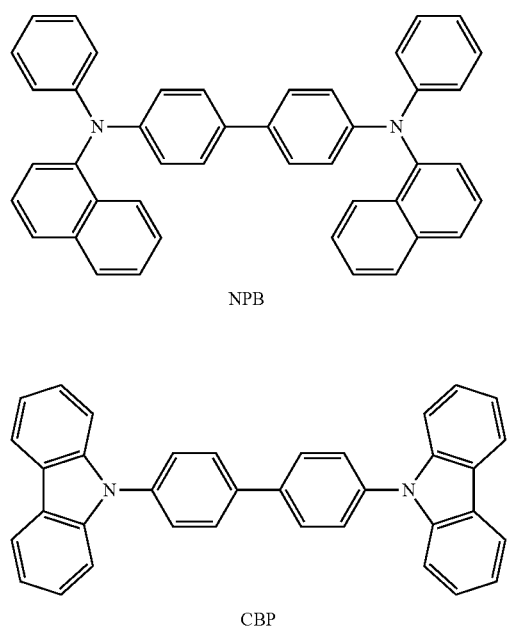

NPB

CBP

-continued

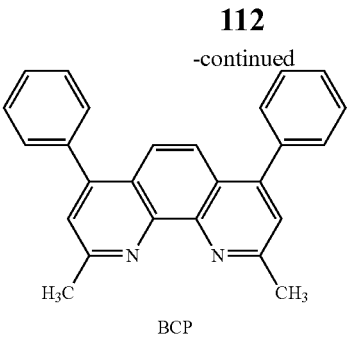

BCP

Example 2

An organic light-emitting device was manufactured in the same manner as in Example 1, except that in forming an emission layer, Compound 3 was used instead of Compound 1.

Example 3

An organic light-emitting device was manufactured in the same manner as in Example 1, except that in forming an emission layer, Compound 5 was used instead of Compound 1.

Example 4

An organic light-emitting device was manufactured in the same manner as in Example 1, except that in forming an emission layer, Compound 7 was used instead of Compound 1.

Example 5

An organic light-emitting device was manufactured in the same manner as in Example 1, except that in forming an emission layer, Compound 8 was used instead of Compound 1.

Example 6

An organic light-emitting device was manufactured in the same manner as in Example 1, except that in forming an emission layer, Compound 9 was used instead of Compound 1.

Example 7

An organic light-emitting device was manufactured in the same manner as in Example 1, except that in forming an emission layer, Compound 12 was used instead of Compound 1.

Example 8

An organic light-emitting device was manufactured in the same manner as in Example 1, except that in forming an emission layer, Compound 17 was used instead of Compound 1.

Example 9

An organic light-emitting device was manufactured in the same manner as in Example 1, except that in forming an emission layer, Compound 27 was used instead of Compound 1.

Example 10

An organic light-emitting device was manufactured in the same manner as in Example 1, except that in forming an emission layer, CBP and Compound 28 were co-deposited in a weight ratio of 94:6 to form an emission layer having a thickness of 400 Å and the thickness of the hole transport layer was changed to 1,350 Å.

Example 11

An organic light-emitting device was manufactured in the same manner as in Example 10, except that in forming an emission layer, Compound 29 was used instead of Compound 28.

Comparative Example 1

An organic light-emitting device was manufactured in the same manner as in Example 1, except that in forming an emission layer, Ir(ppy)$_3$ was used instead of Compound 1.

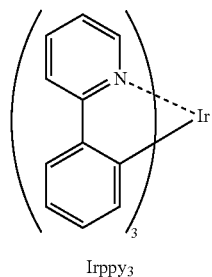

Irppy$_3$

Comparative Example 2

An organic light-emitting device was manufactured in the same manner as in Example 1, except that in forming an emission layer, Compound 1-46 was used instead of Compound 1.

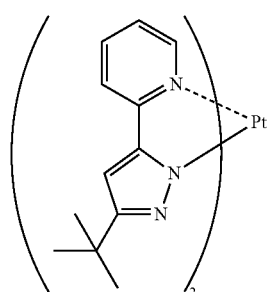

1-46

Comparative Example 3

An organic light-emitting device was manufactured in the same manner as in Example 10, except that in forming an emission layer, PtOEP illustrated below was used instead of Compound 28.

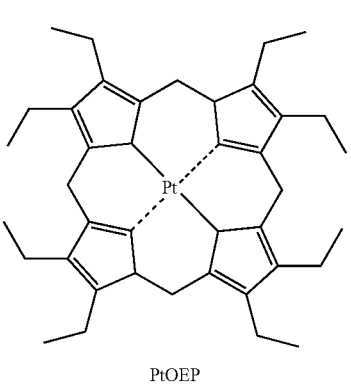

PtOEP

Comparative Example 4

An organic light-emitting device was manufactured in the same manner as in Example 1, except that in forming an emission layer, Compound A illustrated below was used instead of Compound 1.

Compound A

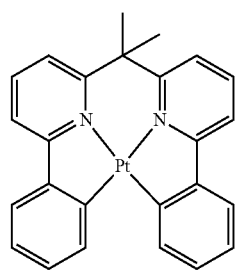

Evaluation Example 1

Driving voltage, current density, brightness, efficiency, emission color, color coordinate and lifespan of Compounds of Examples 1 to 11 and Comparative Examples 1 to 4 were measured, and the results are shown in the Table 1 below. LT$_{97}$ indicates a lifespan, which is a time duration until brightness reduced to 97% of the initial brightness:

TABLE 1

| | Host | Dopant | Driving voltage (V) | Current density (Ma/cm²) | Brightness (cd/m²) | Efficiency (cd/A) | Emission color | Color coordinate | LT₉₇ (HR) |
|---|---|---|---|---|---|---|---|---|---|
| Example 1 | CBP | Compound 1 | 5.5 | 10 | 5,480 | 54.8 | Green | 0.25, 0.70 | 97 |
| Example 2 | CBP | Compound 3 | 5.6 | 10 | 6,371 | 63.7 | Green | 0.24, 0.71 | 90 |
| Example 3 | CBP | Compound 5 | 5.5 | 10 | 6,516 | 65.2 | Green | 0.25, 0.70 | 98 |
| Example 4 | CBP | Compound 7 | 5.6 | 10 | 6,296 | 62.9 | Green | 0.24, 0.71 | 95 |
| Example 5 | CBP | Compound 8 | 5.7 | 10 | 5,864 | 58.6 | Green | 0.23, 0.71 | 87 |
| Example 6 | CBP | Compound 9 | 5.6 | 10 | 6,828 | 68.3 | Green | 0.26, 0.71 | 94 |
| Example 7 | CBP | Compound 12 | 5.8 | 10 | 5,735 | 57.4 | Green | 0.24, 0.70 | 91 |
| Example 8 | CBP | Compound 17 | 5.5 | 10 | 6,738 | 67.4 | Green | 0.23, 0.71 | 90 |
| Example 9 | CBP | Compound 27 | 5.5 | 10 | 6,641 | 66.4 | Green | 0.28, 0.71 | 93 |
| Example 10 | CBP | Compound 28 | 5.6 | 10 | 3,570 | 35.7 | Red | 0.64, 0.33 | 95 |
| Example 11 | CBP | Compound 29 | 5.3 | 10 | 3,487 | 34.8 | Red | 0.63, 0.34 | 110 |
| Comparative Example 1 | CBP | Ir(ppy)₃ | 6.8 | 10 | 4,766 | 47.7 | Green | 0.25, 0.70 | 61 |
| Comparative Example 2 | CBP | 1-46 | 6.0 | 10 | 5,237 | 52.3 | Green | 0.25, 0.73 | 82 |
| Comparative Example 3 | CBP | PtOEP | 7.3 | 10 | 2,212 | 22.1 | Red | 0.67, 0.32 | 89 |
| Comparative Example 4 | CBP | Compound A | 6.3 | 10 | 5,014 | 50.1 | Green | 0.29, 0.68 | 88 |

Compounds having a structure represented by Formula 1 according to an embodiment were used in a top-emission type organic light-emitting device as a material for a green dopant phosphorescent dopant and a red phosphorescent dopant. As a result, driving voltage was decreased by 0.5 volts (V) to 2.0 V; efficiency and lifespan was significantly improved to have an I-V-L characteristic; brightness was also improved compared to Ir(ppy)₃, 1-46, PtOEP, and Compound A.

In Example 1, Compound according to embodiment was used as a green phosphorescent dopant, and thus driving voltage was decreased by 1.3 V or greater; efficiency was increased by about 15%; and lifespan was increased by about 60% compared to Comparative Example 1. Driving voltage was decreased by 0.5 V or greater; efficiency was increased by about 5%; and lifespan was increased by about 20% compared to Comparative Example 2.

In Example 11, Compound according to embodiment was used as a red phosphorescent dopant, and thus driving voltage was decreased by 2.0 V or greater; efficiency was increased by about 55%; and lifespan was increased by about 20% compared to Comparative Example 3.

As described above, according to the one or more of the above embodiments, the organometallic compound has excellent electric characteristics and thermal stability. Accordingly, an organic light-emitting device including the organometallic compound may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the present disclosure as defined by the following claims.

What is claimed is:

1. An organometallic compound represented by Formula 1:

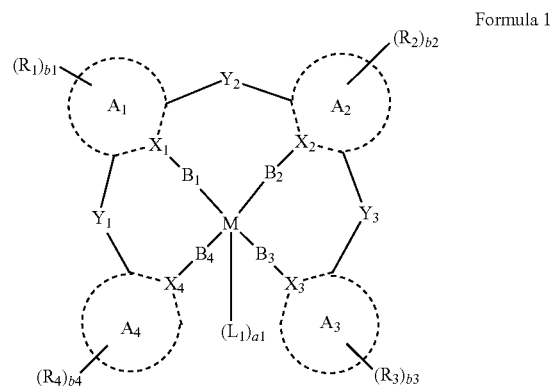

Formula 1 wherein in Formula 1,
M is selected from a Period 1 transition metal, a Period 2 transition metal, and a Period 3 transition metal;
$A_1$ ring and $A_2$ ring are each independently selected from a benzene, a pyridine and a pyrimidine;
$A_3$ ring and $A_4$ ring are each independently selected from a benzene, a pyridine, an isoquinoline, a pyrazole, a dibenzofuran and a tetrahydroindazole;
provided that each of $A_3$ ring and $A_4$ ring is not simultaneously a benzene;
$X_1$ to $X_4$ are each independently selected from C and N;
$B_1$ to $B_4$ are a single bond;
$Y_1$ and $Y_3$ are a single bond;
$Y_2$ is selected from a phenylene group; and
a phenylene group substituted with at least one selected from a deuterium, a methyl group, a tert-butyl group, and a phenyl group;
$L_1$ is selected from a monodentate ligand and a bidentate ligand;
a1 is selected from 0, 1, and 2;
$R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic hetero-condensed polycyclic group, —C(=O)($Q_1$), —Si($Q_1$)($Q_2$)($Q_3$), and —N($Q_1$)($Q_2$); wherein $R_1$ and $R_4$ or $R_2$ and $R_3$ are optionally linked to form a saturated or unsaturated ring;

$Q_1$ to $Q_3$ are each independently selected from a $C_1$-$C_{60}$ alkyl group and a $C_6$-$C_{60}$ aryl group;

b1 to b4 are each independently selected from 1, 2, 3, and 4; and at least one substituent of the substituted $C_6$-$C_{60}$ arylene group, substituted $C_1$-$C_{60}$ heteroarylene group, substituted divalent non-aromatic condensed polycyclic group, substituted divalent non-aromatic hetero-condensed polycyclic group, the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic hetero-condensed polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group.

2. The organometallic compound of claim 1, wherein M is a Period 3 transition metal.

3. The organometallic compound of claim 1, wherein $Y_2$ is selected from Formulae 3-1 to 3-3:

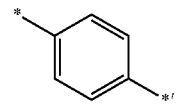

3-1

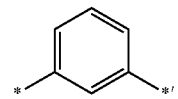

3-2

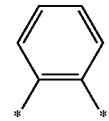

3-3 wherein in Formulae 3-1 to 3-3,
each of * and *' indicates a binding site to a neighboring atom.

4. The organometallic compound of claim 1, wherein $L_1$ is a monodentate ligand, and a1 is 2.

5. The organometallic compound of claim 1, wherein $R_1$ to $R_4$ are each independently selected from a hydrogen, a deuterium, —F, —Cl, —Br, —I, a methyl group, an ethyl group, an n-propyl group, an iso-propyl group, an n-butyl group, an iso-butyl group, a sec-butyl group, a tert-butyl group, —$CF_3$, a methoxy group, an ethoxy group, a tert-butoxy group, a phenyl group, —C(=O)($Q_1$), —Si($Q_1$)($Q_2$)($Q_3$), and —N($Q_1$)($Q_2$); and a phenyl group substituted with a methyl group; wherein $R_1$ and $R_4$ or $R_2$ and $R_3$ are optionally linked to form a saturated or unsaturated ring; and $Q_1$ to $Q_3$ are each independently selected from a methyl group, an ethyl group, an n-propyl group, an iso-propyl group, an n-butyl group, an iso-butyl group, a sec-butyl group, a tert-butyl group, and a phenyl group.

6. The organometallic compound of claim 1, wherein $R_1$ to $R_4$ are each independently selected from a hydrogen, a deuterium, —F, a methyl group, an ethyl group, an n-propyl group, an iso-propyl group, an iso-butyl group, a sec-butyl group, a tert-butyl group, —$CF_3$, a methoxy group, a tert-butoxy group, a phenyl group, —C(=O)($CH_3$), —Si($CH_3$)$_3$, —N($CH_3$)$_2$, —N(Ph)$_2$, and a group represented by Formula 4-1; wherein $R_1$ and $R_4$ or $R_2$ and $R_3$ are optionally linked to form a saturated or unsaturated ring:

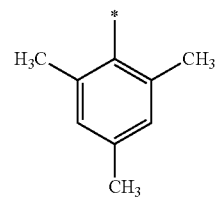

4-1 wherein in Formula 4-1,
* indicates a binding site to a neighboring atom.

7. The organometallic compound of claim 1, wherein the organometallic compound is represented by any one selected from Formulae 1-1 to 1-8:

Formula 1-1
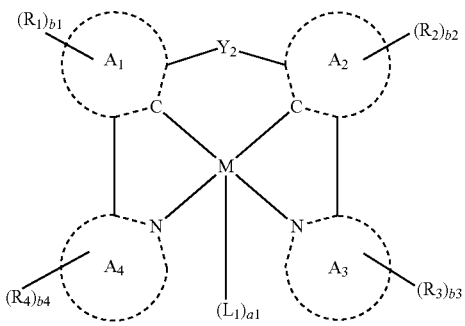
Formula 1-2
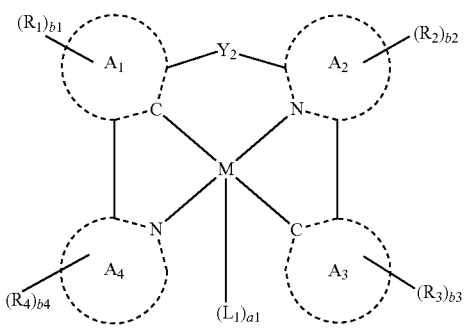
Formula 1-3
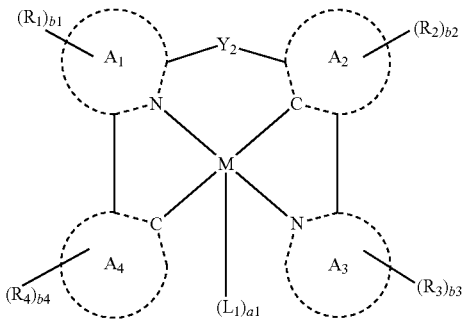
Formula 1-4
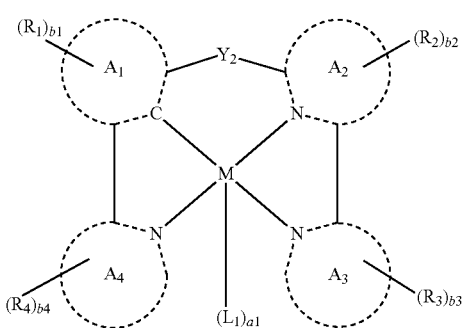
Formula 1-5
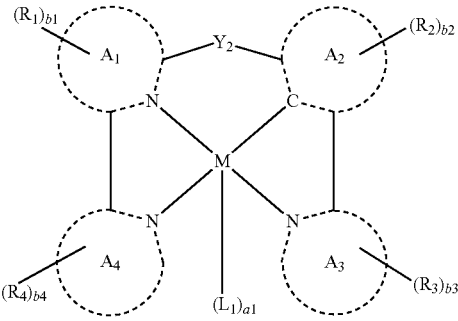
Formula 1-6
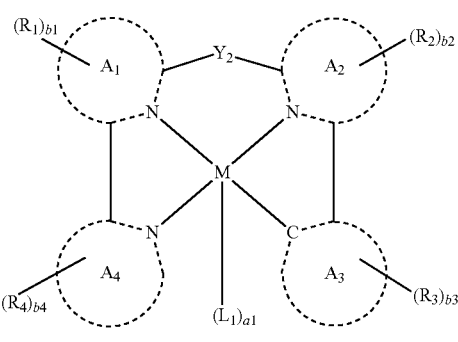
Formula 1-7
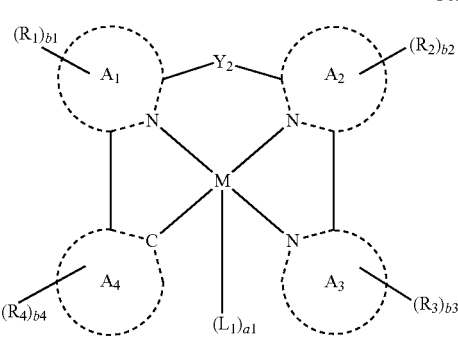
Formula 1-8
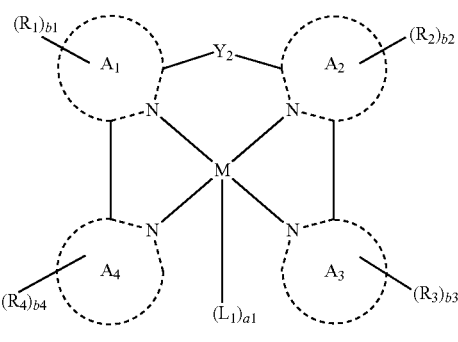
wherein in Formulae 1-1 to 1-8,
M, $A_1$ to $A_4$, $Y_2$, $L_1$, a1, $R_1$ to $R_4$, and b1 to b4 are the same as in Formula 1.
8. The organometallic compound of claim 1, wherein the organometallic compound is represented by any one selected from Formulae 1-1 to 1-8:

Formula 1-1
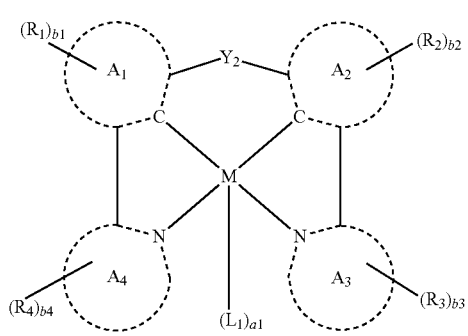

Formula 1-2
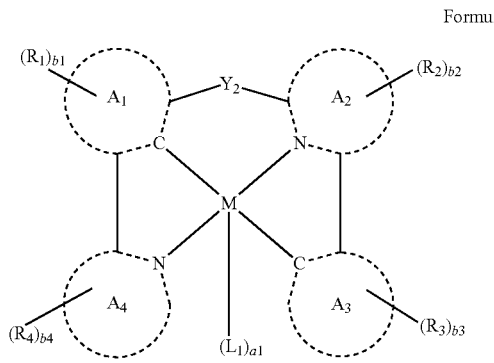

Formula 1-3
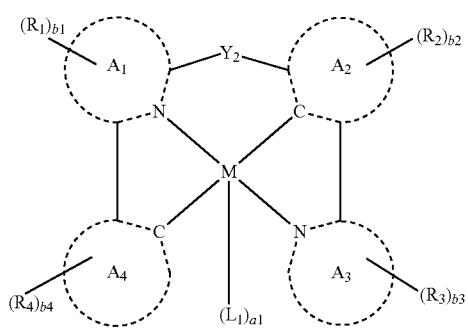

Formula 1-4
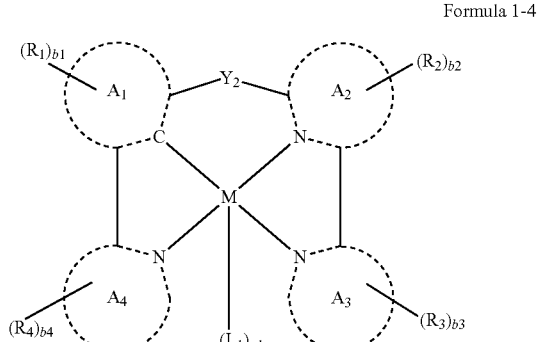

-continued

Formula 1-5
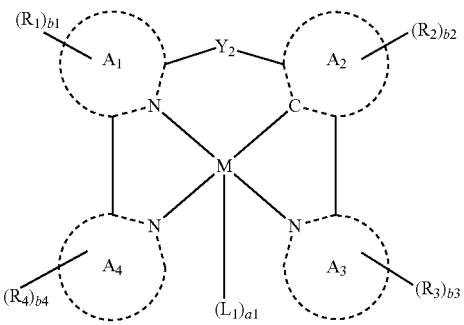

Formula 1-6
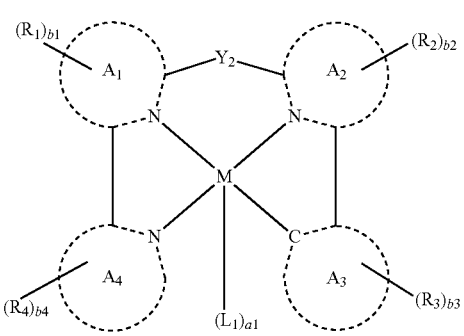

Formula 1-7
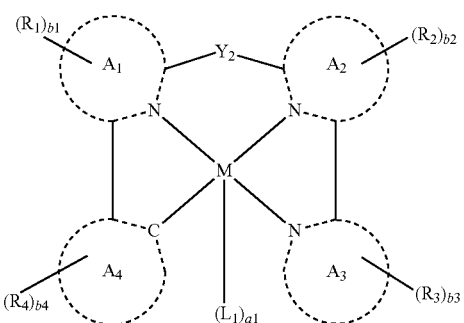

Formula 1-8
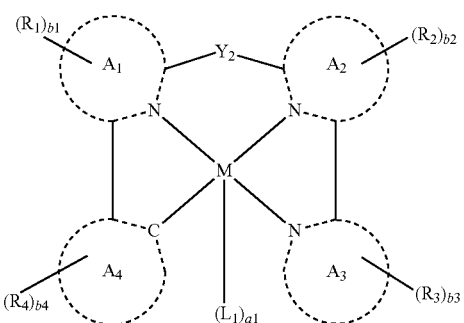

wherein in Formulae 1-1 to 1-8,

M is selected from Os, Ir, and Pt;

$A_1$ ring and $A_2$ ring are each independently selected from a benzene, a pyridine and a pyrimidine;

$A_3$ ring and $A_4$ ring are each independently selected from a benzene, a pyridine, an isoquinoline, a pyrazole, a dibenzofuran and a tetrahydroindazole;

provided that each of $A_3$ ring and $A_4$ ring is not simultaneously a benzene; and $Y_2$ is selected from Formulae 3-1 to 3-3:

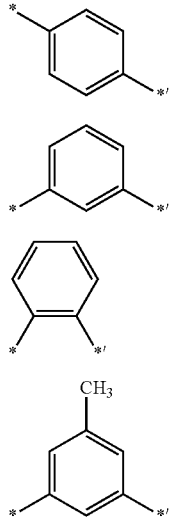

wherein in Formulae 3-1 to 3-3,
each of * and *' indicates a binding site to a neighboring atom;
$R_1$ to $R_4$ are each independently selected from a hydrogen, a methyl group, an ethyl group, an iso-propyl group, an iso-butyl group, a sec-butyl group, a tert-butyl group, —$CF_3$, a phenyl group, —$Si(CH_3)_3$, and a group represented by Formula 4-1;

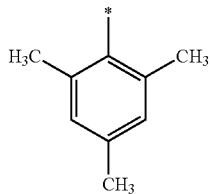

wherein in Formula 4-1,
* indicates a binding site to a neighboring atom; and
b1 to b4 are each independently selected from 1, 2, 3, and 4.

9. The organometallic compound of claim 1, wherein organometallic compound is selected from Compounds 1 to 29:

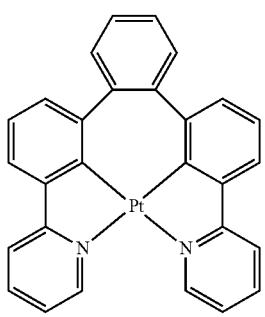

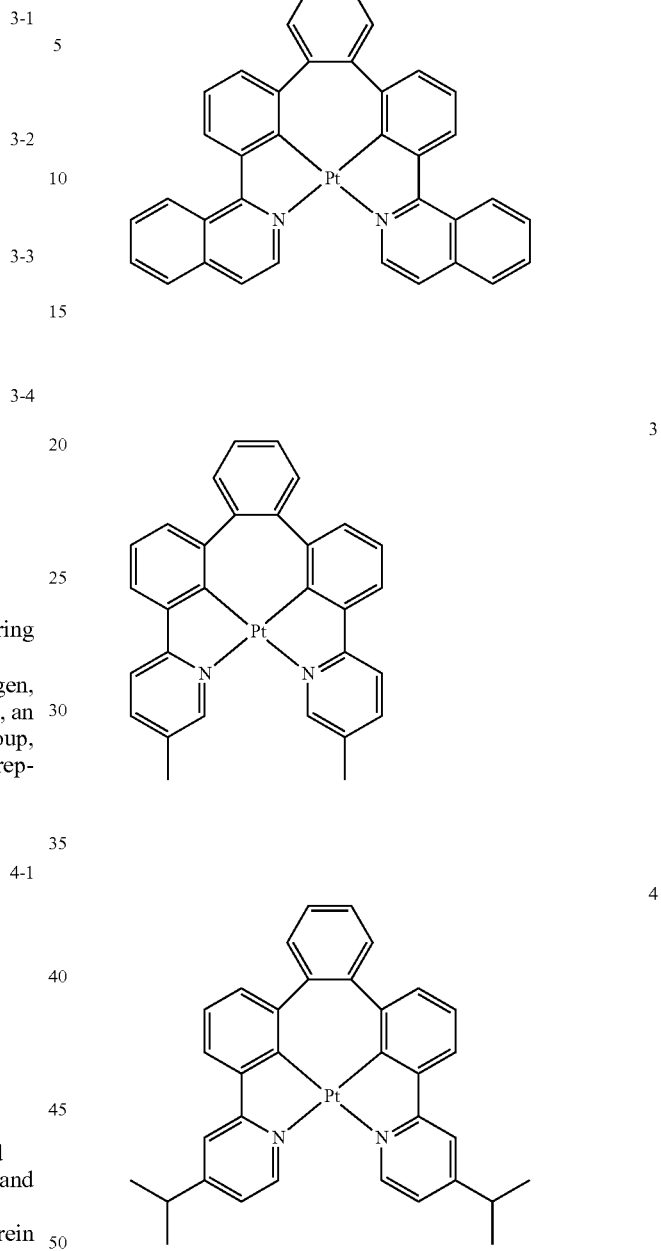

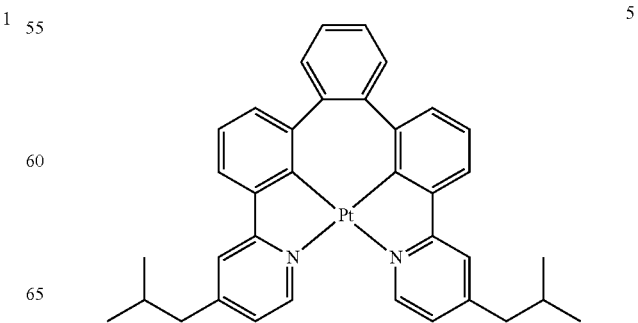

125
-continued
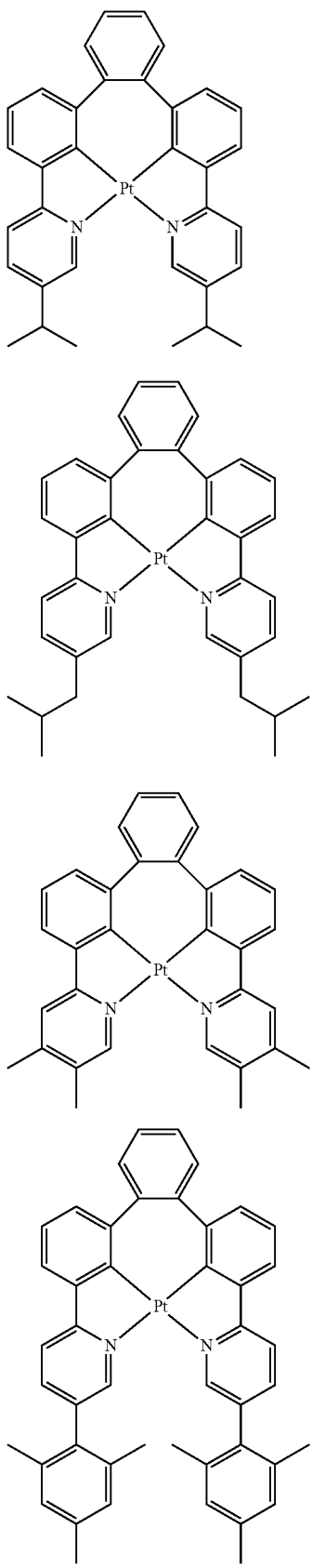
126
-continued
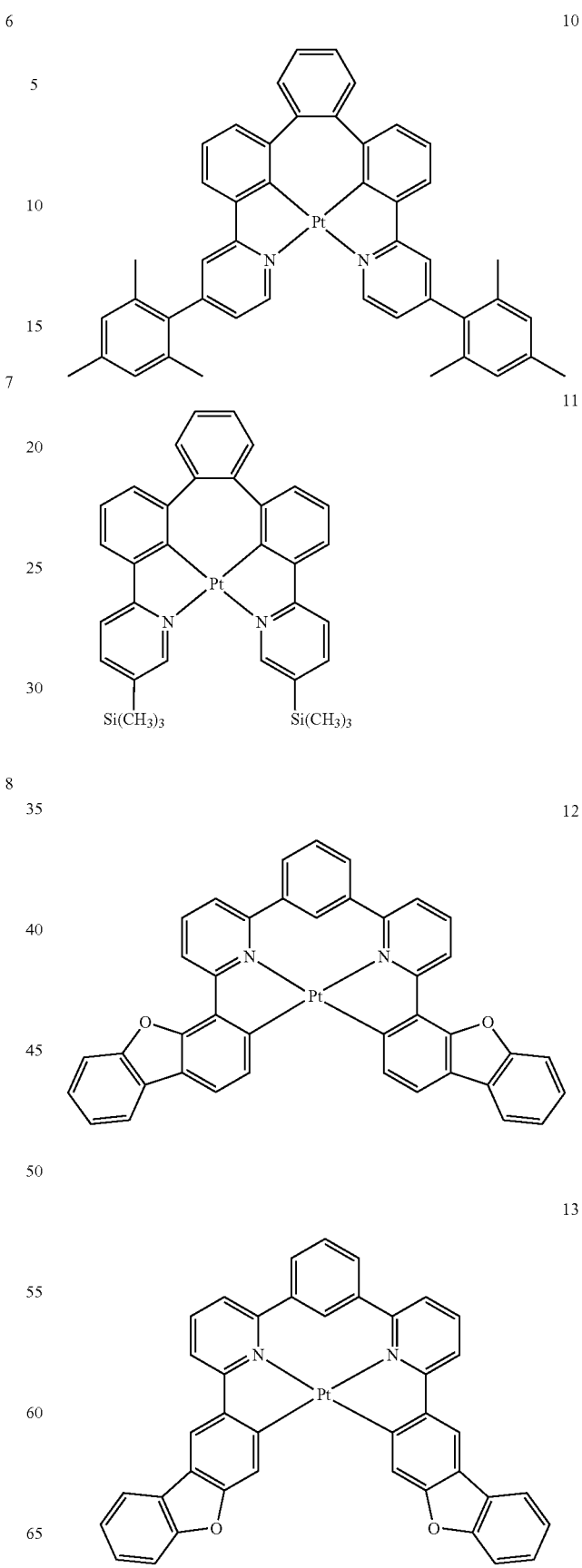

14
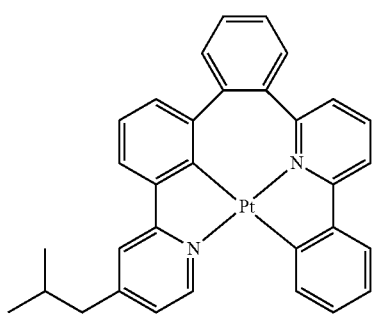
15
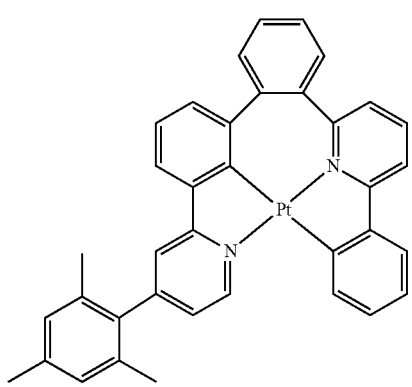
16
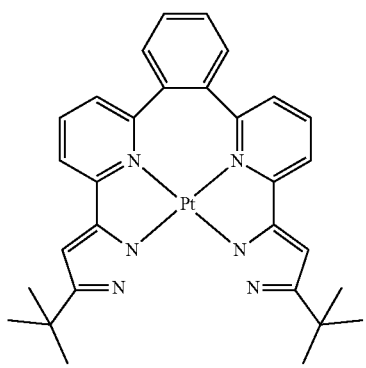
17
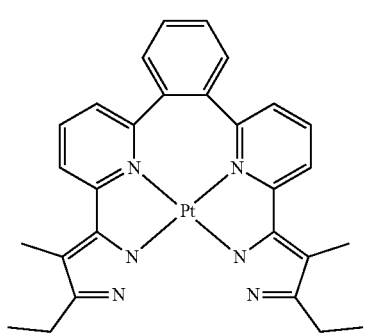
18
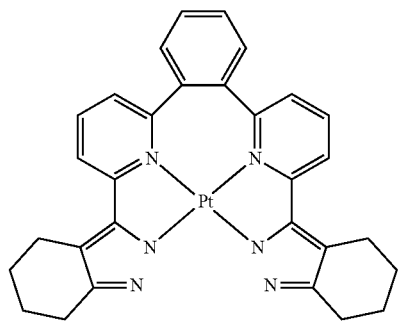
19
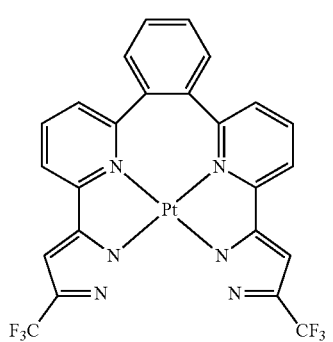
20
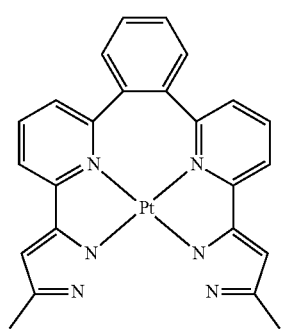
21
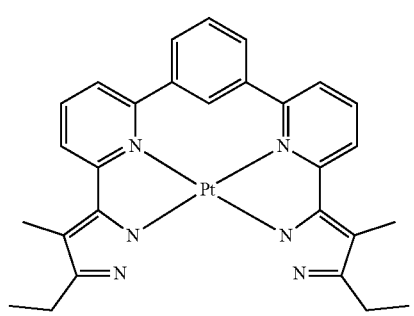
22
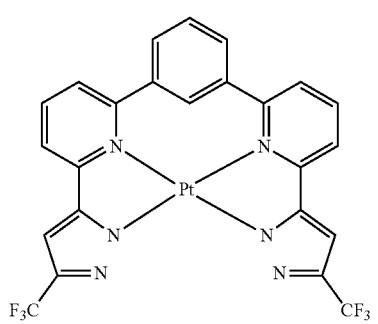

23
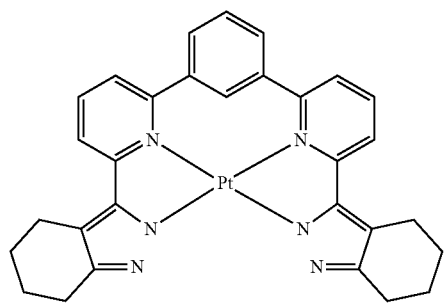
24
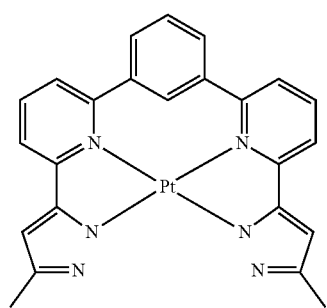
25
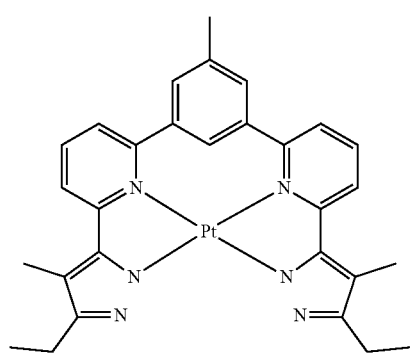
26
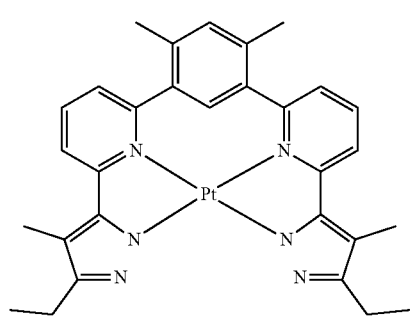
27
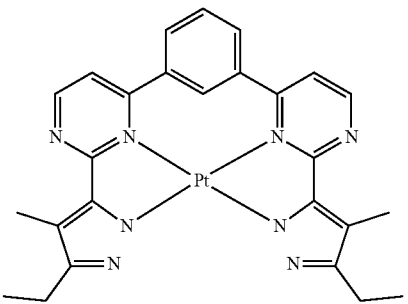
28
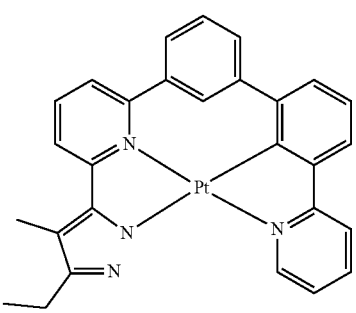
29
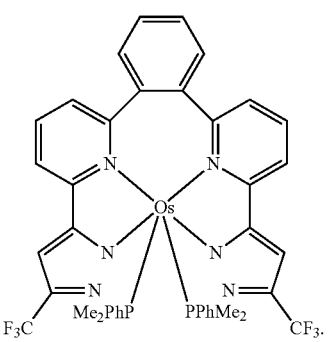
* * * * *